(12) United States Patent
Parthasarathy et al.

(10) Patent No.: US 11,684,069 B2
(45) Date of Patent: Jun. 27, 2023

(54) CATIONIC ANTISEPTIC COMPOSITIONS

(71) Applicant: 3M INNOVATIVE PROPERTIES COMPANY, St. Paul, MN (US)

(72) Inventors: Ranjani V. Parthasarathy, Woodbury, MN (US); Matthew T. Scholz, Woodbury, MN (US); Joshua X. Xiong, Forest Lake, MN (US); Catherine D. Heapy, North St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 20 days.

(21) Appl. No.: 14/917,185

(22) PCT Filed: Sep. 11, 2014

(86) PCT No.: PCT/US2014/055057
§ 371 (c)(1),
(2) Date: Mar. 7, 2016

(87) PCT Pub. No.: WO2015/038689
PCT Pub. Date: Mar. 19, 2015

(65) Prior Publication Data
US 2016/0213001 A1 Jul. 28, 2016

Related U.S. Application Data

(60) Provisional application No. 61/877,401, filed on Sep. 13, 2013.

(51) Int. Cl.
| | | |
|---|---|---|
| A01N 47/44 | (2006.01) |
| A01N 43/40 | (2006.01) |
| A61K 8/44 | (2006.01) |
| A61K 8/41 | (2006.01) |
| A61K 31/155 | (2006.01) |
| A61K 8/46 | (2006.01) |
| A61K 8/49 | (2006.01) |
| A61K 8/40 | (2006.01) |
| A61K 8/86 | (2006.01) |
| A61K 8/39 | (2006.01) |
| A61K 8/43 | (2006.01) |
| A61Q 11/00 | (2006.01) |
| A61L 26/00 | (2006.01) |
| A61K 8/55 | (2006.01) |
| A61Q 17/00 | (2006.01) |
| A61K 8/60 | (2006.01) |
| A01N 25/30 | (2006.01) |

(52) U.S. Cl.
CPC ............ *A01N 47/44* (2013.01); *A01N 25/30* (2013.01); *A01N 43/40* (2013.01); *A61K 8/39* (2013.01); *A61K 8/40* (2013.01); *A61K 8/416* (2013.01); *A61K 8/43* (2013.01); *A61K 8/442* (2013.01); *A61K 8/466* (2013.01); *A61K 8/4926* (2013.01); *A61K 8/4993* (2013.01); *A61K 8/55* (2013.01); *A61K 8/604* (2013.01); *A61K 8/86* (2013.01); *A61K 31/155* (2013.01); *A61L 26/0066* (2013.01); *A61Q 11/00* (2013.01); *A61Q 17/005* (2013.01); *A61L 2300/404* (2013.01)

(58) Field of Classification Search
CPC ........................................................ A01N 47/44
See application file for complete search history.

(56) References Cited

U.S. PATENT DOCUMENTS

| | | | |
|---|---|---|---|
| 4,138,477 | A | 2/1979 | Gaffar |
| 4,879,281 | A | 11/1989 | Shibasaki et al. |
| 5,084,096 | A | 1/1992 | Stovicek |
| 5,408,022 | A | 4/1995 | Imazato et al. |
| 5,885,554 | A * | 3/1999 | Michael ............... A61K 8/21 424/49 |
| 6,440,405 | B1 | 8/2002 | Cooper et al. |
| 6,562,360 | B2 | 5/2003 | Scholz et al. |
| 8,460,689 | B2 | 6/2013 | Wlaschin et al. |
| 2003/0194447 | A1* | 10/2003 | Scholz ............... A01N 59/12 424/672 |
| 2004/0247532 | A1 | 12/2004 | Pinol et al. |
| 2005/0058673 | A1 | 8/2005 | Scholz et al. |
| 2006/0051384 | A1 | 3/2006 | Scholz et al. |

(Continued)

FOREIGN PATENT DOCUMENTS

| | | |
|---|---|---|
| DE | 41 13 684 | 10/1992 |
| EP | 0 300 961 | 1/1989 |

(Continued)

OTHER PUBLICATIONS

Ascenzi, J.M.; Handbook of Disinfectants and Antiseptics; 1996; Table 1 pp. 46-47.

(Continued)

*Primary Examiner* — Yong S. Chong
(74) *Attorney, Agent, or Firm* — 3M Innovative Properties Company

(57) ABSTRACT

An antiseptic composition comprising a multivalent cationic antiseptic present in an amount of 0.05 to 0.5 percent based upon the ready to use composition; an anionic compound which is water soluble in an amount of at least 0.1 grams in 100 grams water at 23 deg C., wherein the anionic compound is present at a concentration which would result in precipitation of the multivalent cationic antiseptic in the composition without a solubilizing surfactant present; wherein the composition, with the antiseptic, surfactant and anionic compound combined with each other, is free of precipitate.

9 Claims, 19 Drawing Sheets

(56) References Cited

U.S. PATENT DOCUMENTS

| | | |
|---|---|---|
| 2006/0051385 A1 | 3/2006 | Scholz |
| 2006/0052452 A1 | 3/2006 | Scholz |
| 2007/0025948 A1* | 2/2007 | Saito ................ A01N 47/44 424/70.31 |
| 2008/0108674 A1 | 5/2008 | Magallon et al. |
| 2010/0285148 A1 | 11/2010 | Wlaschin et al. |
| 2011/0269936 A1 | 11/2011 | Tets et al. |

FOREIGN PATENT DOCUMENTS

| | | |
|---|---|---|
| EP | 0327919 | 8/1989 |
| EP | 0348560 | 1/1990 |
| EP | 0 372 603 | 6/1990 |
| EP | 2 050 434 | 4/2009 |
| GB | 1432487 | 6/1973 |
| GB | 1432487 | 4/1976 |
| JP | 8-119878 | 5/1996 |
| WO | WO-9724927 A1 * | 7/1997 ............. A01N 33/12 |
| WO | WO 98/31332 | 7/1998 |
| WO | WO 1999/62470 | 12/1999 |
| WO | WO 03/067988 | 8/2003 |
| WO | WO 2004/080434 | 9/2004 |
| WO | WO 2005/000253 | 1/2005 |
| WO | WO 2005/022998 | 3/2005 |
| WO | WO 2006/049620 | 5/2006 |
| WO | WO 2006/099359 | 9/2006 |
| WO | WO 2009/058144 | 5/2009 |
| WO | WO 2010/129795 | 11/2010 |

OTHER PUBLICATIONS

SAGE Products Inc. website Jun. 27, 2010 http:/www.sageproducts.com/products/oral-hygiene/proven-to-address-vap.cfm# (15 pgs).

Oral Hygiene Product Catalog from SAGE Products Inc.; 2010; (20 pgs).

Brochure entitled "Medline's VAPrevent & Oral Care Kits: Reducing the Risk of Ventilator-Associaed Pneumonia" from Medline Industries, Inc.; 2008; (23 pgs).

Brochure entitled "Kimberly-Clark* KimVent* Oral Care q4 Kit, q2 Kit & Individual Components/Packs" from Kimberly-Clark; 2008; (6 pgs).

SIDS Initial Assessment Report for SIAM 22. Paris, France. Apr. 18-21, 2006. p. 13. Found at https://www.aciscience.org/docs/SIDS_Amine_Oxides.pdf.

Zong et al. Jul. 2012. *Journal of Pharmaceutical Sciences*. 101(7):2417-2427. "Studies on the Instability of Chlorhexidine, Part I: Kinetics and Mechanisms".

Brazil Search Report for BR112016005528-4 dated Sep. 6, 2019.

* cited by examiner

CATIONIC ANTISEPTIC COMPOSITIONS

CROSS REFERENCE TO RELATED APPLICATIONS

This application is a national stage filing under 35 U.S.C. 371 of PCT/US2014/055057, filed Sep. 11, 2014, which claims priority to U.S. Provisional Patent Application No. 61/877,401, filed Sep. 13, 2013, the disclosure of which is incorporated by reference in its entirety herein.

BACKGROUND

Cationic antiseptics are known to be very effective antimicrobials based upon factors including 1) their high level of antibacterial activity, 2) their ability to bind to mammalian tissue, such as skin, mucosal tissue, oral tissue, and wound tissue, and 3) their prolonged antimicrobial activity on the tissue. Such antiseptics provide fast and persistent killing of both gram-positive and negative bacteria.

However, it is also known that multivalent cationic antiseptics, such as chlorhexidine gluconate (CHG), form precipitates with certain negatively charged compounds. This causes a reduction or even a complete loss of antimicrobial activity. As a result, despite their significant benefits, certain excipients have been avoided or used at much reduce levels in conjunction with multivalent cationic antiseptics in order to prevent compromising the activity of the antiseptic. In one example, sodium saccharin is a very commonly used sweetener in oral rinses and has been used routinely to mask the bitter or bad taste of many formulations. However, multivalent cationic antiseptics, such as CHG were found to precipitate quite easily in the presence of sodium saccharin at certain concentrations and pH's, rendering the antiseptic ineffective. See, for example, International Publication No. WO 2010/129795A1.

As such, there continues to be a need for improved compositions, methods, and products, which are not encumbered by these deficiencies.

SUMMARY OF THE INVENTION

It has now been found that certain surfactants can significantly retard, prevent, or reverse the precipitation of multivalent cationic antiseptics in the presence of a precipitating anionic compound and prevent inactivation of the antiseptic that otherwise would have been caused by the precipitation. Applicants have found that precipitation resulting from the presence of a precipitating anionic compound is particularly destructive to antimicrobial activity of the multivalent cationic antiseptic when the antiseptic is used at low concentrations, for example, at 0.05 to 0.5 wt-% based upon the total weight of a ready-to-use composition. As a result, anionic compounds including, for example, anionic sweeteners, anionic dyes, anionic cellulosic thickeners, anionic phosphates and bicarbonates, and combinations thereof may now be used with multivalent cationic antiseptics without precipitating the antiseptic, while providing a benefit associated with the presence of the anionic compound.

Therefore, there is now provided an antiseptic composition comprising:

a multivalent cationic antiseptic present in an amount of 0.05 to 0.5 percent based upon the ready to use composition;

an anionic compound which is water soluble in an amount of at least 0.1 grams in 100 grams water at 23° C., wherein the anionic compound is present at a concentration which would result in precipitation of the multivalent cationic antiseptic in the composition without a solubilizing surfactant present; and a solubilizing surfactant selected from the group consisting of zwitterionic surfactants, amine oxide surfactants, micelle-forming nonionic surfactants, and combinations thereof;

wherein the solubilizing surfactant is present in sufficient amount to prevent the precipitation; and wherein the composition, with the antiseptic, surfactant and anionic compound combined with each other, is free of precipitate according to Test Method A; and without the surfactant, the composition contains a precipitate according to Test Method A.

For certain embodiments, the antiseptic composition is preferably an aqueous composition wherein water is present in the greatest amount. In certain of these embodiments, a lower alcohol comprising 1 to 4 carbon atoms may be present in an amount less than 20 wt-%, preferably less than 15%. In certain of these embodiments, no lower alcohol is present.

For certain embodiments, the anionic compound is water soluble in an amount of at least 1 gram in 100 grams water at 23° C., and more preferably at least 5 grams in 100 grams water at 23° C.

The antiseptic composition, with the antiseptic, surfactant and anionic compound combined with each other, is free of precipitate according to Test Method A, described herein below. Without the surfactant, the antiseptic composition would contain a precipitate, which can be conveniently determined according to Test Method A, described herein below.

The present antiseptic compositions are useful for application to tissue, such as oral tissue, mucosal tissue, wound tissue, and skin in order to destroy microorganisms or inhibit microorganisms from growing and/or proliferating. The compositions may be, for example, rinses, creams, moisturizers, toothpastes, debriding solutions, perioperative preparations, and the like. In addition, the present antiseptic compositions may be used with (including mixing with) other compositions containing an anionic excipient. Such other compositions may be, for example, rinses, creams, moisturizers, toothpastes, gels, lotions, tissue antiseptics, debriding solutions, and the like.

In another embodiment, there is provided an oral care kit comprising the antiseptic composition and a delivery device. For certain of these embodiments, the oral care kit is for treating a mechanically ventilated patient for xerostomia and to prevent ventilator associated pneumonia.

In another embodiment, there is provided a method of decolonizing mucosal tissue comprising contacting the mucosal tissue with the antiseptic composition. For certain of these embodiments, the tissue is oral tissue.

In another embodiment, there is provided a method of decontaminating wound tissue by contacting the wound tissue with the antiseptic composition. For certain of these embodiments, the wound tissue is an acute surgical wound and the composition is used to irrigate the surgical wound. In other embodiments the wound tissue is a chronic wound and the composition is used to irrigate the wound, debride the wound, or both.

In another embodiment, there is provided a method of pretreating a medical device by exposing the device to the antiseptic composition.

In another embodiment, there is provided a method of preparing an antiseptic composition according to any one of the embodiments described herein, the method comprising:

providing a composition comprising a solution of the multivalent cationic antiseptic;

providing a composition comprising the anionic compound at a concentration sufficient to precipitate the multivalent cationic antiseptic when the anionic compound composition and multivalent cationic antiseptic composition are combined in the absence of the solubilizing surfactant;

wherein the multivalent cationic antiseptic composition, the anionic compound composition, or both further comprise the solubilizing surfactant;

combining the multivalent cationic antiseptic composition with the anionic compound composition to form the antiseptic composition without precipitating the multivalent cationic antiseptic.

In a further embodiment, there is provided a method of preparing an antiseptic composition according to any one of the embodiments described herein, the method comprising:

providing a composition comprising a solution of the multivalent cationic antiseptic;

providing a composition comprising the anionic compound at a concentration sufficient to precipitate the multivalent cationic antiseptic when the anionic compound composition and multivalent cationic antiseptic composition are combined in the absence of the solubilizing surfactant;

combining the multivalent cationic antiseptic composition with the anionic compound composition to form a mixture comprising at least a portion of the multivalent cationic antiseptic as precipitate;

combining the solubilizing surfactant with the mixture to form the antiseptic composition free of the precipitate.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Definitions

The following terms are used herein according to the following definitions.

"Oral tissue" refers to oral mucosal tissue, teeth, whether natural or prosthetic, within the oral cavity, tongue, and lips. Oral mucosal tissue includes, for example, gingiva, buccal mucosa, the floor of the mouth, the hard palate, the soft palate, the dorsal tongue, the lateral tongue, the ventral tongue, an oropharyngeal surface, and combinations thereof.

"Mucosal tissue" refers to the surfaces of the oral (e.g., mouth) cavity, vaginal tissue, sinus tissue, and other similar tissues.

"Decolonizing" and "Decolonization" refer to a reduction in the number of microorganisms (e.g., bacteria) present in or on tissue that do not necessarily cause immediate clinical symptoms. Ordinarily fewer microorganisms are present in "colonized tissue" than in "infected tissue." When the tissue is completely decolonized the microorganisms have been "eradicated".

It should be understood that (unless otherwise specified) the concentrations of the components listed herein are for "ready to use" or "as used" compositions. In certain other embodiments, the compositions can be in a concentrated form that would be diluted by the user with an appropriate vehicle.

"Precipitate" means a separate phase, e.g., a solid or a gel that separates out from the multivalent cationic antiseptic solution, including a cloudiness that represents suspended solid or gel particles.

"Stable" means physically stable or chemically stable, which are both defined in greater detail below. Preferred compositions are both chemically and physically stable.

"Microorganism" or "microbe" refers to bacteria, yeast, mold, fungi, protozoa, mycoplasma, as well as viruses (including lipid enveloped RNA and DNA viruses).

"Treat" or "treatment" means to improve the condition of a subject relative to an affliction, typically in terms of clinical symptoms of the condition.

"Subject" and "patient" includes humans, sheep, horses, cattle, pigs, dogs, cats, rats, mice, or other mammals.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

BRIEF DESCRIPTIONS OF THE DRAWINGS

DETAILED DESCRIPTION OF ILLUSTRATIVE EMBODIMENTS

Figure 1:
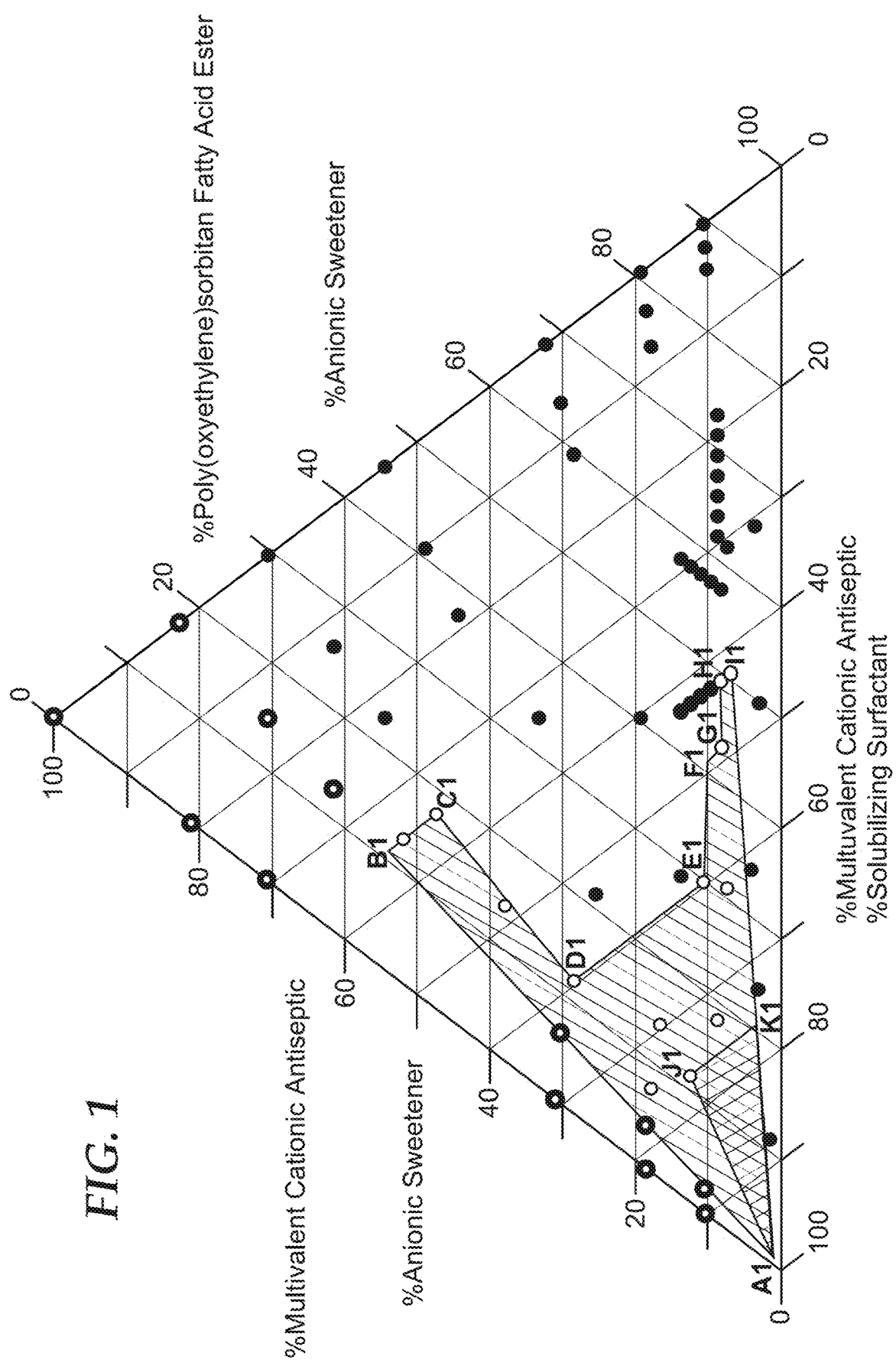
FIG. 1 is a composite phase diagram of % multivalent cationic antiseptic, % anionic sweetener, and % solubilizing surfactant, showing the regions without and with precipitate.

As indicated above, it has now been found that certain surfactants can prevent the precipitation of multivalent cationic antiseptics in the presence of a precipitating anionic compound. Inactivation of the antiseptic that otherwise would have been caused by the precipitation is thereby prevented. This is a significant advancement in the preparation and use of multivalent cationic antiseptic compositions, since many anionic compounds including, for example, anionic sweeteners, anionic dyes, anionic cellulosic thickeners, anionic phosphates and bicarbonates, and combinations thereof may now be used or be present with multivalent cationic antiseptics without precipitating the antiseptic, while providing a benefit associated with the presence of the anionic compound. Such benefits include, for example, masking the taste of the multivalent cationic antiseptic, more clearly visualizing where the composition has been applied, thickening the composition for better substantivity, and preventing deactivation of the antiseptic caused by unavoidable contact with anionic compounds present on tissue.

One area to which these findings can be applied is that of oral care. In one example, saliva in the mouth is buffered by bicarbonate and phosphate. When a multivalent cationic antiseptic-containing mouth rinse is applied, the bicarbonate and phosphate salts of the multivalent cationic antiseptic can form, rendering the antiseptic biologically inactive. However, the antiseptic in combination with one or more surfactants according to the present invention can overcome this effect and maintain biological activity of the multivalent cationic antiseptic. Surprisingly, some of the surfactants, now found to preserve the antimicrobial activity of the cationic antiseptics, were previously used to neutralize activity of cationic antiseptics in combination with other surfactants such as lecithin. See, for example, Handbook of Disinfectants and Antiseptics edited by Joseph M. Ascenzi, 1996 Marcel Dekker, Table 1 pp. 46-47.

In another example, ventilated patients as well as a significant segment of the population suffer from xerostomia (dry mouth). Without the normal salivary flow, which not only mechanically washes off bacteria but also contains enzymes, antibodies, and other components important to the immune system, xerostomia favors bacterial proliferation. In the case of mechanically ventilated patients, the xerostomia has been treated by periodic application of a mouth moisturizer. Bacterial proliferation has been treated with a chlorhexidine gluconate-containing mouth rinse to help reduce or prevent dental plaque, gingivitis, periodontal disease, as well as overgrowth of opportunistic microorganisms, and to help reduce the incidence of ventilator associated pneumonia.

The present invention provides compositions which can be used for decolonizing mammalian tissue, such as mucosal tissue and oral tissue. There is also provided an oral care kit including compositions for decolonizing the tissue and articles, such as delivery devices which can be used for treating the tissue. Oral tissue moisturizers used in commercial kits with a CHG oral rinse were previously found to significantly reduce the antibacterial activity of the CHG oral rinse, and that components of these kits chemically inactivated the CHG. In the case of mechanically ventilated patients, any treatment regimen must address both the reduction of microorganisms (plaque removal and reduction of opportunistic organisms in the oral cavity) and xerostomia without having the products used for these purposes interact with each other so as to reduce the effectiveness of any one of the products.

The present compositions can be used for moisturizing mucosal and oral tissues in the presence of a multivalent cationic antiseptic without deactivating the antiseptic. In one example, a composition is provided which includes a moisturizing component, a multivalent cationic antiseptic, a surfactant as described above, and an anionic compound which precipitates the antiseptic in the absence of the surfactant as discussed above. This composition can decolonize and moisturize the tissue. In another example, a two-part composition is provided, one part being a moisturizing composition and the second part being a multivalent cationic antiseptic composition. A surfactant as described above is included in the antiseptic composition, the moisturizing composition, or both. An anionic compound which precipitates the antiseptic in the absence of the solubilizing surfactant is included in the moisturizing composition part. In this instance, the multivalent cationic antiseptic part may be applied only sparingly (e.g., one or two times in a 24 hour period) and the moisturizing composition part may be applied separately many times as needed (e.g., 2, 3, 4, 5, 6 or more times in a 24 hour period). In another example, the two parts may be mixed together and then immediately applied. In any case, the presence of the surfactant prevents or significantly retards precipitation of the multivalent cationic antiseptic with the included anionic compound.

Another area to which these findings can be applied is that of perioperative care. In one example, a perioperative preparation comprising the present composition is applied to the nasal cavity, the oral cavity, skin, and/or the surgical site. The affected tissues are thereby decolonized, eliminating or reducing the incidence of infections during and subsequent to perioperative care. As a result, the benefits of preventing precipitation of the multivalent cationic antiseptic in the presence of certain anionic compounds as discussed above can be realized in these applications as well. Here again, the composition can be provided as a one-part, a two-part, or a multi-part composition. In one example, the composition includes a first part containing the precipitating anionic compound and a second part containing the multivalent cationic antiseptic, wherein the solubilizing surfactant is present in either or both parts. Prior to applying the composition to a subject, the parts are combined.

In an alternative embodiment, the composition may be formed in situ. For example, a composition comprising the multivalent cationic antiseptic and the solubilizing surfactant may be provided, and when the composition is applied to tissue with an anionic compound thereon, the final composition is formed without precipitating the multivalent cationic antiseptic. In such instances, the anionic compound could include, for example, phosphate anions, bicarbonate anions, or both, as could be the case for saliva on mucosal tissue.

Because the order in which the components of the present composition are combined can change according to the various ways the composition can be provided and prepared, the test method for determining whether or not a precipitate has formed can be carried out with more than one order of addition. For example, Test Method A described below combines the surfactant with the anionic compound and then adds the cationic antiseptic. The same test could be run by combining the surfactant with the cationic antiseptic and then adding the anionic compound. Thus, Test Method A may encompass both orders of addition. Moreover, applicants note that in some cases where a precipitate forms when the cationic antiseptic and the anionic compound are combined, addition of the surfactant reverses the precipitate formation, providing a clear solution.

Multivalent cationic antiseptics, such as CHG, can persist on mammalian tissue, including mucosal such as in the oral cavity for a number of hours, for example, for up to 5 hours, 10 hours, 12 hours, or even longer. This persistence helps keep pathogenic bacterial counts low on the tissue, preventing bacterial infection and, in the case of the oral cavity, helping in the prevention of plaque and gingivitis, which is vital for the care of mechanically ventilated patients in hospitals. For certain embodiments, preferably this benefit can be sustained using the compositions, kits, and methods described herein, despite the presence of an otherwise precipitating anionic compound.

In the embodiments described herein, whether or not a precipitate is formed can be determined using Test Methods A as described below. The compositions provided herein contain the multivalent cationic antiseptic, the anionic compound, and the solubilizing surfactant in amounts relative to each other such that when combined in those amounts no visually observable precipitate is formed. In certain embodiments, no precipitate is observed within 15 minute, 30 minutes, or one or more hours at room temperature (23° C.). In certain embodiments, no precipitate is observed within at least two weeks, preferably at least one month, more preferably at least 4 months, most preferably at least 6 or 10 months at room temperature (23° C.).

The precipitate includes multivalent cationic antiseptic. When such a precipitate forms, the amount of multivalent cationic antiseptic that remains soluble, and therefore active, may have been reduced. The degree to which the amount is reduced can be determined by assaying the amount of multivalent cationic antiseptic in the solution in which it resides using standard analytical techniques, such a liquid chromatograpy, light absorbance, and/or other known methods.

A bacterial assay can be used to determine when the present composition provides sufficient antimicrobial activity. One readily performed assay involves exposing a selected known or readily available viable microorganism strain, such as *Enterococcus* spp., *Aspergillus* spp., *Escherichia* spp. (e.g., *E. coli*), *Staphylococcus* spp. (e.g., *Staphylococcus aureus*), *Streptococcus* spp. (e.g., *Streptococcus pneumonia*), *Pseudomonas* spp. (e.g., *Pseudomonas aeruginosa*), *Enterobacter* spp., or *Salmonella* spp., or other microorganism such as *Haemophilus influenza* or *Acinetobacter baumannii*, to a test composition at a predetermined bacterial burden level in a culture media at an appropriate temperature. This may be conveniently carried out using the Test Method B described in the Examples Section. Briefly, in Test Method B, approximately $10^6$ cfu's are inoculated into a test composition. After incubation for a specific time period, the mixture is neutralized and enumerated by dilution plating.

For certain embodiments, the present multivalent cationic antiseptic compositions provide a $\log_{10}$ reduction in the number of viable bacterial cells of at least 1 when $10^6$ cfu of *Staphylococcus aureus* are combined with the composition according to Test Method B. Preferably the log reduction occurs within 10 minutes, most preferably within 5 minutes. Preferably, a $\log_{10}$ reduction in the number of viable bacterial cells of at least 1 or 2 is provided. Bacterial reduction is generally reported as $\log_{10}$ reduction determined by the difference between the $\log_{10}$ of the initial inoculum count and the $\log_{10}$ of the inoculum count after exposure to the antiseptic composition.

The present compositions may provide residual antimicrobial efficacy by maintaining an average $\log_{10}$ reduction of at least 1 log, more preferably at least 1.5 log, and even more preferably at least 2 log, for at least 1 hour, more preferably at least 2 hours, and even more preferably at least 4 hours after application to oral tissue.

Multivalent cationic antiseptics, such as chlorhexidine, kill both gram-positive and gram-negative microbes. In addition, they are active against lipid enveloped viruses and fungi. At least one mechanism of action is believed to be membrane disruption. Examples of relevant microorganisms against which the antiseptics are active include *Staphylococcus* spp., *Streptococcus* spp., *Pseudomonas* spp., *Enterococcus* spp., and *Esherichia* spp., *Aspergillus* spp., *Fusarium* spp., *Acinetobacter* spp., and *Candida* spp. Particularly virulent organisms include *Staphylococcus aureus* (including resistant strains such as Methicillin Resistant *Staphylococcus Aureus* (MRSA), *Staphylococcus epidermidis*, *Streptococcus mutans*, *Streptococcus pneumoniae*, *Enterococcus faecalis*, Vancomycin Resistant *Enterococcus* (VRE), *Pseudomonas aeruginosa*, *Escherichia coli*, *Aspergillus niger*, *Aspergillus fumigatus*, *Aspergillus clavatus*, *Fusarium solani*, *Fusarium oxysporum*, *Fusarium chlamydosporum*, *Candida albicans*, *Candida glabrata*, and *Candida krusei*. For certain embodiments, those microorganisms relevant to the oral cavity and oral tissue, for example, of a mechanically ventilated subject, include *Staphylococcus aureus*, *Streptococcus pneumonia*, *Pseudomonas aeruginosa*, *Haemophilus* influenza and *Acinetobacter baumannii*, and *Enterobacter* spp.

Multivalent cationic antiseptics include compounds which contain two or more nitrogen atoms having a positive charge. Nitrogen atoms which are not quaternary nitrogen atoms can be positively charged by protonation. For certain embodiments, including any one of the above embodiments, the multivalent cationic antiseptic is selected from the group consisting of biguanides, bisbiguanides, polymeric biguanides, polyguanidines, polymeric quaternary ammonium compounds, polymeric and oligomeric poly-protonated tertiary, secondary, or primary amines, surfactants comprising at least 2 cationic nitrogen atoms and at least one and preferably at least two C8-C16 alkyl or alkylene or C10-C22 alkenyl or alkenylene groups, such as octenidine and hexetidine, and combinations thereof. Biguanides include the following 2-carbamimidoylguanidine structure of formula (I):

wherein at least one of $R^1$, $R^2$, $R^3$, and $R^4$ is an alkyl, aryl, or arylalkyl group, and any remaining $R^1$, $R^2$, $R^3$, or $R^4$ groups are hydrogen.

Bisbiguanides include the following bis(2-carbamimidoylguanidine) structure of formula (II):

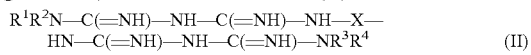

wherein at least one of $R^1$, $R^2$, $R^3$, and $R^4$ is an alkyl, aryl, or arylalkyl group, any remaining $R^1$, $R^2$, $R^3$, or $R^4$ groups are hydrogen, and X is a divalent connecting group, for example, a straight-chain or branched $C_{3-10}$ alkylene group, optionally interrupted with —O—, —S—, or arylene (e.g., phenylene, naphthylene), preferably straight-chain $C_{4-8}$ alkylene preferably straight-chain hexylene.

At least one of $R^1$ and $R^2$ and at least one of $R^3$ and $R^4$ is preferably hydrogen. Alkyl groups include, for example, $C_{1-18}$ alkyl groups, preferably $C_{1-8}$ alkyl groups. Aryl groups include $C_{6-10}$ aryl groups, preferably phenyl groups. Arylalkyl groups include any combination of these alkyl and aryl groups, for example, benzyl and 2-phenylethyl. Any of these groups may be substituted with one or more halo, nitro, $C_{1-4}$ alkyl, $C_{1-4}$ alkoxy, $C_{4-9}$ cycloalkyl, or a combination of these groups.

Polybiguanides include the following polymeric structure of formula (III) wherein X is as described above; Z is a terminal group such as an amino group or salt thereof, a dicyandiamido group or a cyanoguanidino group; and n is at least 3 and not more than about 50, preferably at least 4 and not more than about 40, more preferably at least 5 and not more than 20:

$$Z—[X—HN—C(=NH)—NH—C(=NH)—NH—]_n \\ X—Z \quad \text{(III)}$$

Polyguanidines include polymeric structures in which the guanidine core structure, —N—C(=N—)—N—, is included in the repeating units of the polymer.

Polymeric protonated tertiary amines include polymeric structures in which tertiary amino groups are included in or attached to the repeating units of the polymer. Alternatively or in addition to protonated tertiary amino groups, protonated secondary and/or protonated primary amino groups may be included in these polymeric structures.

Octenidine and hexetidine are represented by the following chemical structures, respectively:

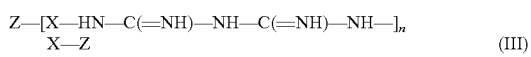

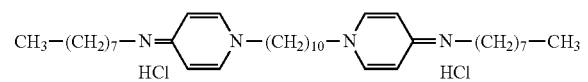

Examples of biguanides of formula (I) include but are not limited to Metformin ($R^1$ and $R^2$=methyl), Buformin ($R^1$=n-butyl), Phenformin ($R_1$=2-phenylethyl), and the like. Examples of bisbiguanides of formula (II) include but are not limited to chlorhexidine (X is —$(CH_2)_6$—, and $R^1$ and $R^3$ are 4-chlorophenyl) and alexidine (1,1'-hexamethylene-bis[5-(2-ethylhexyl)biguanide]) and their various salts such as the digluconate, diacetate, dimethosulfate, and dilactate salts as well as combinations thereof. Examples of polybiguanides include but are not limited to PHMB (poly(hexamethylenebiguanide)) and salts thereof. In one preferred form, PHMB is commercially available as Cosmocil CQ from Arch Chemicals Inc., Smyrna Ga. Examples of polyguanidines include those described in U.S. Patent Application Publication No. 2011/0269936.

Polymeric quaternary ammonium compounds include polymers having quaternary amine groups with at least one alkyl or aralkyl chain of at least 6 carbon atoms and preferably as least 8 carbon atoms. The polymers may be linear, branched, hyperbranched or dendrimers. Examples of antimicrobial polymeric quaternary amine polymers include but are not limited to quaternary ammonium functionalized dendrimers such as those described in U.S. Pat. No. 6,440,405; polymers which are the polymerization product of quaternary ammonium functional (meth)acrylate monomers such as those described in U.S. Pat. No. 5,408,022; polyethers, polycarbonates, and polyurethanes prepared from quaternary ammonium functional diols such as those described in U.S. Pat. No. 5,084,096; and the like Any soluble salt of the multivalent cationic antiseptic, including the above described salts, may be used. For example, where hydrochloride salts are soluble, such salts are suitable.

"Soluble" as used herein with respect to the multivalent cationic antiseptic and/or salts thereof refers to solubility in a composition, for example, an aqueous fluid, above the minimum inhibitory concentration (MIC) of the treatment microorganism. If the solubility limit is less than the MIC, treatment may be ineffective. Preferably the solubility exceeds the minimum bacteriacidal concentration (MBC).

For certain embodiments, including any one of the above embodiments, preferably the multivalent cationic antiseptic is selected from the group consisting of bisbiguanides, polymeric biguanides, surfactants comprising at least 2 cationic nitrogen atoms and at least two (C8-C16) alkyl or alkylene or (C10-C22) alkenyl or alkenylene groups, such as octenidine and hexetidine, and combinations thereof. For certain of these embodiments, the multivalent cationic antiseptic is a bisbiguanide, a polymeric biguanides, octenidine, or a combination thereof.

For certain embodiments, including any one of the above embodiments, preferably the multivalent cationic antiseptic is a bisbiguanide or a polybiguanide. For certain of these embodiments, the multivalent cationic antiseptic is chlorhexidine or PHMB. For certain of these embodiments, the multivalent cationic antiseptic is PHMB. Alternatively, for certain of these embodiments, the multivalent cationic antiseptic is chlorhexidine. The multivalent cationic antiseptic may be present as the free base, but is preferably present as a soluble salt. For example, chlorhexidine may be present as the free base but is preferably present as a disalt of acetate, gluconate, lactate, methosulfate ($CH_3OSO_3^-$), or combinations thereof. These salts all have solubility limits in water in excess of 1 g/100 ml. For example, the solubility limit of the digluconate salt is at least 20 g/100 ml and that of the diacetate is 1.9 g/100 ml. For certain of these embodiments, preferably the multivalent cationic antiseptic is chlorhexidine digluconate (CHG). In one alternative, preferably the multivalent cationic antiseptic is the hydrochloride of PHMB.

The present compositions comprise a solution of the multivalent cationic antiseptic. For certain embodiments, the solution is an aqueous solution or a water/alcohol solution of the antiseptic. In other embodiments the composition is an emulsion such as a water-in-oil or oil-in-water emulsion wherein the multivalent cationic antiseptic is dissolved and in solution. For certain embodiments, preferably the compositions comprise an aqueous solvent, such as water or water and a lower alcohol. Lower alcohols include methanol, ethanol, propanols, and butanols, preferably ethanol.

For optimal multivalent cationic antiseptic activity, for example, maximizing antimicrobial effectiveness, the pH of the present compositions is preferably in the mildly acidic to approximately neutral range, for example, a pH of 3 to 8 or 4 to 8. Preferably, the pH is at least 4.5, at least 5, or at least 6 and not greater than 7.5, preferably not greater than 7. More preferably, the pH is 4.5 to 7, and most preferably 6 to 7.

The multivalent cationic antiseptics are dissolved in an aqueous carrier, for example water or water and a lower alcohol (preferably ethanol, 2-propanol or n-propanol), a non-aqueous carrier, or a combination thereof and protected from light. Protection from light and use of a non-aqueous carrier may help reduce the degradation of susceptible antiseptic compounds over time. For example, many amine compounds can oxidize with exposure to light. When used in compositions comprising less than about 20% by weight water, these antiseptics are preferably formulated with a hydrophilic carrier that solubilizes the antiseptic. Examples of suitable solvents for many multivalent cationic antiseptics, including chlorhexidine gluconate, include glycols (compounds having at least two hydroxyl groups per molecule) such as PEGs having a molecular weight below 2000 and preferably less than 1000 and most preferably less than about 800 daltons; glycerin and polyglycerols, propylene glycol, dipropylene glycol, tripropylene glycol, polypropylene glycol, ethylene oxide/propylene oxide random or block copolymers, trimethylolpropane, pentaerythritol, sorbitol, panetothenol, glucuronolactone, gluconic acid, and the like as well as other polar solvents such as N-methyl pyrrolidone, propylene carbonate, butyrolactone and the like.

Care may be taken when formulating chlorhexidine as well as other multivalent cationic antiseptic compounds to avoid inactivation by sequestering it in micelles which may be formed by incorporation of excessive amounts surfactants and/or emulsifiers (for example, certain nonionic surfactants in combination with lecithin). Some examples of formulations that may be used include hydrophilic ointments; aqueous solutions thickened with polymeric thickeners that contain surfactants that do not inactivate the CHG; and ointments comprising a major amount of a hydrophobic component and preferably further comprising a hydrophilic component.

The multivalent cationic antiseptics, such as chlorhexidine, are very basic and capable of forming multiple ionic bonds with anionic materials. For this reason, it is particularly surprising that precipitation of the antiseptic in the present multivalent cationic antiseptic compositions is prevented, even though one or more precipitating anionic materials are present. Preventing precipitation is especially advantageous where relatively low concentrations of the multivalent cationic antiseptic are used, for example, 0.05 to 0.5 wt-%. At such low levels, any precipitation of the antiseptic can cause a significant reduction in antimicrobial efficacy, whereas at higher levels, even when some precipitation occurs, there may be sufficient antiseptic remaining to maintain efficacy. Note that cationic antiseptics are known to bind to other organic matter in treatment areas such as on tissue, so typically levels must be considerably higher than the minimum bactericidal concentration (MBC) normally found without organic matter. Preferably, the antiseptic concentration in the presence of the anionic compound and surfactant is at least 10 times the MBC of the organism of interest. More preferably it is 50 and even 100 times the MBC. In certain preferred embodiments the antiseptic will be present at over 500 times the MBC.

For certain embodiments, preferably the multivalent cationic antiseptic is included in a composition at a sufficient concentration such that when applied to mammalian tissue for an adequate time, with an adequate frequency, and in an adequate dose the antiseptic can provide at least a 1 or a 2 log reduction, decolonize, or eradicate at least one species of microorganism from the tissue. For certain embodiments, the present compositions preferably contain at least 0.05 or 0.1 wt-% multivalent cationic antiseptic. Preferably, for certain embodiments, not more than 0.5, 0.4, 0.3, or 0.25 wt-% multivalent cationic antiseptic is present.

The multivalent cationic antiseptics may be used alone, in combination, or with other antiseptics in order to effectively kill microorganisms on the tissue. Additional antiseptics for use with the multivalent cationic antiseptic include peroxides, antimicrobial natural oils, and compatible combinations thereof as provided in U.S. Patent Application Publication No. 2006/0051384 A1; diphenyl ethers, phenols, halogenated phenols, bisphenols, resorcinols and its derivatives, anilides, and combinations thereof, provided in U.S. Patent Application Publication No. 2006/0052452 A1. Also, antimicrobial lipid antiseptics may additionally be used. Such antimicrobial lipids include (C7-C14) saturated fatty acid esters of a polyhydric alcohol, (C8-C22) unsaturated fatty acid esters of a polyhydric alcohol, (C7-C14) saturated fatty ethers of a polyhydric alcohol, (C8-C22) unsaturated fatty ethers of a polyhydric alcohol, and alkoxylated derivatives thereof, or combinations thereof, wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof. Useful antiseptics of this class are further described in U.S. Patent Application Publication No. 2005/0058673.

Other useful antimicrobial lipids include a (C8-C12)fatty alcohol ester of a (C2-C8)hydroxycarboxylic acid (also often referred to as a (C2-C8)hydroxycarboxylic acid ester of a (C8-C12)fatty alcohol), a (C8-C22)mono- or poly-unsaturated fatty alcohol ester of a (C2-C8)hydroxycarboxylic acid (also often referred to as a (C2-C8)hydroxycarboxylic acid ester of a (C8-C22)mono- or poly-unsaturated fatty alcohol), or alkoxylated derivatives thereof. The alkoxylated derivatives have less than 5 moles of alkoxide per mole of polyhydric alcohol or hydroxy acid. The hydroxycarboxylic acid moiety can include aliphatic and/or aromatic groups. For example, fatty alcohol esters of salicylic acid are possible.

As used herein the term "fatty" refers to alkyl and alkylene hydrocarbon chains of odd or even number of carbon atoms from C6-C18. As used herein, a "fatty alcohol" is an alkyl or alkylene monofunctional alcohol having an even or odd number of carbon atoms and a "fatty acid" is an alkyl or alkylene monofunctional carboxylic acid having an even or odd number of carbon atoms.

Multivalent cationic antiseptic compositions may have a persistently bitter taste. Anionic sweeteners, such as sodium saccharin, previously found to precipitate multivalent cationic actives such as chlorhexidine gluconate, octenidine, and PHMB, can now be used at significantly higher levels than previously known with a multivalent cationic antiseptic to mask this undesirable taste. Levels of anionic compounds as high as 0.1, 0.2, 0.5, 1, or even 2 wt-%, based upon the total weight of the ready to use composition may now be used.

Precipitating anionic compounds which may be used in the present compositions include any anionic compound which precipitates the multivalent cationic antiseptic in the absence of, but not in the presence of an effective amount of the precipitation-preventing or reversing (solubilizing) surfactant. Whether or not a given anionic compound forms a precipitate with the multivalent cationic antiseptic can be readily determined using Test Method A described below. The anionic compound must have a sufficient solubility in the composition so as to remain dissolved and not form a precipitate simply by itself coming out of solution (i.e. the anionic compound should be soluble in the composition with the cationic antiseptic removed). In certain embodiments, preferably the anionic compound is soluble in water in an amount of at least 0.1 gram, more preferably at least 0.2, 0.5, or 1 gram, and most preferably at least 2 or 5 grams in 100 grams water at 23° C. The hydrophobicity of the anion may also determine the anion's ability to precipitate cationic antiseptics. For example, a more hydrophobic anionic compound may more readily precipitate the cationic antiseptic. Similarly, the charge also may affect the ability to precipitate cationic antiseptics. Polyanionic anions appear to result in precipitation which is more difficult to prevent or retard.

The anionic compound may have one, two, or many anionic groups, and each anionic group may have one or two negative charges. For example, carboxylate and sulfonate groups have a single negative charge at the appropriate pH whereas a phosphate group may have one or two negative charges depending on the degree of substitution and the pH. The anionic compound may be a polymeric compound containing a negative charge on some or all pendant groups. Some polymeric anionic compounds may very readily form a precipitate, even at low levels and with small amounts of the multivalent cationic antiseptic.

Representative precipitating anionic compounds include, but are not limited to, anionic sweeteners, anionic dyes, anionic polymers having an acid equivalent weight greater than 400 grams/equivalent, phosphate salts, bicarbonate salts, and combinations thereof. Examples of anionic sweeteners include salts of saccharin (ortho sulfobenzamide), acesulfame (6-methyl-1,2,3-oxathiazine-4(3H)-one-2,2-dioxide), aspartame (dipeptide of aspartic acid and phenylalanine methyl ester), and cyclamate (N-cyclohexylsulfamate), such as their sodium or potassium salts.

Anionic dyes include those having one or more —S(O)$_3^-$, —C(O)$_2^-$, or ≡C—O$^-$ (where ≡ represents three separate C—C bonds) anionic groups or combinations thereof. Examples of anionic dyes include anionic FD &C dyes such as allura red, acid yellow 24 (martius yellow), eosin Y (acid red 87), acid red 66 (biebrich scarlet), and acid fuchsin (acid violet 19). For certain embodiments, the anionic dye is a salt. For certain embodiments, the anionic dye has up to two anionic groups.

Preferred anionic polymers are anionic cellulosic thickeners. Anionic cellulosic thickeners include, for example, salts of carboxymethyl cellulose, xanthan gum, pectin, carrageenan, and alginic acid. Additional anionic thickeners include anionic acrylate or methacrylate polymers having a sufficiently high acid equivalent weight, for example, much higher than the acid equivalent weight of CARBOPOL 954, which is believed to be less than 100 g/equivalent.

Examples of phosphate salts include dihydrogen phosphate salts, hydrogen phosphate salts, alkyl and dialkyl phosphate salts (which may act as surfactants), and the like. The bicarbonate salts as well as any of the above salts may be formed with a sodium or potassium cation.

As used herein, a surfactant is a molecule having at least one hydrophilic region and at least one hydrophobic region and is capable of forming micelles in deionized water. The solubilizing surfactants preferably have a molecular weight of less than 5000 daltons and preferably less than 3000, 2000, and even less than 1000 daltons.

The pH of the compositions can be relevant to formulation stability. For example, certain antiseptics will be cationic (positively charged) when protonated, such as salts of chlorhexidine. Thus, the pH is preferably less than 10 and more preferably less than 9 and most preferably less than 8. Certain surfactants such as zwitterionic and amine oxide surfactants may be subject to protonation. Thus, the pH is preferably greater than 2 and more preferably greater than 3 and most preferably greater than 4. Furthermore, the anionic components also can be protonated. In order to keep these in their anionic form (as opposed to the protonated nonionic form) the pH should be greater than the pKa of the anionic compound. For example, sodium saccharin has a pKa of about 2 but organic carboxylic acids such as those on carboxymethyl cellulose have pKa values of about 3-5. Thus, in general, the pH should be greater than 2, preferably greater than 3, more preferably greater than 4 and most preferably greater than 5.

Surfactants suitable for use as the solubilizing or precipitation-preventing surfactant are selected from the group consisting of zwitterionic surfactants (other than lecithin), amine oxide surfactants, micelle-forming nonionic surfactants, and combinations thereof.

Examples of zwitterionic surfactants include those containing quaternary amine groups, such as the following:

Ammonium Carboxylate Amphoterics—

This class of surfactants can be represented by the following formula:

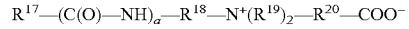

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amido, or amino groups; $R^{19}$ is H, a (C1-C8)alkyl group (saturated straight, branched, or cyclic group), optionally substituted with one or more N, O, or S atoms, or one or more hydroxyl, carboxyl, or amino groups, a (C6-C9)aryl group, or a (C6-C9)aralkyl or alkaryl group; and $R^{18}$ and $R^{20}$ are each independently a (C1-C10) alkylene group that may be the same or different and may be optionally substituted with one or more N, O, or S atoms, or one or more hydroxyl or amino groups.

More preferably, in the formula above, $R^{17}$ is a (C10-C18)alkyl group, $R^{19}$ is a (C1-C2)alkyl group or benzyl group and most preferably a methyl group. When $R^{19}$ is H it is understood that the surfactant at higher pH values could exist as a tertiary amine with a cationic counterion such as Na, K, Li, or an organic amine.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1 L, MACKAM 2L, and MACKAM 151L, respectively, from McIntyre Group Ltd.).

Ammonium Sulfonate Amphoterics—

This class of amphoteric surfactants is often referred to as "sultaines" or "sulfobetaines" and can be represented by the following formula

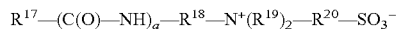

$$R^{17}-(C(O)-NH)_a-R^{18}-N^+(R^{19})_2-R^{20}-SO_3^-$$

wherein $R^{17}$-$R^{20}$ and "a" are defined above. Examples include cocamidopropylhydroxysultaine (commercially available as MACKAM 50-SB from McIntyre Group Ltd.). At low pH, the sulfoamphoterics may be preferred over the carboxylate amphoterics since the sulfonate group will remain ionized at much lower pH values.

For certain embodiments, preferably the zwitterionic surfactant is selected from the group consisting of (C8-C22) alkyl and alkenyl betaines, (C8-C22)aralkyl betaines, (C8-C22)alkaryl betaines, (C8-C22) alkyl and alkenyl sultaines, (C8-C22)aralkyl sultaines, (C8-C22)alkaryl sultaines, and combinations thereof, each of which is unsubstituted or substituted or interrupted at one or more carbon atoms by one or more N-, O-, or S-containing groups. For certain of these embodiments, the zwitterionic surfactant is selected from the group consisting of (C8-C22)alkyl betaines and (C8-C22)alkyl sultaines, and a combination thereof, each of which is unsubstituted or substituted or interrupted at one or more carbon atoms by one or more N-, O-, or S-containing groups. Preferably, for certain embodiments, N-, O-, or S-containing groups are amido, ester, or hydroxyl groups. For certain embodiments, the zwitterionic surfactant is a (C8-C22)alkylamido(C2-C4)alkyl betaine, a (C8-C22)alkylamido(C2-C4)alkylhydroxy sultaine, or a combination thereof. For certain embodiments, the zwitterionic surfactant is a (C8-C22)alkylamidopropyl betaine, a (C8-C22)alkylamidopropylhydroxy sultaine, or a combination thereof.

For certain embodiments, the surfactant is an amine oxide. Examples of amine oxide surfactants, including alkyl and alkylamidoalkyldialkylamine oxides, may be represented by the following formula:

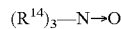

$$(R^{14})_3-N\rightarrow O$$

wherein $R^{14}$ is a (C1-C30)alkyl group (preferably a (C1-C14)alkyl group), a (C6-C18)aralkyl, a (C6-C18)alkaryl group or a combination thereof, wherein any of these groups can be optionally substituted in or on the chain by N-, O-, or S-containing groups such as amido, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. For certain embodiments, the amine oxide surfactant is selected from the group consisting of (C8-C22)alkyldi(C1-C4)alkylamine oxides, (C8-C22)aralkyldi(C1-C4)alkylamine oxides, (C8-C22)alkaryldi(C1-C4)alkylamine oxides, (C8-C22)alkylamido(C2-C4)alkylenyldi(C1-C4)alkylamine oxides, (C8-C22)aralkylamido(C2-C4)alkylenyldi(C1-C4)alkylamine oxides, (C8-C22)alkarylamido(C2-C4)alkylenyldi(C1-C4) alkylamine oxides, and combinations thereof. Preferably, two $R^{14}$ groups are (C1-4)alkyl, for example, methyl. Preferably one $R^{14}$ group is a (C12-C16)alkyl or (C12-C16) alkylamidopropyl group. For certain of these embodiments, the amine oxide is a (C12-C16)alkylamidopropyl(C1-C4) dialkyl amine oxide, for example, a (C12-C16)alkylamidopropyldimethylamine oxide. Examples of amine oxide surfactants include those commercially available under the trade designations AMMONYX LO, LMDO, and CO, which are lauryldimethylamine oxide, laurylamidopropyldimethylamine oxide, and cetyldimethylamine oxide, all from Stepan Company of Northfield, Ill.

For certain embodiments, the solubilizing surfactant is selected from the group consisting of a (C8-C22)alkylamidopropylbetaine, a (C12-C16)alkylamidopropyldimethylamine oxide, and a combination thereof.

For certain embodiments, the solubilizing surfactant is a micelle-forming nonionic surfactant. Examples of such surfactants include, but are not limited to, (C8-C22) alkyl, alkaryl, and aralkyl glucosides and polyglucosides (e.g., alkyl mono and oligo glucopyranoside available under the trade name Glucopon 225DK from BASF Corp., Florham Park, N.J.); esters of fatty acids such as polyglycerol and poly(oxyethylene) esters of fatty acids (e.g., polyglycerol-10 myristate available under the trade name Decaglyn from Barnet Products Corporation, Englewood Cliffs, N.J., and poly(oxyethylene) sorbitan esters (e.g., poly(oxyethylene) (20) sorbitan monolaurate available under the trade name Tween 20 from Croda Inc., Edison, N.J., and poly(oxyethylene) (40) sorbitan diisostearate available under the trade name Canarcel from Quimica Delta, Teoloyucan, MX); (C8-C22) alkyl, alkaryl, and arylalkyl poly(oxyethylene) ethers (e.g., poly(oxyethylene) octadecyl ether available under the trade name Brij 78 from Sigma-Aldrich, St. Louis, Mo., octyl phenoxy polyethoxyethanol available under the trade name TRITON X-100 and nonyl phenoxy poly(ethyleneoxy) ethanol available under the trade name NONIDET P-40, both from Sigma-Aldrich, St. Louis, Mo.).

For certain embodiments, the micelle-forming nonionic surfactant may be selected from the group consisting of (C8-C22)alkyl glucosides, (C8-C22)alkaryl glucosides, (C8-C22)aralkyl glucosides, poly(oxyethylene) sorbitan fatty acid esters, (C8-C22) alkyl and alkenyl poly(oxyethylene) esters, (C8-C22)alkaryl poly(oxyethylene) esters, (C8-C22)aralkyl poly(oxyethylene) esters, (C8-C22) alkyl and alkenyl poly(oxyethylene) ethers, (C8-C22)alkaryl poly (oxyethylene) ethers, (C8-C22)aralkyl poly(oxyethylene) ethers, polyglycerol (C8-C22)alkyl ethers, polyglycerol (C8-C22)fatty acid esters, and combinations thereof. As used herein "fatty" refers to even or odd number of carbon atoms, branched or straight chain.

For certain embodiments, the micelle-forming nonionic surfactant is a (C8-C22)alkyl glucoside.

For certain embodiments, the micelle-forming nonionic surfactant is a poly(oxyethylene) sorbitan fatty acid ester.

For certain embodiments, the micelle-forming nonionic surfactant is a poly(oxyethylene) sorbitan fatty acid diester.

For certain embodiments, the micelle-forming nonionic surfactant is a polyglycerol (C8-C22)fatty acid ester.

For certain embodiments, the micelle-forming nonionic surfactant is a (C8-C22)alkyl poly(oxyethylene) ether.

Any of the surfactants herein comprising an alkyl, alkaryl, or arylalkyl group having eight to twenty-two carbon atoms (C8-C22) preferably comprises the alkyl, alkaryl, or arylalkyl group having twelve to eighteen carbon atoms (C12-C18). Esters of fatty acids are preferably esters of (C12-C18) fatty acids. Poly(oxyethylene), PEG, and polyethylene glycol are used interchangeably to indicate repeating units of —$CH_2CH_2$—O—. When present on the surfactant molecule (e.g., on a PEG 20 sorbitan monoester), preferably at least 5, more preferably at least 10, and most preferably at least 20 repeating units are present. Preferably, not more than 70, 60, 50, or 40 repeating units are present. In addition, units of propylene oxide may be present as well in amounts generally less than about 50, preferably less than 30 and most preferably less than 15 units.

Many commercially available surfactants are actually comprised of a mixture of surfactants. The chain lengths of the hydrophobe can vary as well as the length of hydrophilic head groups such as polyalkoxylates and polyglucosides. For example, some surfactants based on coconut oil derived alcohol as commercially supplied are actually a mixture of alkyl alcohols consisting of primarily C12 and C14 fractions but contain detectable levels of C8-18 fractions. For this reason, the chain lengths specified herein refer to the number average chain length. When concentrations of the surfactants are specified it is understood that this represents the collective amount of surfactants of the type specified.

Although certain surfactants when used at excessively high concentrations can reduce the activity of multivalent cationic antiseptics such as CHG, applicants have found a balance between losing activity of the antiseptic caused by excess surfactant and losing activity of the antiseptic caused by precipitation with the anionic compound. As a result, antiseptic efficacy is achieved in the presence of the combination of the surfactant and the anionic compound.

The solubilizing surfactant is present in the compositions in a sufficient amount to prevent precipitation of the multivalent cationic antiseptic by the anionic compound, the anionic compound being present in an amount which would precipitate the antiseptic, absent the solubilizing surfactant. For certain embodiments, for example, when the composition is aqueous without other solvents, preferably the solubilizing surfactant is present in an amount of less than 2%, more preferably less than 1%, and most preferably less than 0.5%, based upon the total weight of the ready to use composition. When other solvents, such as lower alcohols or other hydrophilic components, are present, these amounts may be higher.

The amounts of these three components (i.e., the amount of the solubilizing surfactant, the amount of the anionic compound, and the amount of the multivalent cationic antiseptic) can be conveniently expressed as the weight percent (wt-%) of each of these components with respect to each other, based upon the combined weight of all three of these components. For example, when the composition contains 2% solubilizing surfactant, 0.2% anionic compound, and 0.24% multivalent cationic antiseptic (based upon the total weight of the ready to use composition), the amount of the three components with respect to each other is 82%, 8.2%, and 9.8%, respectively. This is calculated by dividing the amount of each component by the sum of the amounts of the three components. For example, 2%+0.2%+0.24%=2.44%, and 2/2.44(100)=82%, 0.2/2.44(100)=8.2%, and 0.24/2.44(100)=9.8%.

The amounts of the three components with respect to each other can be plotted to form a phase diagram showing where precipitation occurs and where precipitation does not occur. In this way, the relative amounts of the three components providing a composition without precipitation can readily be determined. In one embodiment, taking into account all of the representative anionic compounds, surfactants, and multivalent cationic antiseptics tested, this condition is met with less than 20% anionic compound, greater than 80% solubilizing surfactant, and not more than 11, 10.5, or 10% multivalent cationic antiseptic. For certain embodiments, the amounts of the three components with respect to each other are not more than 18.5% or 10% anionic compound, greater than 80%, 81%, or 82% solubilizing surfactant, and less than 11, 10.5, or 10% multivalent cationic antiseptic. For certain of these embodiments where the anionic compound is an anionic sweetener, the amounts of the three components with respect to each other are less than 35% anionic sweetener, more than 63.9% solubilizing surfactant, and not more than 27% multivalent cationic antiseptic.

Referring to FIGS. 1 through 19, each of these figures is a three-component phase diagram wherein the amounts of the three components (anionic compound, solubilizing surfactant, and multivalent cationic antiseptic) at 0 to 100% relative to the sum of all three are plotted. Areas in the diagrams where the three components are at levels relative to each other which provide clear solutions without precipitate are shown by shading with open circles. The open circles represent specific compositions found in the Examples. The vertices of these areas, whether an inside or an outside corner or inflexion, are points labeled with a letter along with the figure number (e.g., A1, B1, C1 in FIG. 1) In some instances, the vertex is one of the specific tested compositions.

Figure 14:
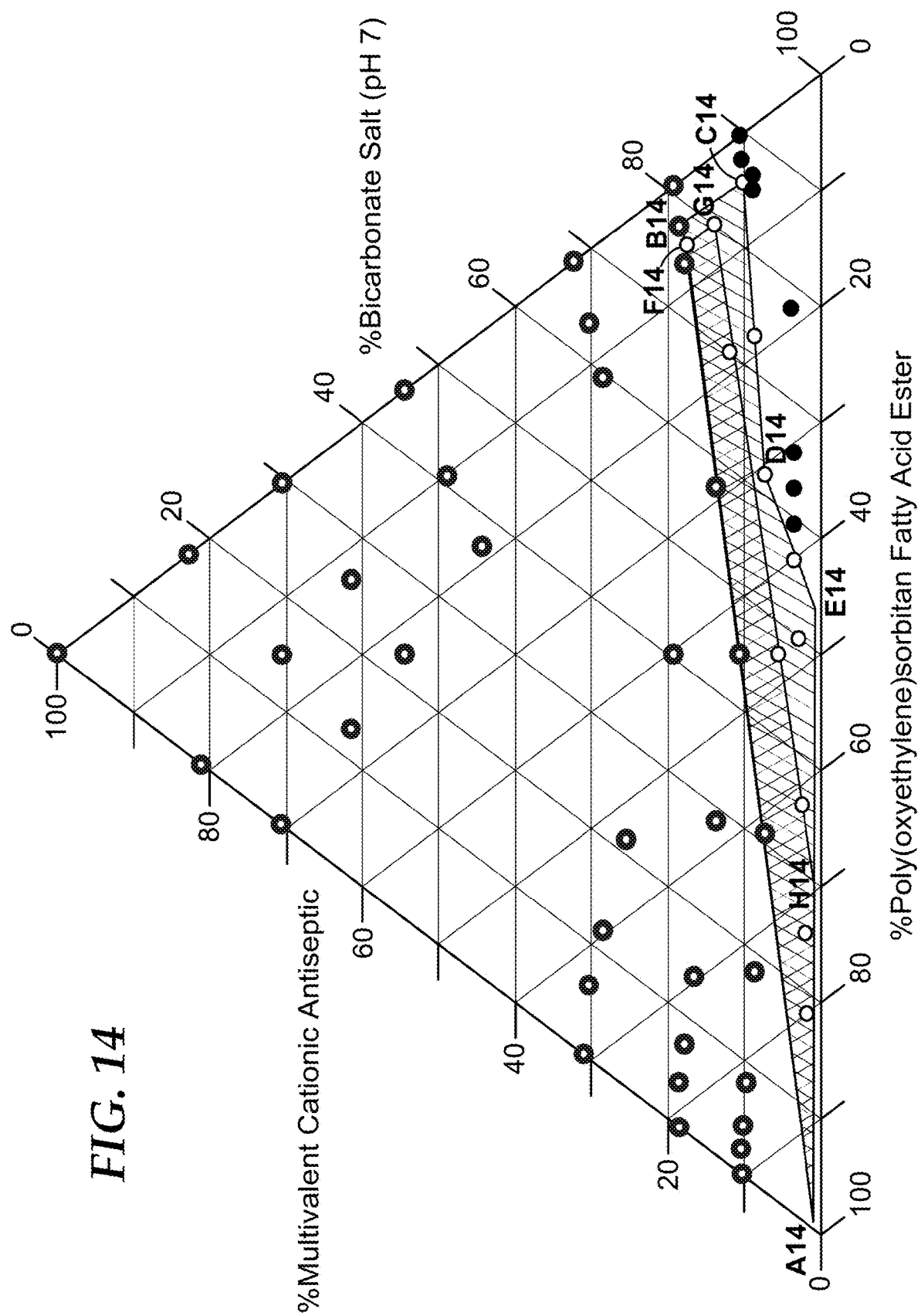
FIG. 14 is a phase diagram of % multivalent cationic antiseptic, % bicarbonate salt at a pH of about 7, and % poly(oxyethylene)sorbitan fatty acid ester surfactant, showing regions without and with precipitate.
Figure 15:
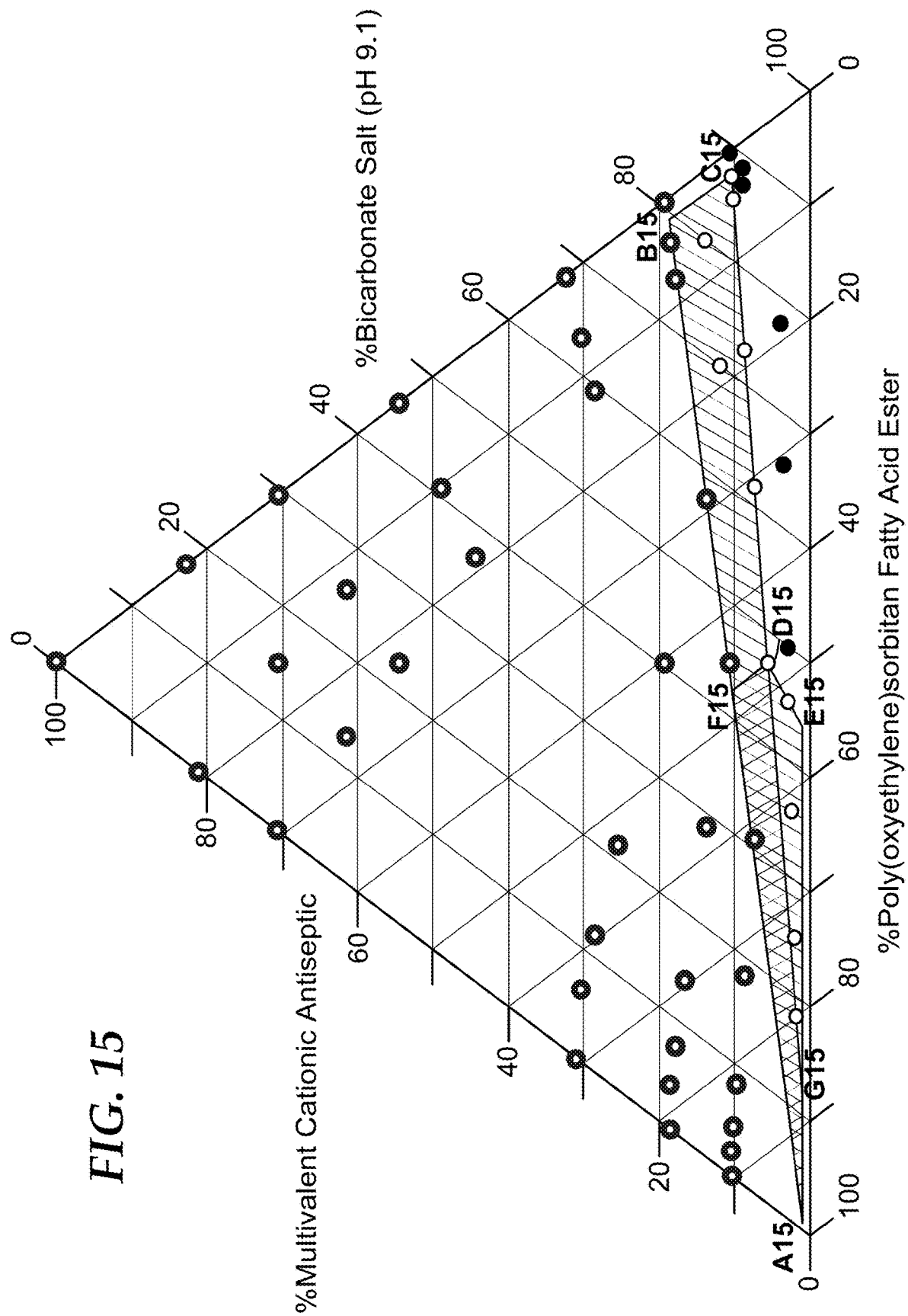
FIG. 15 is a phase diagram of % multivalent cationic antiseptic, % bicarbonate salt at a pH of about 9.1, and % poly(oxyethylene)sorbitan fatty acid ester surfactant, showing regions without and with precipitate.
Figure 16:
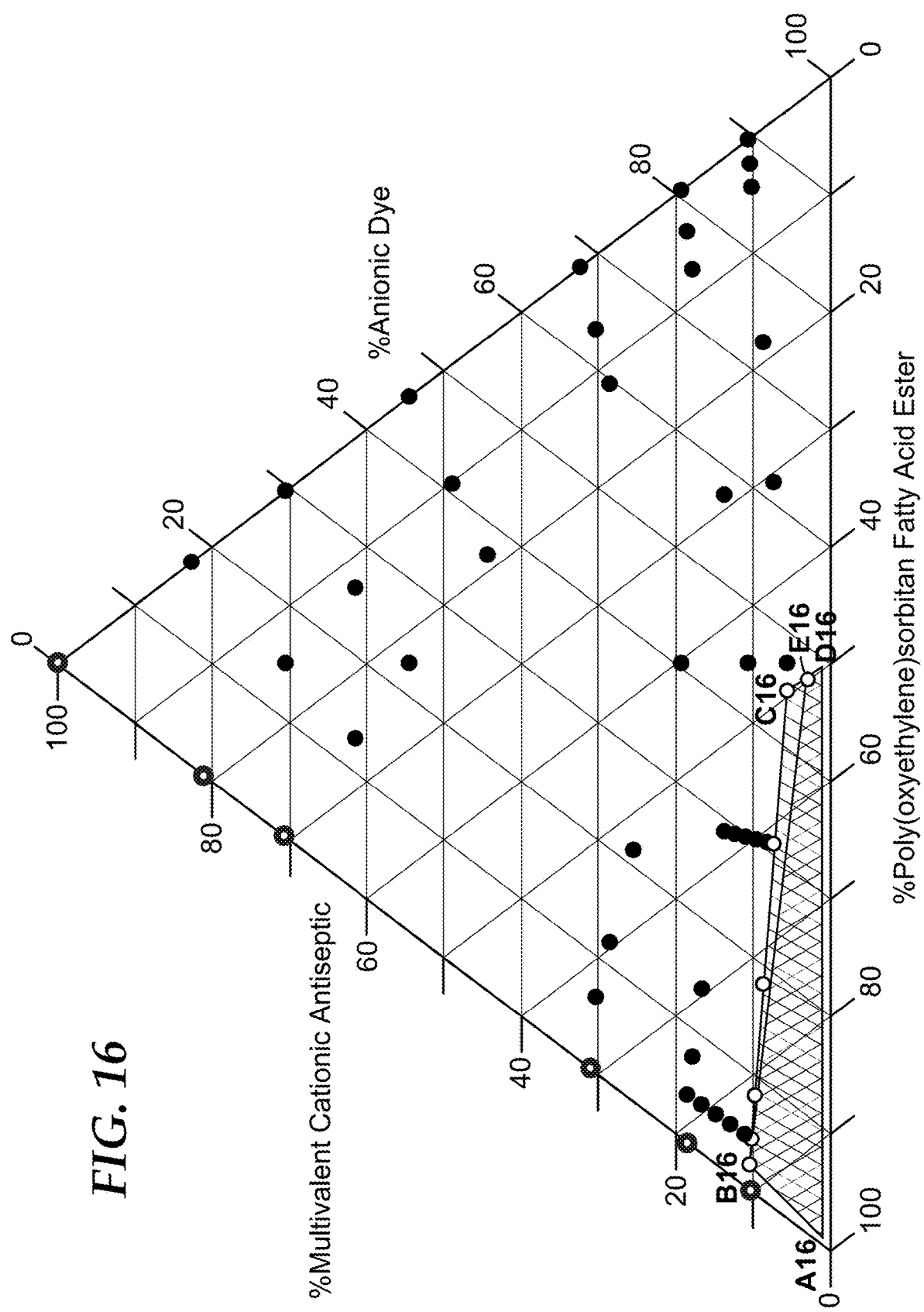
FIG. 16 is a phase diagram of % multivalent cationic antiseptic, % anionic dye, and % poly(oxyethylene)sorbitan fatty acid ester surfactant, showing regions without and with precipitate.
Figure 17:
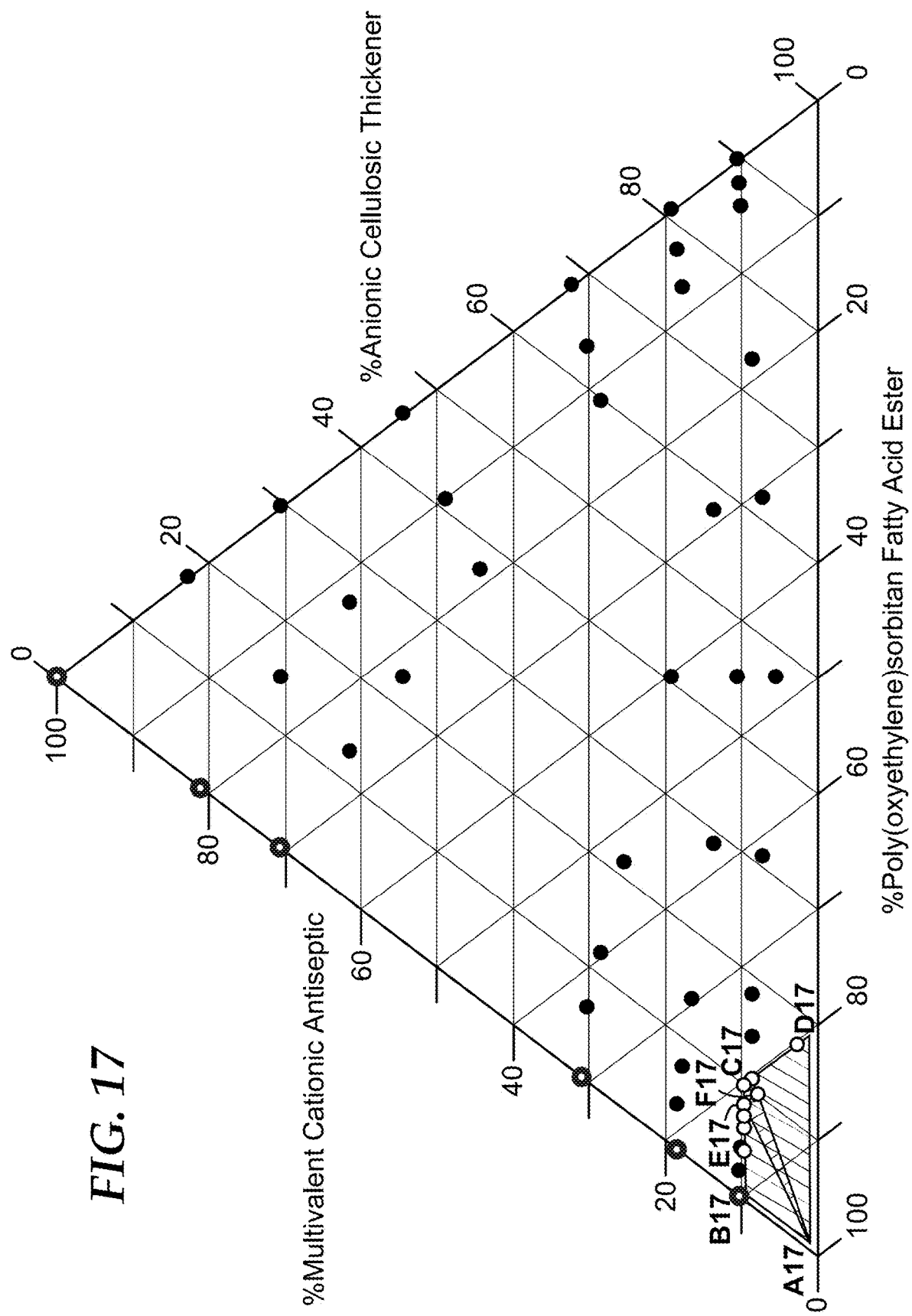
FIG. 17 is a phase diagram of % multivalent cationic antiseptic, % anionic cellulosic thickener (at pH above 7), and % poly(oxyethylene)sorbitan fatty acid ester surfactant, showing regions without and with precipitate.

Referring to FIG. 1, a phase diagram is provided showing areas without and with precipitate based upon the relative amounts of anionic sweetener, solubilizing surfactant, and multivalent cationic antiseptic. This takes into account all of the representative anionic sweetener, surfactants, and multivalent cationic antiseptics represented by CHG tested. This is essentially a composite of FIGS. 5, 7, 9, and 11, forming the area representing precipitate-free compositions. In FIG. 1, the area defined by the bold open circles represents compositions without precipitate, whether or not the solubilizing surfactant is present. That is, even if the solubilizing surfactant were removed, there would be no precipitate. The bold open circles, therefore, identify a ratio of anionic compound to cationic antiseptic above which precipitation will occur. Here and in FIGS. 2-11 and 18 where the anionic compound is an anionic sweetener and in FIGS. 12-13 where the anionic compound is a phosphate salt this ratio is about 0.21. In FIGS. 14-15 where the anionic compound is a bicarbonate salt this ratio is about 4.2. In FIGS. 16-17 where the anionic compound is an anionic thickener or anionic dye, any amount of the anionic compound causes a precipitate, the ratio being any number above 0. In FIG. 19 where the multivalent cationic antiseptic is octenidine, any amount of the anionic compound, such as an anionic sweetener, causes a precipitate, the ratio also being any number above 0. The shaded area including the open circles represents compositions without precipitate because of the presence of the solubilizing surfactant. The area including the solid circles represents compositions with a precipitate.

In FIGS. 1-19, points A1-A19 all represent 1.2% multivalent cationic antiseptic, 1.2% anionic compound, and 97.6% solubilizing surfactant, based upon the total amounts of these three components. These constitute the minimum amounts of multivalent cationic antiseptic and anionic compound and maximum amount of solubilizing surfactant contemplated, relative to the total amounts of these three components. Consistent with the present findings, no precipitate is expected at points A1-A19, since no precipitate was found at lower solubilizing surfactant levels and higher anionic compound levels.

In FIGS. 1-15 and 18, the points B1-B15 and B18 are established by the intersection of a straight line running through the bold open circles and a straight line running from the respective "C" point, keeping the solubilizing surfactant level constant and reducing the amount of anionic compound. In FIG. 17, the point B17 is established by a straight line running from the open circle at the highest surfactant and lowest anionic compound levels to 1.2% anionic compound, keeping the % multivalent cationic antiseptic constant.

Figure 5:
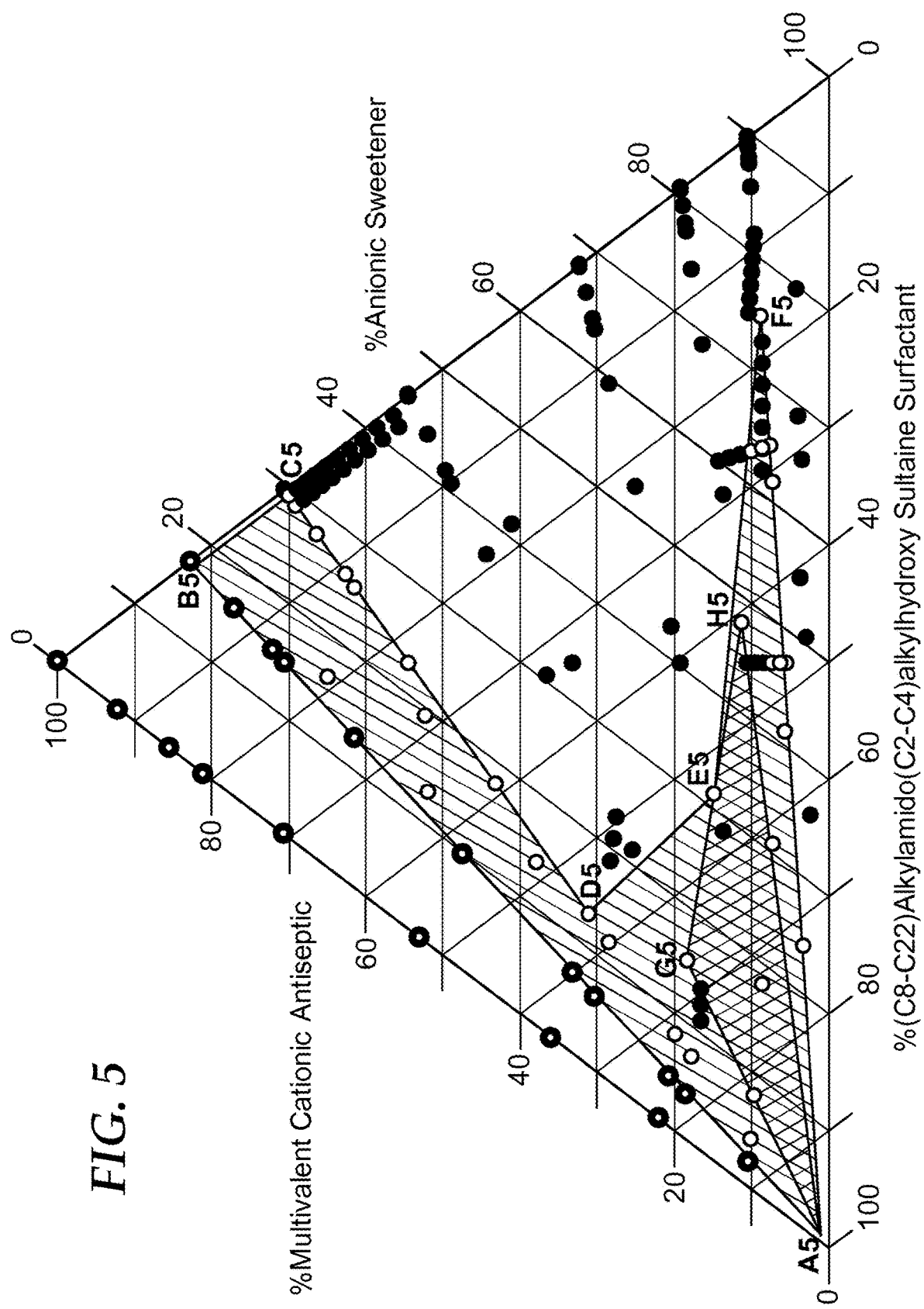
FIG. 5 is a phase diagram of % multivalent cationic antiseptic, % anionic sweetener, and % (C8-C22)alkylamido (C2-C4)alkylhydroxy sultaine surfactant, showing regions without and with precipitate.
Figure 6:
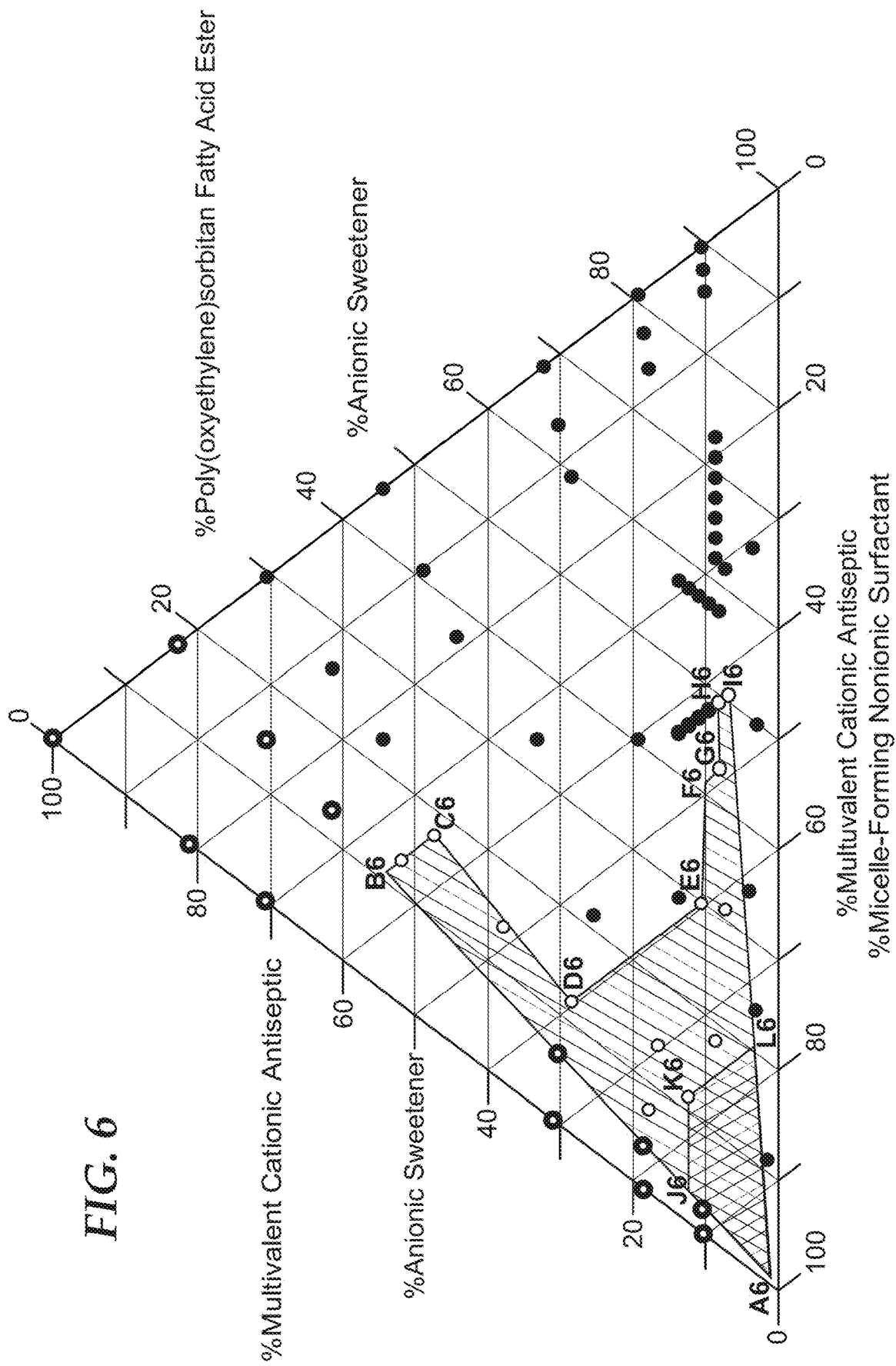
FIG. 6 is a composite phase diagram of % multivalent cationic antiseptic, % anionic sweetener, and % micelle-forming nonionic surfactant, showing regions without and with precipitate.

In FIGS. 1 and 6, the points K1 and L6 are established by a straight line running from the longer term precipitate-free composition having the lowest level of solubilizing surfactant, keeping the amount of solubilizing surfactant constant, to the boundary line A1-I1 in FIG. 1 and the boundary line A6-I6 in FIG. 6. This is supported by the longer term precipitate-free compositions found as shown, for example, in FIGS. 3, 4, 5, and 11.

Figure 11:
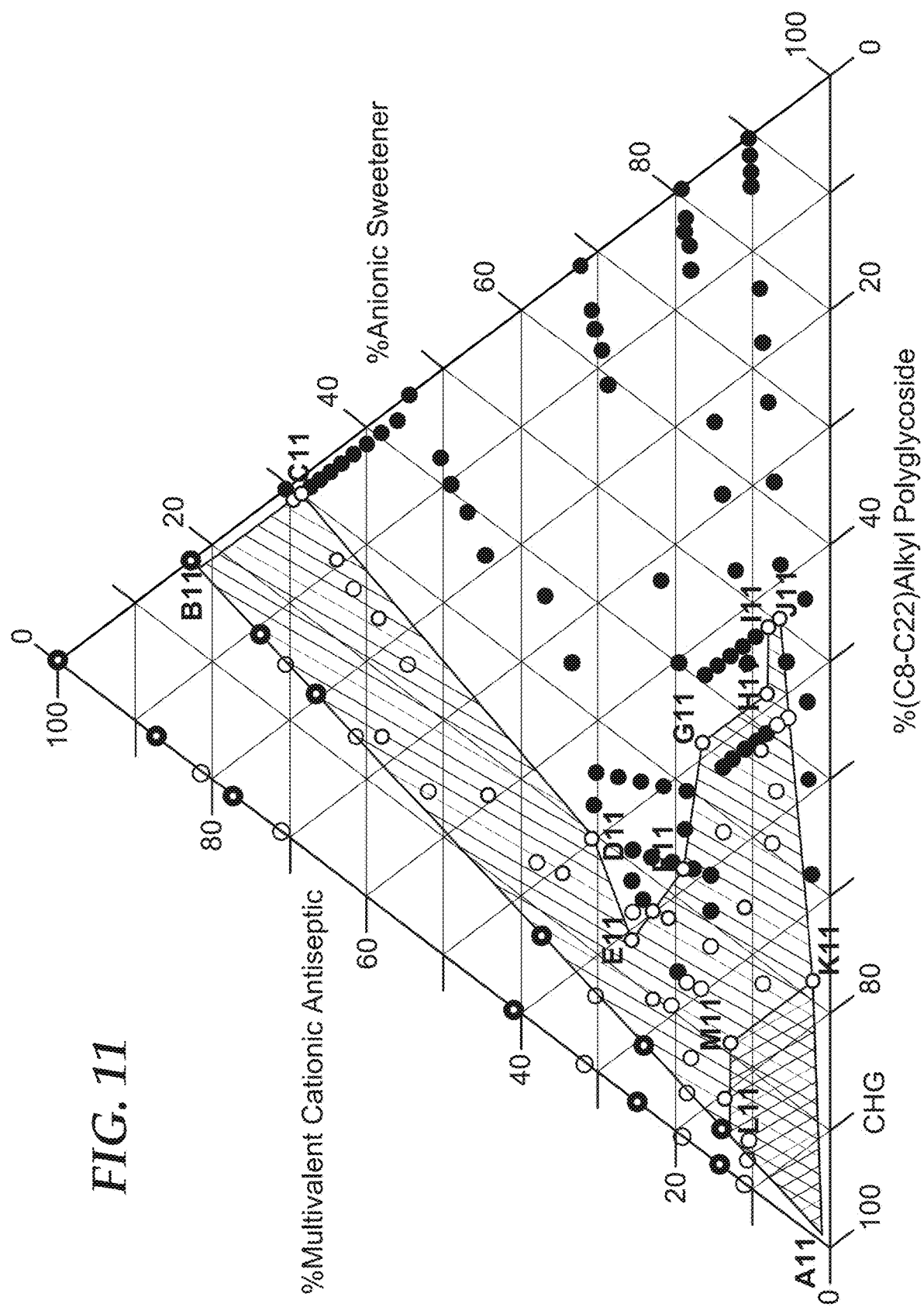
FIG. 11 is a phase diagram of % multivalent cationic antiseptic, % anionic sweetener, and % (C8-C22)alkyl polyglycoside surfactant, showing regions without and with precipitate.

In FIGS. 6 and 11, points J6 and L11 (under the bold open circle) are established by a straight line running from the open circle at the highest surfactant level and lowest anionic compound level found to have longer term stability to 1.2% anionic compound, keeping the multivalent cationic antiseptic level constant.

Figure 12:
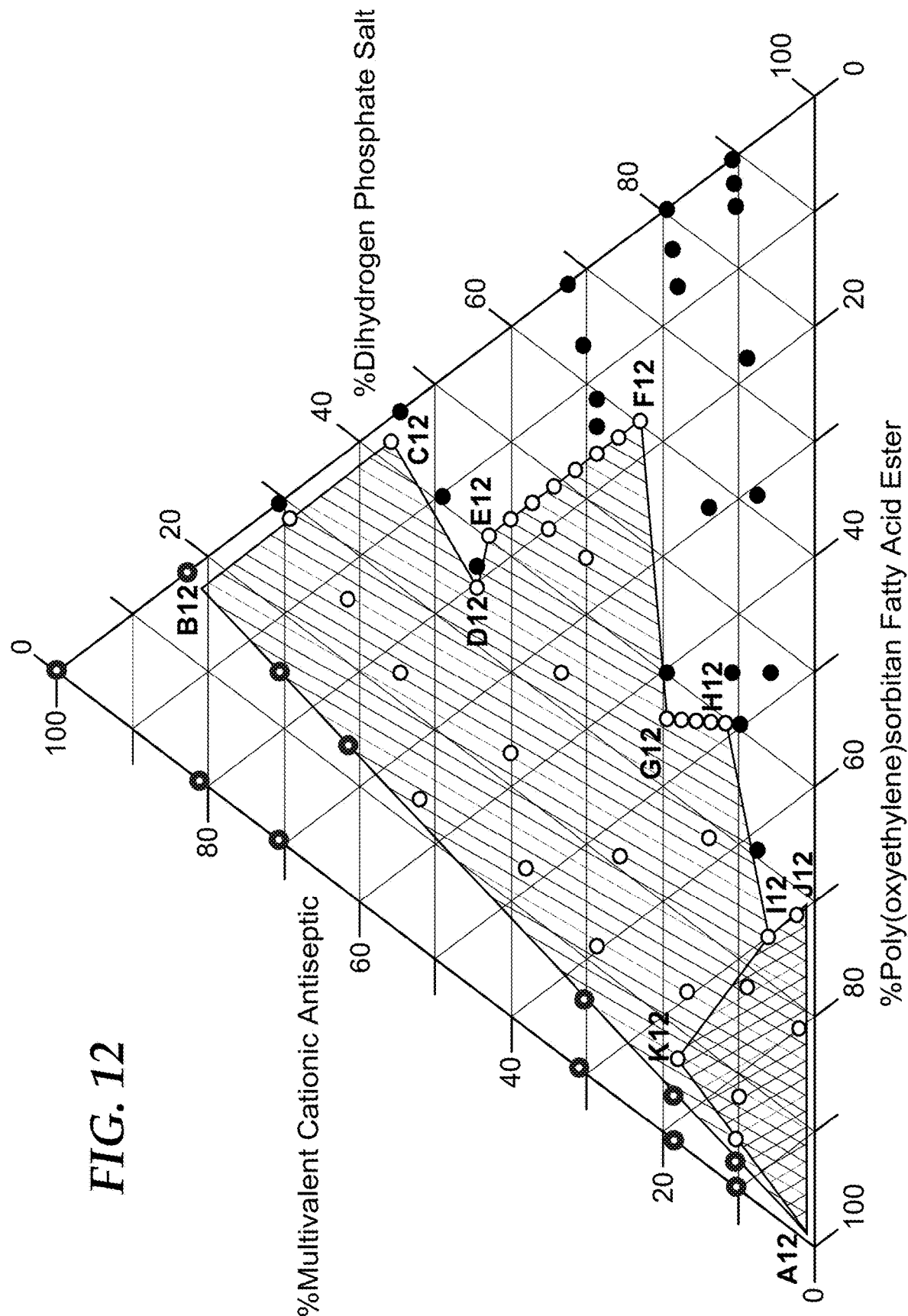
FIG. 12 is a phase diagram of % multivalent cationic antiseptic, % dihydrogen phosphate salt, and % poly(oxyethylene)sorbitan fatty acid ester surfactant, showing regions without and with precipitate.

In FIGS. 16, 17, and 19, the points D16, D17, and D19 are established by a straight line running from the open circle representing the composition with the lowest level of multivalent cationic antiseptic to 1.20% multivalent cationic antiseptic, while keeping the level of solubilizing surfactant constant. In FIG. 12, the point J12 is established by a straight line running from the open circle labeled I12 through the closest open circle with a lower level of multivalent cationic antiseptic to 1.2% multivalent cationic antiseptic, keeping the level of solubilizing surfactant constant. This is support by the close proximity of these points to an open circle (data point).

In FIGS. 4, 7, 8, 10, 14, 15, and 18, the points H4, J7, K8, H10, E14, H14, E15, G15, and F18 are established by intersecting the straight boundary lines G4-H4, I7-J7, J8-K8, G10-H10, D14-E14, G14-H14, D15-E15, D15-G15, and E18-F18, respectively, with the line representing 1.20% multivalent cationic antiseptic.

For certain embodiments, the anionic sweetener, solubilizing surfactant, and multivalent cationic antiseptic are present in the instant compositions in amounts within the boundary defined by points A1, B1, C1, D1, E1, F1, G1, H1, and I1, and along the boundary lines of B1-C1, C1-D1, D1-E1, E1-F1, F1-G1, G1-H1, H141, and I1-A1 in FIG. 1. The boundary line of A1-B1 is included in the area defined by the bold open circles. The amounts of the three components (% anionic compound/% solubilizing surfactant/% multivalent cationic antiseptic) with respect to each other at each of these points are as follows: A1=1.2/97.6/1.2; B1=11.2/35.0/53.8; C1=17.5/35.0/47.5; D1=11.9/59.5/28.6; E1=29.8/59.5/10.7; F1=41.4/48.6/10.0; G1=43.1/48.6/8.3; H1=48.8/43.0/8.2; and I1=50.3/43.0/6.7.

For certain embodiments, preferably for longer term stability the anionic sweetener, solubilizing surfactant, and multivalent cationic antiseptic are present in the instant compositions in amounts within the boundary defined by points A1, J1, and K1, and along the boundary lines of A1-J1, J1-K1, and K1-A1 in FIG. 1. The amounts of the three components (% anionic compound/% solubilizing surfactant/% multivalent cationic antiseptic) with respect to each other at each of these points are as follows: A1=1.2/97.6/1.2; J1=10.9/76.1/13.0; and K1=20.5/76.1/3.4. For certain of these embodiments, preferably for longer term stability the solubilizing surfactant is selected from the group consisting of (C8-C22) alkyl, alkaryl, and aralkyl glucosides and polyglucosides (e.g., alkyl mono and oligo glucopyranoside available under the trade name Glucopon 225DK from BASF Corp., Florham Park, N.J.), amine oxide surfactants described above, and zwitterionic surfactants described above. For certain of these embodiments, the anionic sweetener is sodium saccharin.

Based upon the phase diagram of FIG. 1, the amounts of the three components with respect to each other may be expressed as follows for the present compositions without precipitate: at least 35% solubilizing surfactant, not more than 18% anionic compound (A), not more than 54% multivalent cationic antiseptic (MCA); and at least 59.5% solubilizing surfactant, less than 30% A, and less than 30% MCA; and at least 48.6% solubilizing surfactant, not more than 43.1% A, less than 11% MCA; at least 43% solubilizing surfactant, not more than 50.3% A, not more than 8.3% MCA, but greater than 1.6% MCA at above 10% A, greater than 3.2% MCA at above 20% A, and greater than 4.1% MCA at above 30% A. For certain of these embodiments, for longer term stability the amounts of the three components are preferably: at least 76% solubilizing surfactant, not more than 20.5% A, and not more than 13% MCA, but greater than 1.6% MCA above 10% A and not more than 6% A at less than 6.7 MCA.

Figure 2:
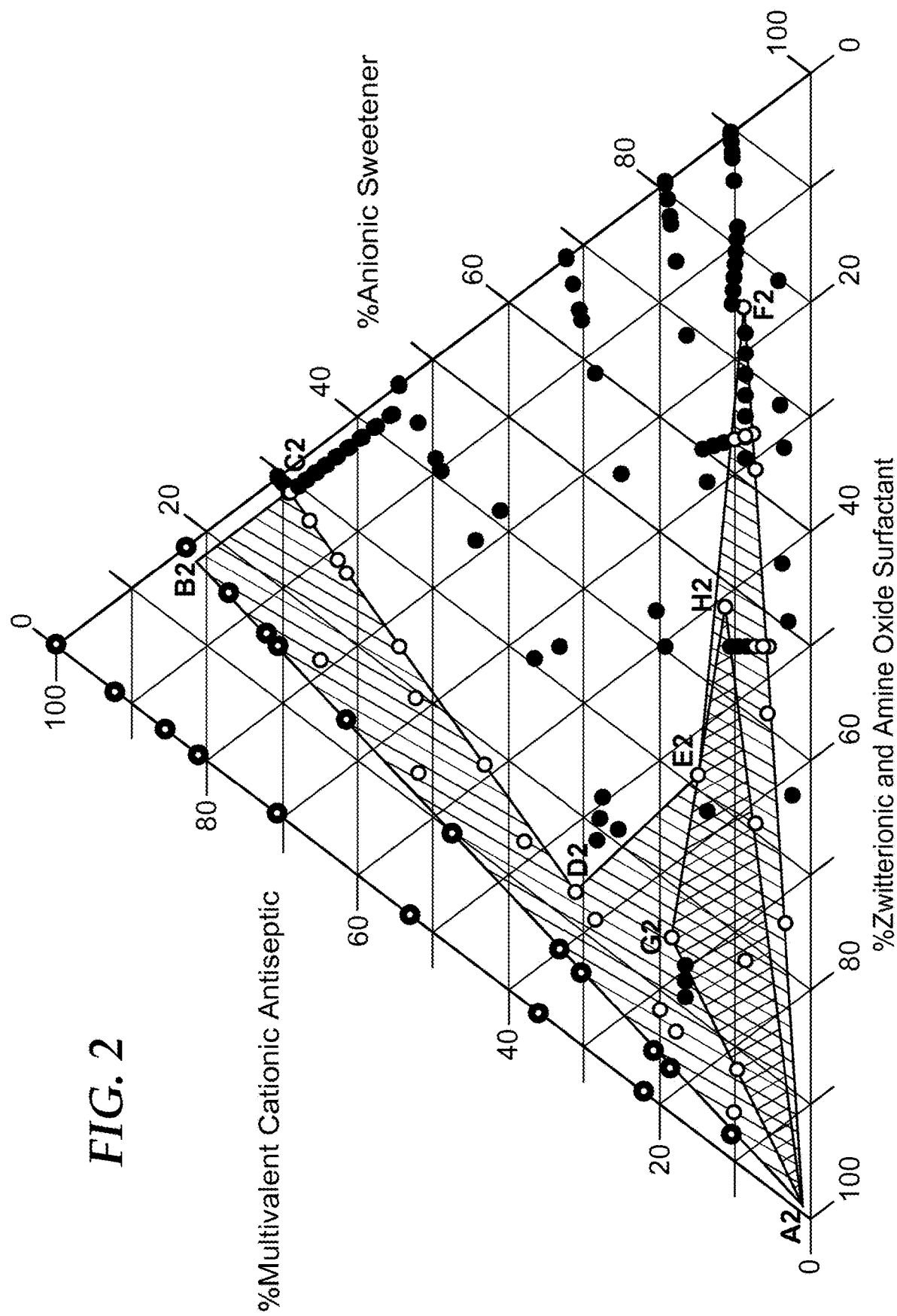
FIG. 2 is a composite phase diagram of % multivalent cationic antiseptic, % anionic sweetener, and % zwitterionic and amine oxide surfactant, showing regions without and with precipitate.

Referring to FIG. 2, a phase diagram is provided showing areas without and with precipitate based upon the relative amounts of anionic sweetener, zwitterionic or amine oxide surfactant, and multivalent cationic antiseptic. This takes into account all of the representative anionic sweetener, zwitterionic and amine oxide surfactants, and multivalent cationic antiseptic represented by CHG tested. This is essentially a composite of FIGS. 4 and 5, forming the area representing precipitate-free compositions. In FIG. 2, the area defined by the bold open circles, the open circles, and the solid circles are as described in FIG. 1. For certain embodiments, the anionic sweetener, zwitterionic and amine oxide surfactants, and multivalent cationic antiseptic are present in the instant compositions in amounts within the boundary defined by points A2, B2, C2, D2, E2, and F2, and along the boundary lines B2-C2, C2-D2, D2-E2, E2-F2, and F2-A2 in FIG. 2. The boundary line A2-B2 is included in the area defined by the bold open circles. The amounts of the three components (% anionic compound/% solubilizing surfactant/% multivalent cationic antiseptic) with respect to each other at each of these points are as follows: A2=1.2/97.6/1.2; B2=16.4/1.9/81.2; C2=28.9/1.9/69.2; D2=13.0/55.8/31.2; E2=31.3/53.7/15.0; and F2=74.9/16.1/9.0.

For certain embodiments, preferably for longer term stability the anionic sweetener, zwitterionic or amine oxide surfactant, and multivalent cationic antiseptic are present in the instant compositions in amounts within the boundary defined by points A2, G2, and H2, and along the boundary lines of A2-G2, G2-H2, and H2-A2 in FIG. 2. The amounts of the three components (% anionic compound/% solubilizing surfactant/% multivalent cationic antiseptic) with respect to each other at each of these points are as follows: A2=1.2/97.6/1.2; G2=15.4/66.2/18.5; and H2=47.6/41.0/11.4.

For certain of these embodiments, the zwitterionic surfactants are selected from the group consisting of (C8-C22) alkyl and alkenyl betaines, (C8-C22)aralkyl betaines, (C8-C22)alkaryl betaines, (C8-C22) alkyl and alkenyl sultaines, (C8-C22)aralkyl sultaines, (C8-C22)alkaryl sultaines, each of which is unsubstituted or substituted or interrupted at one or more carbon atoms by one or more N-, O-, or S-containing groups such as amido, ester, or hydroxyl groups, and the like, and combinations thereof. Applicants have found that preferred zwitterionic surfactants have a single hydrophobic group (long chain alkyl, alkenyl, alkaryl, or aralkyl group). For example, lecithin which predominantly has two hydrophobic groups does not work as well. The reason for this is not clear. For certain of these embodiments, the zwitterionic surfactants are selected from the group consisting of (C8-C22)alkyl betaines and (C8-C22)alkyl sultaines, each of which is unsubstituted or substituted or interrupted at one or more carbon atoms by one or more N-, O-, or S-containing amido, ester, or hydroxyl groups.

For certain embodiments, the amine oxide surfactants are represented by the formula $(R^{14})_3$—N→O wherein $R^{14}$ is a (C1-C14)alkyl, (C2-C14)alkenyl, (C6-C18)aralkyl, or (C6-C18)alkaryl group or a combination thereof, each of which is unsubstituted or substituted or interrupted at one or more carbon atoms by one or more N-, O-, or S-containing groups such as amido, ester, or hydroxyl groups, and the like, and combinations thereof, and wherein each $R^{14}$ may be the same or different, and at least one $R^{14}$ group includes at least eight carbons. For certain of these embodiments, the amine oxide surfactants are selected from the group consisting of (C12-C16)alkyl(C1-C4)dialkylamine oxides, (C12-C16)alkylamido(C2-C4)alkylene(C1-4)dialkylamine oxides, and combinations thereof.

Based upon the phase diagram of FIG. 2, in embodiments wherein the solubilizing surfactant is a zwitterionic or amine oxide surfactant as described above, the amounts of the three components with respect to each other may be expressed as follows for the present compositions without precipitate: at least 1.9% zwitterionic or amine oxide surfactant (Z/AS), less than 29% anionic compound (A), not more than 81.2% multivalent cationic antiseptic (MCA); and at least 40% Z/AS, not more than 18% A, less than 50% MCA; and at least 53% Z/AS, not more than 31.3% A, less than 30% MCA; and at least 35% Z/AS, less than 50% A, less than 15% MCA; and greater than 22% Z/AS, less than 68% A, and not more than 11% MCA, but at least 4.5% MCA at greater than 50% A; and greater than 16% Z/AS, less than 75% A, and less than 10% MCA, but at least 5% MCA at greater than 68% A. For certain of these embodiments, for longer term stability the amounts of the three components are preferably: greater than 40% Z/AS, less than 48% A, and less than 19% MCA, but at last 6% MCA at greater than 30% A.

For certain of these embodiments, the anionic sweetener is sodium saccharin.

For certain of these embodiments, the solubilizing surfactant is the zwitterionic surfactant in any one of the above embodiments. Alternatively, for certain of these embodiments, the solubilizing surfactant is the amine oxide surfactant in any one of the above embodiments.

Figure 3:
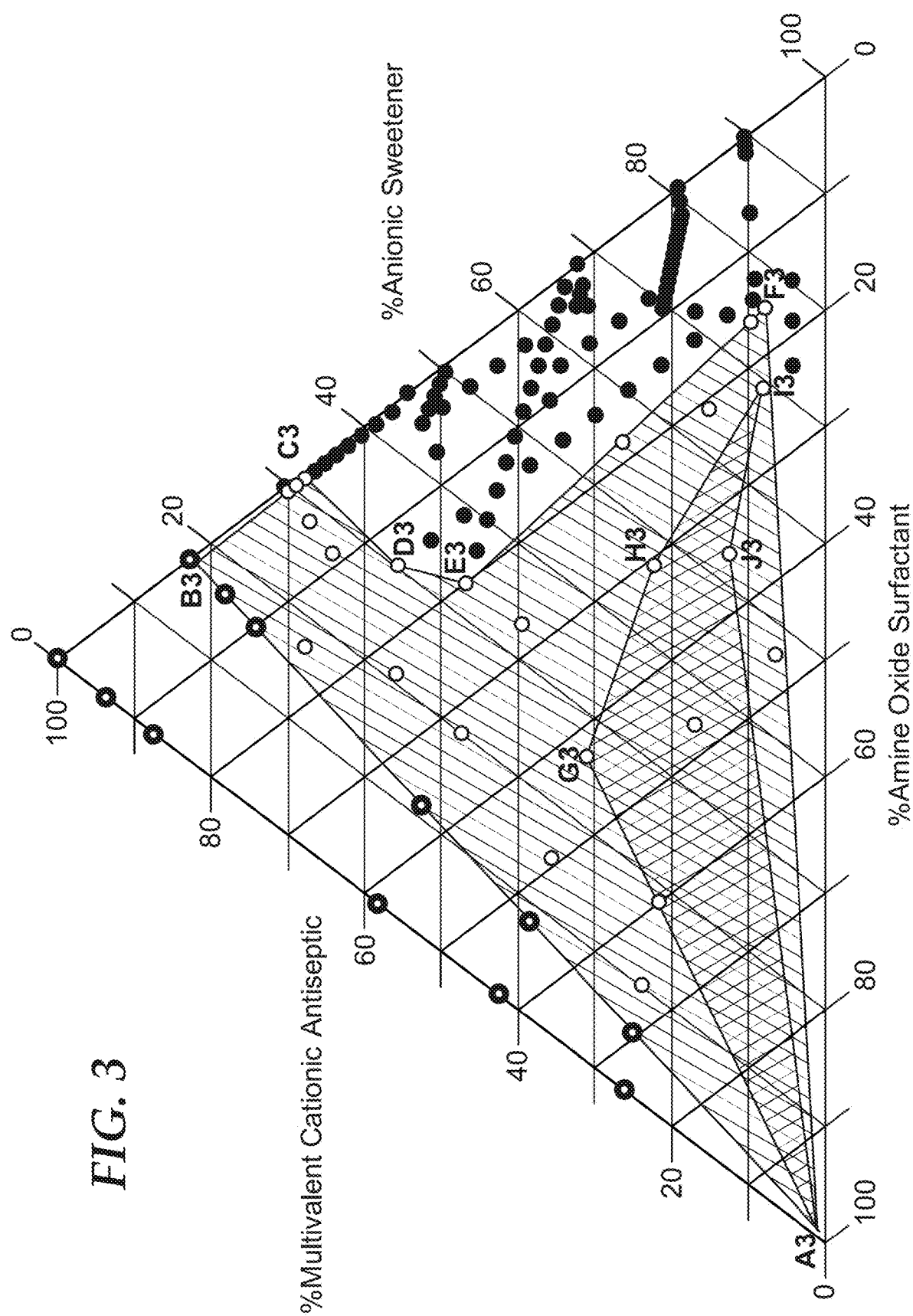
FIG. 3 is a phase diagram of % multivalent cationic antiseptic, % anionic sweetener, and % amine oxide surfactant, showing regions without and with precipitate.

Referring to FIG. 3, a phase diagram is provided showing areas without and with precipitate based upon the relative amounts of anionic sweetener, amine oxide surfactant, and multivalent cationic antiseptic represented by CHG. In FIG. 3, the area defined by the bold open circles, the open circles, and the solid circles are as described in FIG. 1. For certain embodiments, the anionic sweetener, amine oxide surfactant, and multivalent cationic antiseptic are present in the instant compositions in amounts within the boundary defined by points A3, B3, C3, D3, E3, and F3, and along the boundary lines of B3-C3, C3-D3, D3-E3, E3-F3, and F3-A3 in FIG. 3. The boundary line of A3-B3 is included in the area defined by the bold open circles. The amounts of the three components (% anionic compound/% solubilizing surfactant/% multivalent cationic antiseptic) with respect to each other at each of these points are as follows: A3=1.2/97.6/1.2; B3=17.1/0.7/82.2; C3=31.4/0.7/67.9; D3=30.1/14.1/55.8; E3=32.9/20.1/47.0; and F3=76.0/16.0/8.0.

For certain embodiments, preferably for longer term stability the anionic sweetener, amine oxide surfactant, and multivalent cationic antiseptic are present in the instant compositions in amounts within the boundary defined by points A3, G3, H3, I3, and J3, and along the boundary lines A3-G3, G3-H3, H3-I3, I3-J3, and J3-A3 in FIG. 3. The amounts of the three components (% anionic compound/% solubilizing surfactant/% multivalent cationic antiseptic) with respect to each other at each of these points are as follows: A3=1.2/97.6/1.2; G3=26.0/42.9/31.2; H3=46.7/30.8/22.5; I3=69.0/22.8/8.2; and J3=52.7/34.7/12.6.

For certain of these embodiments, the amine oxide surfactant is selected from the group consisting of (C12-C16)alkyl(C1-C4)dialkylamine oxides, (C12-C16)alkylamido(C2-C4)alkylene(C1-4)dialkylamine oxides, and combinations thereof. For certain of these embodiments, the amine oxide surfactant is a (C12-C16)alkylamidopropyl(C1-C4)dialkylamine oxide, for example, a (C12-C16)alkylamidopropyldimethylamine oxide. For certain of these embodiments, the amine oxide surfactant is selected from the group consisting of laurylamidopropyldimethylamine oxide, lauryldimethylamine oxide, cetyldimethylamine oxide, and combinations thereof. For certain of these embodiments, the anionic sweetener is sodium saccharin.

Based upon the phase diagram of FIG. 3, in embodiments wherein the solubilizing surfactant is an amine oxide as described above, the amounts of the three components with respect to each other may be expressed as follows for the present compositions without precipitate: at least 0.7% amine oxide surfactant (AOS), not more than 31.4% anionic compound (A), not more than 82.2% multivalent cationic antiseptic (MCA); and at least 19% AOS, less than 50% A, and less than 50% MCA; and at least 16% AOS, not more than 76% A, and less than 30% MCA, but greater than 4.5% MCA at greater than 70% A. For certain of these embodiments, for longer term stability the amounts of the three components are preferably: greater than 22.8% AOS, less than 70% A, and not more than 31.2% MCA, but greater than 6.7% MCA at greater than 40% A and less than 20% MCA at less than 15% A.

Figure 4:
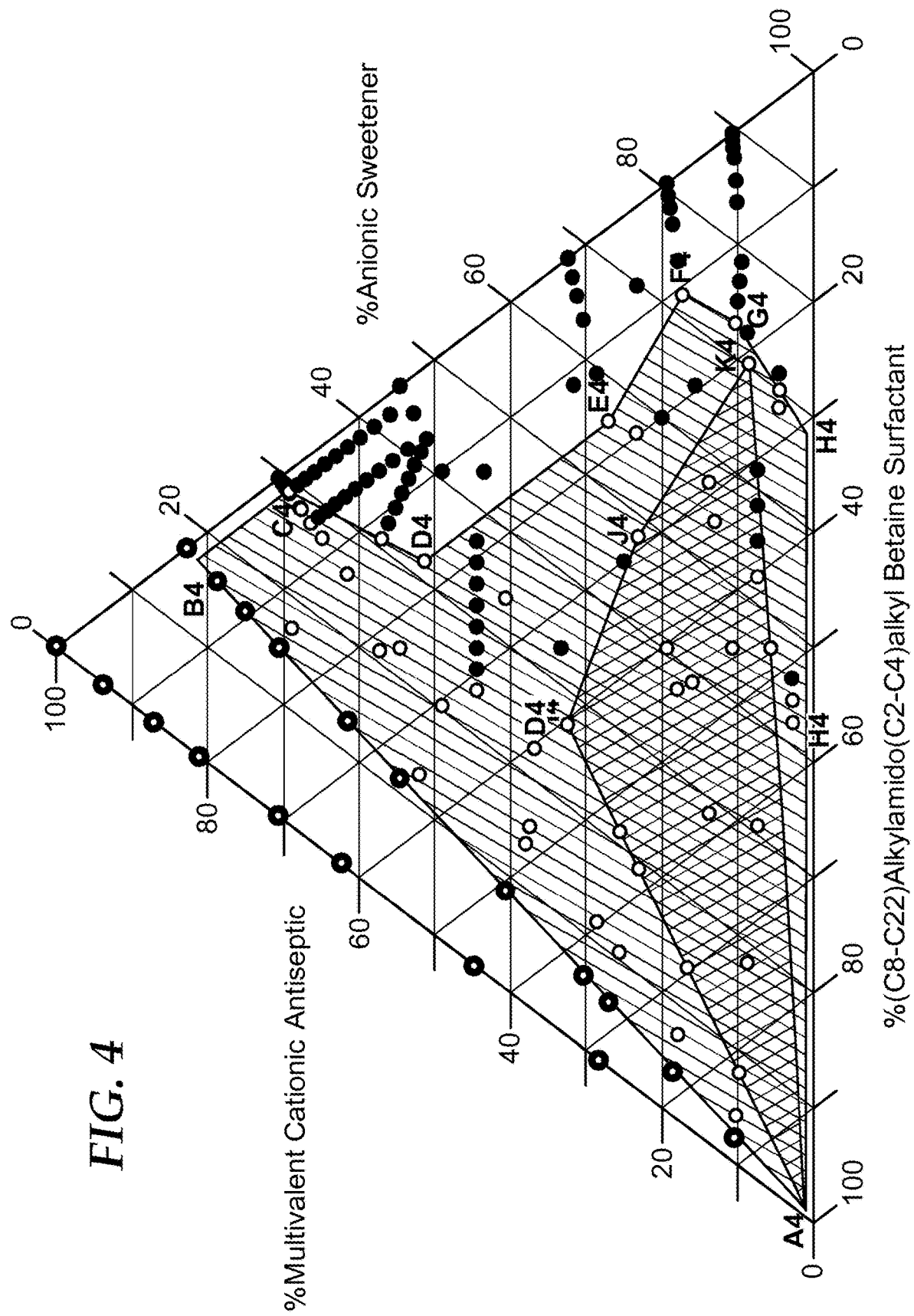
FIG. 4 is a phase diagram of % multivalent cationic antiseptic, % anionic sweetener, and % (C8-C22)alkylamido (C2-C4)alkyl betaine surfactant, showing regions without and with precipitate.

Referring to FIG. 4, a phase diagram is provided showing areas without and with precipitate based upon the relative amounts of anionic sweetener, (C8-C22)alkylamido(C2-C4) alkyl betaine surfactant, and multivalent cationic antiseptic represented by CHG. In FIG. 4, the area defined by the bold open circles, the open circles, and the solid circles are as described in FIG. 1. For certain embodiments, the anionic sweetener, the (C8-C22)alkylamido(C2-C4)alkyl betaine surfactant, and multivalent cationic antiseptic are present in the instant compositions in amounts within the boundary defined by points A4, B4, C4, D4, E4, F4, G4, and H4, and along the boundary lines B4-C4, C4-D4, D4-E4, E4-F4, F4-G4, G4-H4, and H4-A4 in FIG. 4. The boundary line A4-B4 is included in the area defined by the bold open circles. The amounts of the three components (% anionic compound/% solubilizing surfactant/% multivalent cationic antiseptic) with respect to each other at each of these points are as follows: A4=1.2/97.6/1.2; B4=16.9/1.9/81.2; C4=28.9/1.9/69.2; D4=31.8/16.9/51.3; E4=56.2/16.8/27.0; F4=72.0/10.8/17.2; G4=73.0/16.7/10.3; and H4=68.3/30.5/1.2.

For certain embodiments, preferably for longer term stability the anionic sweetener, (C8-C22)alkylamido(C2-C4)alkyl betaine surfactant, and multivalent cationic antiseptic are present in the instant compositions in amounts within the boundary defined by points A4, I4, J4, and K4 and along the boundary lines A4-I4, I4-J4, J4-K4, and K4-A4 in FIG. 4. The amounts of the three components (% anionic compound/% solubilizing surfactant/% multivalent cationic antiseptic) with respect to each other at each of these points are as follows: A4=1.2/97.6/1.2; I4=27.0/40.5/32.5; J4=48.0/28.9/23.1; and K4=70.4/21.1/8.5.

For certain of these embodiments, the (C8-C22)alkylamido(C2-C4)alkyl betaine comprises a (C12-C18)alkylamido(C2-C4)alkyl betaine, preferably a (C12-C18)alkylamidopropyl betaine. For certain of these embodiments, the anionic sweetener is sodium saccharin.

Based upon the phase diagram of FIG. 4, in embodiments wherein the solubilizing surfactant is a (C12-C18)alkylamido(C2-C4)alkyl betaine surfactant as described above, the amounts of the three components with respect to each other may be expressed as follows for the present compositions without precipitate: at least 1.9% betaine surfactant (BS), less than 30% A, not more than 81.2% MCA; and at least 10% BS, less than 32% A, less than 60% MCA; and at least 17% BS, less than 60% A, less than 50% MCA; and at least 10% BS, not more than 73% A, less than 25% MCA, but greater than 4.6% MCA at greater than 70.1% BS. For certain of these embodiments, for longer term stability the amounts of the three components are preferably: greater than 20% BS, not more than 70.4% A, less than 33% MCA, but at least 5% MCA at greater than 40% A, and less than 20% MCA at less than 17% A.

Referring to FIG. 5, a phase diagram is provided showing areas without and with precipitate, based upon the relative amounts of anionic sweetener, (C8-C22) alkylamido(C2-C4)alkylhydroxy sultaine surfactant, and multivalent cationic antiseptic represented by CHG. In FIG. 5, the area defined by the bold open circles, the open circles, and the solid circles are as described in FIG. 1. For certain embodiments, the anionic sweetener, the (C8-C22)alkylamido(C2-C4)alkylhydroxy sultaine surfactant, and multivalent cationic antiseptic are present in the instant compositions in amounts within the boundary defined by points A5, B5, C5, D5, E5, and F5, and along the boundary lines B5-C5, C5-D5, D5-E5, E5-F5, and F5-A5 in FIG. 5. The boundary line A5-B5 is included in the area defined by the bold open circles. The amounts of the three components (% anionic compound/% solubilizing surfactant/% multivalent cationic antiseptic) with respect to each other at each of these points are as follows: A5=1.2/97.60/1.2; B5=17.1/0.9/82.0; C5=29.1/10.9/70.0; D5=13.0/55.8/31.2; E5=31.3/53.7/15.0; and F5=74.9/16.1/9.0.

For certain embodiments, preferably for longer term stability the anionic sweetener, (C8-C22)alkylamido(C2-C4)alkylhydroxy sultaine surfactant, and multivalent cationic antiseptic are present in the instant compositions in amounts within the boundary defined by points A5, G5, and H5 and along the boundary lines A5-G5, G5-H5 and H5-A5 in FIG. 5. The amounts of the three components (% anionic compound/% solubilizing surfactant/% multivalent cationic antiseptic) with respect to each other at each of these points are as follows: A5=1.2/97.6/1.2; G5=15.4/66.1/18.5; and H5=47.6/41.0/11.4.

For certain of these embodiments, the (C8-C22)alkylamido(C2-C4)alkylhydroxy sultaine comprises a (C12-C18)alkylamido(C2-C4)alkylhydroxy sultaine, preferably a (C12-C18)alkylamidopropylhydroxy sultaine. For certain of these embodiments, the anionic sweetener is sodium saccharin.

Based upon the phase diagram of FIG. 5, in embodiments wherein the solubilizing surfactant is a (C8-C22)alkylamido(C2-C4)alkylhydroxy sultaine surfactant as described above, the amounts of the three components with respect to each other may be expressed as follows for the present compositions without precipitate: at least 0.9% sultaine surfactant (SS), less than 30% A, not more than 82% MCA; and at least 40% SS, not more than 18% A, less than 50% MCA; and at least 53% SS, not more than 31.3% A, less than 30% MCA; and at least 35% SS, less than 50% A, less than 15% MCA; and greater than 22% SS, less than 68% A, and not more than 11% MCA, but at least 4.5% MCA at greater than 50% A; and greater than 16% SS, less than 75% A, and less than 10% MCA, but at least 5% MCA at greater than 68% A. For certain of these embodiments, for longer term stability the amounts of the three components are preferably: greater than 40% SS, less than 48% A, and less than 19% MCA, but at last 6% MCA at greater than 30% A.

Referring to FIG. 6, a phase diagram is provided showing areas without and with precipitate based upon the relative amounts of anionic sweetener, nonionic micelle-forming surfactant, and multivalent cationic antiseptic represented by CHG. This takes into account all of the representative anionic sweetener, nonionic micelle-forming surfactants, and multivalent cationic antiseptic represented by CHG tested. This is essentially based upon a composite of FIGS. 7, 9, and 11, forming the area representing precipitate-free compositions. Boundary point F6 in FIG. 6 is established by imposing the boundary lines G11-H11 of FIG. 11 on the boundary lines E7-F7 in FIG. 7. In FIG. 6, the area defined by the bold open circles, the open circles, and the solid circles are as described in FIG. 1. For certain embodiments, the anionic sweetener, nonionic micelle-forming surfactants, and multivalent cationic antiseptic are present in the instant compositions in amounts within the boundary defined by points A6, B6, C6, D6, E6, F6, G6, H6, and I6, and along the boundary lines B6-C6, C6-D6, D6-E6, E6-F6, F6-G6, G6-H6, H6-I6, and I6-A6 in FIG. 6. The boundary line A6-B6 is included in the area defined by the bold open circles. The amounts of the three components (% anionic compound/% solubilizing surfactant/% multivalent cationic antiseptic) with respect to each other at each of these points are as follows: A6=1.2/97.6/1.2; B6=11.2/35.0/53.8; C6=17.5/35.0/47.5; D6=11.9/59.5/28.6; E6=29.8/59.5/10.7; F6=41.4/48.6/10.0; G6=43.1/48.6/8.3; H6=48.8/43.0/8.2; and I6=50.3/43.0/6.7.

For certain embodiments, preferably for longer term stability the anionic sweetener, micelle-forming nonionic surfactant, and multivalent cationic antiseptic are present in the instant compositions in amounts within the boundary defined by points A6, J6, K6, and L6, and along the boundary lines J6-K6, K6-L6, and L6-A6 in FIG. 6. The boundary line A6-J6 is included in the area defined by the bold open circles. The amounts of the three components (% anionic compound/% solubilizing surfactant/% multivalent cationic antiseptic) with respect to each other at each of these points are as follows: A6=1.2/97.6/1.2; J6=2.7/84.3/13.0; K6=10.9/76.1/13.0; L6=20.5/76.1/3.4.

For certain of these embodiments, the micelle-forming nonionic surfactant may be selected from the group consisting of (C8-C22)alkyl glucosides, (C8-C22)alkaryl glucosides, (C8-C22)aralkyl glucosides, poly(oxyethylene) sorbitan fatty acid esters, (C8-C22)alkyl poly(oxyethylene) esters, (C8-C22)alkaryl poly(oxyethylene) esters, (C8-C22) aralkyl poly(oxyethylene) esters, (C8-C22)alkyl poly(oxyethylene) ethers, (C8-C22)alkaryl poly(oxyethylene) ethers, (C8-C22)aralkyl poly(oxyethylene) ethers, polyglycerol (C8-C22)alkyl ethers, polyglycerol (C8-C22)fatty acid esters, and combinations thereof. For certain of these embodiments, the micelle-forming nonionic surfactants are selected from the group consisting of (C8-C22)alkyl glucosides, poly(oxyethylene) sorbitan fatty acid esters, (C8-C22) alkyl poly(oxyethylene) esters, (C8-C22)alkyl poly(oxyethylene) ethers, polyglycerol (C8-C22)alkyl ethers, polyglycerol (C8-C22)fatty acid esters, and combinations thereof. For certain of these embodiments, preferably for longer term stability the micelle-forming nonionic surfactant is a (C8-C22)alkyl glucoside, for example, a (C8-C22)alkyl mono and oligo glucopyranoside. For certain of these embodiments, the anionic sweetener is sodium saccharin.

Based upon the phase diagram of FIG. 6, in embodiments wherein the solubilizing surfactant is micelle-forming nonionic surfactant as described above, the amounts of the three components with respect to each other may be expressed as follows for the present compositions without precipitate: at least 35% micelle-forming nonionic surfactant (MFNS), not more than 18% A, not more than 54% MCA; and at least 59.5% MFNS, less than 30% A, and less than 30% MCA; and at least 48.6% MFNS, not more than 43.1% A, less than 11% MCA; at least 43% MFNS, not more than 50.3% A, not more than 8.3% MCA, but greater than 1.6% MCA at above 10% A, greater than 3.2% MCA at above 20% A, and greater than 4.1% MCA at above 30% A. For certain of these embodiments, for longer term stability the amounts of the three components are preferably: at least 76% MFNS, less than 20.5% A, and not more than 13% MCA, but greater than 1.6% MCA above 10% A.

Figure 7:
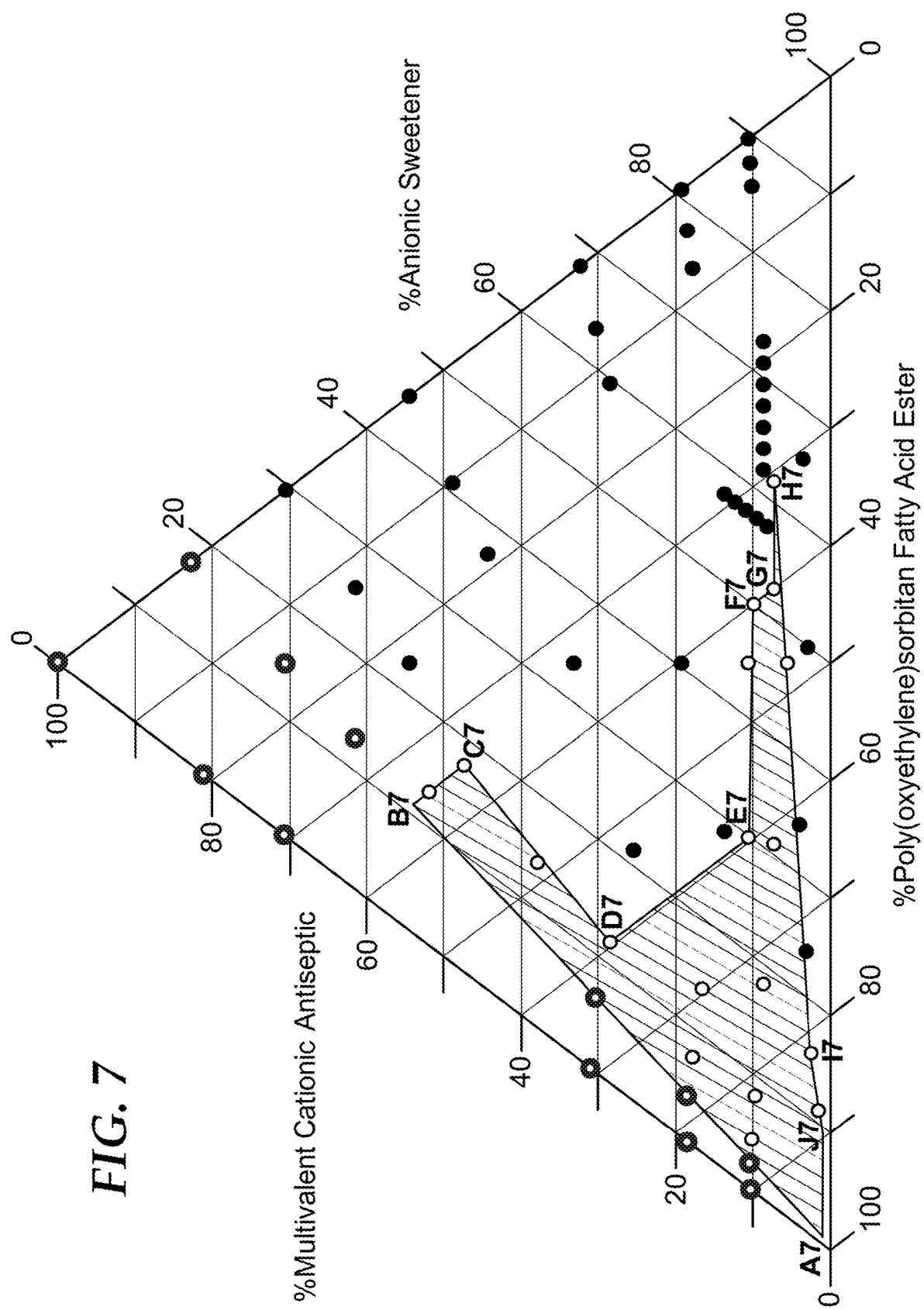
FIG. 7 is a phase diagram of % multivalent cationic antiseptic, % anionic sweetener, and % poly(oxyethylene) sorbitan fatty acid ester surfactant, showing regions without and with precipitate.

Referring to FIG. 7, a phase diagram is provided showing areas without and with precipitate based upon the relative amounts of anionic sweetener, poly(oxyethylene)sorbitan fatty acid ester surfactant, and multivalent cationic antiseptic represented by CHG. In FIG. 7, the area defined by the bold open circles, the open circles, and the solid circles are as described in FIG. 1. For certain embodiments, the anionic sweetener, the poly(oxyethylene)sorbitan fatty acid ester surfactant, and multivalent cationic antiseptic are present in the instant compositions in amounts within the boundary defined by points A7, B7, C7, D7, E7, F7, G7, H7, I7, and J7, and along the boundary lines B7-C7, C7-D7, D7-E7, E7-F7, F7-G7, G7-H7, H7-I7, I7-J7, and J7-A7 in FIG. 7. The boundary line A7-B7 is included in the area defined by the bold open circles. The amounts of the three components (% anionic compound/% solubilizing surfactant/% multivalent cationic antiseptic) with respect to each other at each of these points are as follows: A7=1.2/97.6/1.2; B7=11.2/35.0/53.8; C7=17.5/35.0/47.5; D7=11.9/59.5/28.6; E7=29.8/59.5/10.7; F7=50.0/40.0/10.0; G7=52.6/40.0/7.4; H7=61.7/30.9/7.4; I7=15.5/82.0/2.6, and J7=9.2/89.6/1.2.

Based upon the phase diagram of FIG. 7, in embodiments wherein the solubilizing surfactant is a poly(oxyethylene) sorbitan fatty acid ester surfactant as described above, the amounts of the three components with respect to each other may be expressed as follows for the present compositions without precipitate: at least 35% poly(oxyethylene)sorbitan fatty acid ester surfactant (PSFAS), less than 18% A, not more than 54% MCA; and more than 59% PSFAS, less than 30% A, less than 30% MCA but greater than 3.2% MCA at greater than 20% A; and at least 40% PSFAS, less than 53% A, less than 11% MCA but greater than 4.1% MCA at greater than 30% A; and greater than 30% PSFAS, less than 65% A, and less than 8% MCA but greater than 4.1% MCA.

For certain of these embodiments, the poly(oxyethylene) sorbitan fatty acid ester comprises esters of (C12-C18) fatty acids. Preferably, for certain embodiments the poly(oxyethylene)sorbitan fatty acid ester includes at least 10 and not more than 40 or 30, more preferably at least 15 and not more than 25 repeating units of —CH$_2$CH$_2$—O— (oxyethylene). For certain of these embodiments, the poly(oxyethylene) sorbitan fatty acid ester is a monoester, for example, polysorbate 20 or TWEEN 20.

For certain of these embodiments, the anionic sweetener is sodium saccharin.

Figure 8:
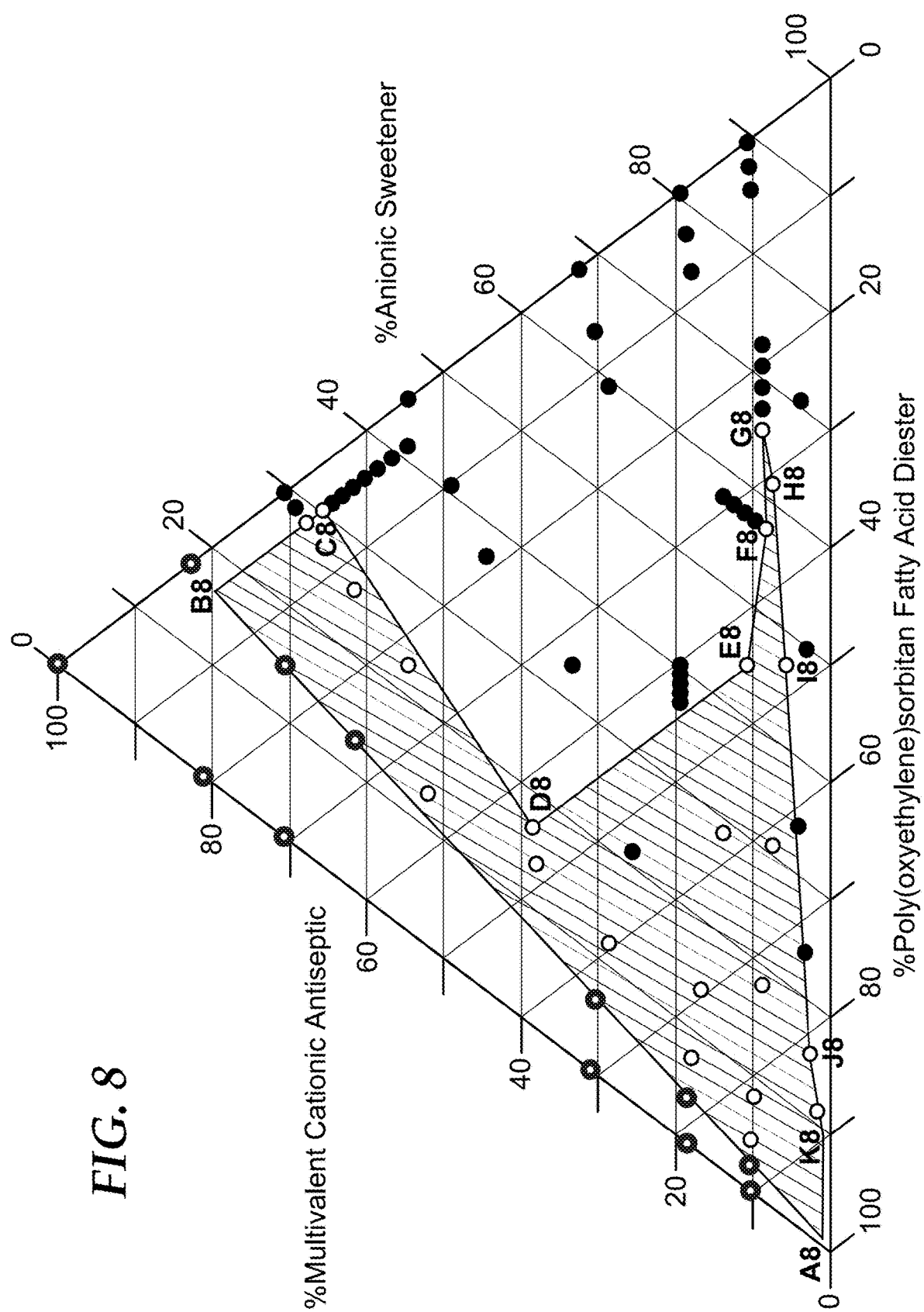
FIG. 8 is a phase diagram of % multivalent cationic antiseptic, % anionic sweetener, and % poly(oxyethylene) sorbitan fatty acid diester surfactant, showing regions without and with precipitate.

Referring to FIG. 8, a phase diagram is provided showing areas without and with precipitate, based upon the relative amounts of anionic sweetener, poly(oxyethylene)sorbitan fatty acid diester surfactant, and multivalent cationic antiseptic represented by CHG. In FIG. 8, the area defined by the bold open circles, the open circles, and the solid circles are as described in FIG. 1. For certain embodiments, the anionic sweetener, the poly(oxyethylene)sorbitan fatty acid diester surfactant, and multivalent cationic antiseptic are present in the instant compositions in amounts within the boundary defined by points A8, B8, C8, D8, E8, F8, G8, H8, I8, J8, and K8, and along the boundary lines B8-C8, C8-D8, D8-E8, E8-F8, F8-G8, G8-H8, H8-I8, I8-J8, J8-K8, and K8-A8 in FIG. 8. The boundary line A8-B8 is included in the area defined by the bold open circles. The amounts of the three components (% anionic compound/% solubilizing surfactant/% multivalent cationic antiseptic) with respect to each other at each of these points are as follows: A8=1.2/97.6/1.2; B8=16.6/4.0/79.4; C8=30.4/4.0/65.6; D8=16.9/44.6/38.5; E8=44.6/44.6/10.7; F8=57.5/34.3/8.3; G8=65.7/25.6/8.8; H8=61.7/30.9/7.4; I8=47.2/47.2/5.7; J8=15.5/82.0/2.6; and K8=9.2/89.6/1.2.

Based upon the phase diagram of FIG. 8, in embodiments wherein the solubilizing surfactant is a poly(oxyethylene) sorbitan fatty acid diester surfactant as described above, the amounts of the three components with respect to each other may be expressed as follows for the present compositions without precipitate: at least 4% poly(oxyethylene)sorbitan fatty acid diester surfactant (PSDFAS), less than 31% A, less than 80% MCA; and at least 45% PSDFAS, less than 45% A, less than 39% MCA but greater than 4.1% MCA at greater than 20% A; and more than 35% PSDFAS, less than 58% A, less than 11% MCA but greater than 4.1% MCA; and more than 25% PSDFAS, less than 66% A, and less than 9% MCA but greater than 4.1% MCA.

For certain of these embodiments, the poly(oxyethylene) sorbitan fatty acid diester comprises esters of (C12-C18) fatty acids. Preferably, for certain embodiments the poly (oxyethylene)sorbitan fatty acid diester includes at least 30 and not more than 50, more preferably at least 35 and not more than 45 repeating units of —CH$_2$CH$_2$—O—. For certain of these embodiments, the poly(oxyethylene)sorbitan fatty acid diester is a diester of a (C16-C18)fatty acid, for example, poly(oxyethylene) 40 sorbitan diisostearate, such as CANARCEL.

For certain of these embodiments, the anionic sweetener is sodium saccharin.

Figure 9:
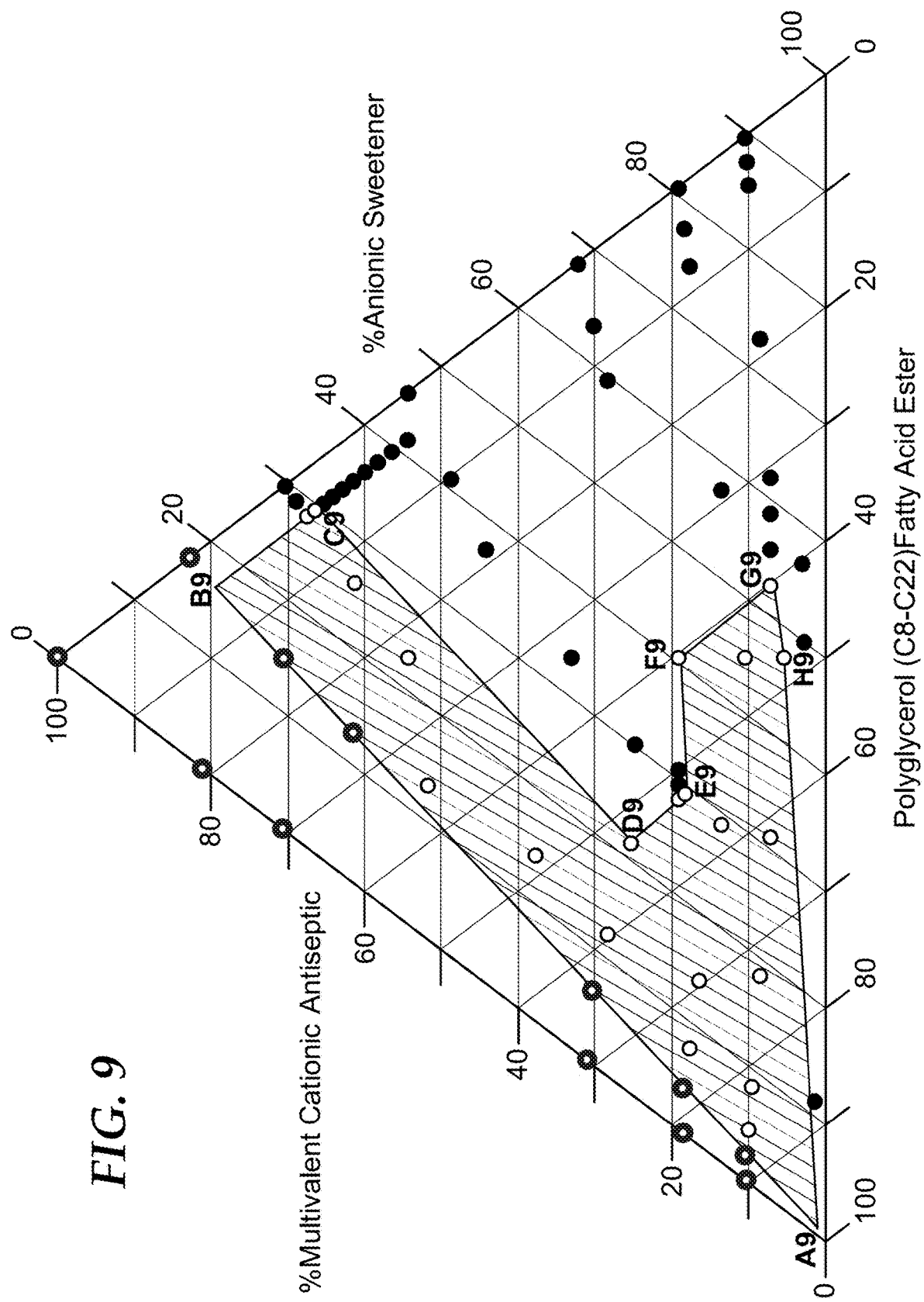
FIG. 9 is a phase diagram of % multivalent cationic antiseptic, % anionic sweetener, and % polyglycerol (C8-C22)fatty acid ester surfactant, showing regions without and with precipitate.

Referring to FIG. 9, a phase diagram is provided showing areas without and with precipitate, based upon the relative amounts of anionic sweetener, polyglycerol (C8-C22)fatty acid ester surfactant, and multivalent cationic antiseptic represented by CHG. In FIG. 9, the area defined by the bold open circles, the open circles, and the solid circles are as described in FIG. 1. For certain embodiments, the anionic sweetener, the polyglycerol (C8-C22)fatty acid ester surfactant, and multivalent cationic antiseptic are present in the instant compositions in amounts within the boundary defined by points A9, B9, C9, D9, E9, F9, G9 and H9, and along the boundary lines B9-C9, C9-D9, D9-E9, E9-F9, F9-G9, G9-H9, and H9-A9 in FIG. 9. The boundary line A9-B9 is included in the area defined by the bold open circles. The amounts of the three components (% anionic compound/% solubilizing surfactant/% multivalent cationic antiseptic) with respect to each other at each of these points are as follows: A9=1.2/97.6/1.2; B9=16.6/4.0/79.4; C9=29.3/4.0/66.7; D9=21.3/53.2/25.5; E9=29.0/52.5/18.5; F9=40.3/40.3/19.4; G9=52.5/40.1/7.4; and H9=47.2/47.2/5.7.

Based upon the phase diagram of FIG. 9, in embodiments wherein the solubilizing surfactant is a polyglycerol (C8-C22)fatty acid ester surfactant as described above, the amounts of the three components with respect to each other may be expressed as follows for the present compositions without precipitate: at least 4% polyglycerol (C8-C22)fatty acid ester surfactant (PGFAS), less than 30% A, less than 80% MCA; and at least 40% PGFAS, less than 29% A and less than 50% MCA but greater than 1.6% MCA; and at least 40% PGFAS, less than 53% A, less than 18.5% MCA but greater than 3.3% MCA.

For certain of these embodiments, the polyglycerol (C8-C22)fatty acid ester comprises (C12-C18)fatty acids. Preferably, for certain embodiments the polyglycerol (C8-C22) fatty acid ester includes at least 5 or 7 and not more than 20 or 15 repeating units of —CH$_2$CH(OH)CH$_2$—O—. For certain of these embodiments, the polyglycerol (C8-C22) fatty acid ester is a (C12-C16)fatty acid ester, for example, polyglycerol 10 myristate, such as DECAGLYN 1M.

For certain of these embodiments, the anionic sweetener is sodium saccharin.

Figure 10:
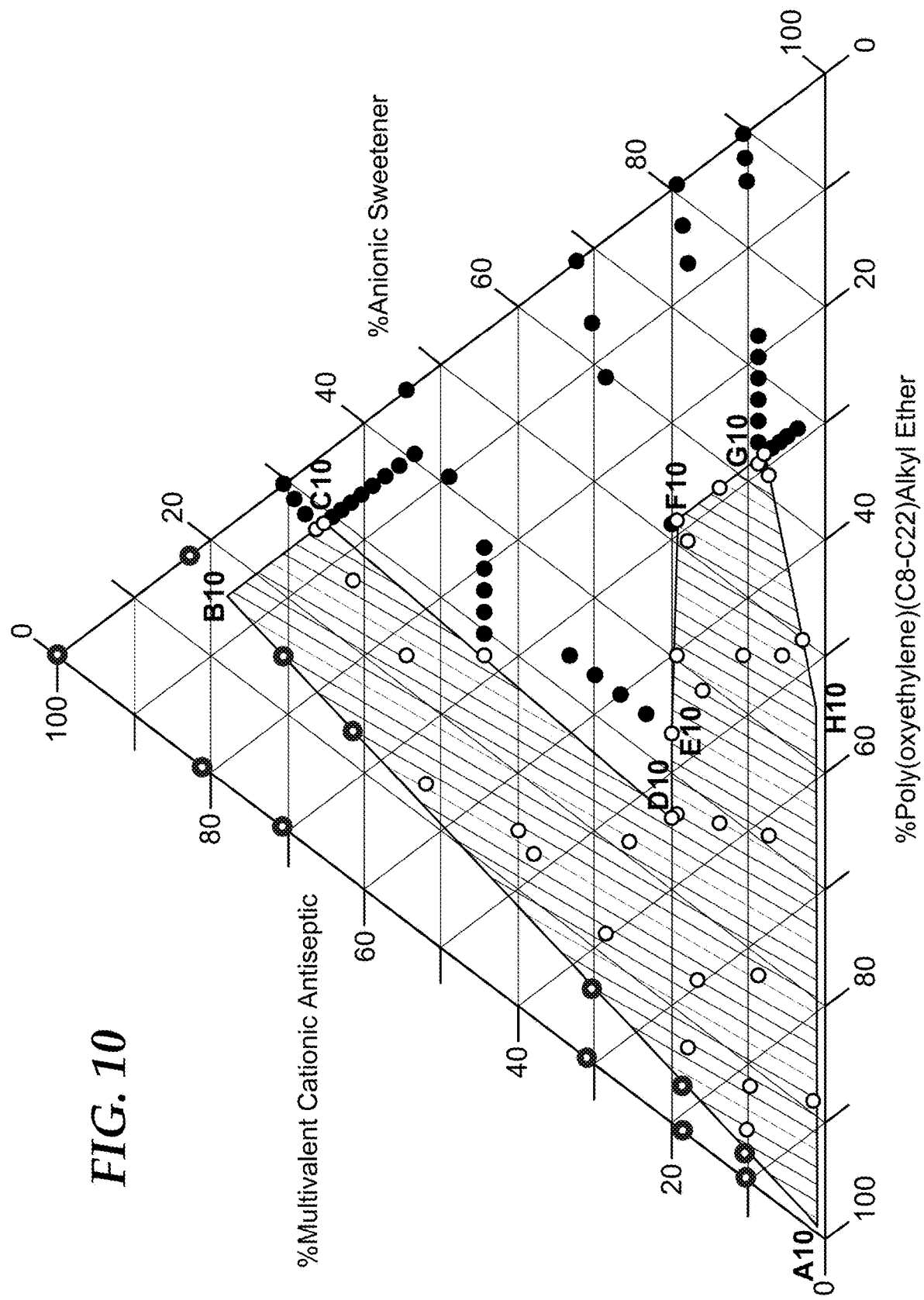
FIG. 10 is a phase diagram of % multivalent cationic antiseptic, % anionic sweetener, and % poly(oxyethylene) (C8-C22)alkyl ether surfactant, showing regions without and with precipitate.

Referring to FIG. 10, a phase diagram is provided showing areas without and with precipitate based upon the relative amounts of anionic sweetener, poly(oxyethylene) (C8-C22)alkyl ether surfactant, and multivalent cationic antiseptic represented by CHG. In FIG. 10, the area defined by the bold open circles, the open circles, and the solid circles are as described in FIG. 1. For certain embodiments, the anionic sweetener, the poly(oxyethylene) (C8-C22)alkyl ether surfactant, and multivalent cationic antiseptic are present in the instant compositions in amounts within the boundary defined by points A10, B10, C10, D10, E10, F10, G10, and H10, and along the boundary lines B10-C10, C10-D10, D10-E10, E10-F10, F10-G10, G10-H10, and H10-A10 in FIG. 10. The boundary line A10-B10 is included in the area defined by the bold open circles. The amounts of the three components (% anionic compound/% solubilizing surfactant/% multivalent cationic antiseptic) with respect to each other at each of these points are as follows: A10=1.2/97.6/1.2; B10=16.2/6.0/77.8; C10=28.7/6.0/65.3; D10=26.1/53.9/20.0; E10=33.3/46.7/20.0; F10=51.9/28.7/19.4; G10=63.3/28.7/8.0; and H10=45.0/53.8/1.2.

Based upon the phase diagram of FIG. 10, in embodiments wherein the solubilizing surfactant is a poly(oxyethylene) (C8-C22)alkyl ether surfactant as described above, the amounts of the three components with respect to each other may be expressed as follows for the present compositions without precipitate: at least 6% poly(oxyethylene) (C8-C22)alkyl ether surfactant (PAES), less than 29% A, less than 78% MCA; and at least 28% PAES, not more than 63.3% A, not more than 20% MCA.

For certain of these embodiments, the poly(oxyethylene) (C8-C22)alkyl ether comprises (C12-C18)alkyl ethers. Preferably, for certain embodiments the poly(oxyethylene) (C8-C22)alkyl ether includes at least 10 and not more than 40, more preferably at least 15 and not more than 30 or 25 repeating units of —CH$_2$CH$_2$—O—. For certain of these embodiments, the poly(oxyethylene) (C8-C22)alkyl ether is a (C16-C18)alkyl ether, for example, poly(oxyethylene) 20 stearyl ether, such as BRIJ 78.

For certain of these embodiments, the anionic sweetener is sodium saccharin.

Referring to FIG. 11, a phase diagram is provided showing areas without and with precipitate, based upon the relative amounts of anionic sweetener, (C8-C22)alkyl polyglycoside surfactant, and multivalent cationic antiseptic represented by CHG. In FIG. 11, the area defined by the bold open circles, the open circles, and the solid circles are as described in FIG. 1. For certain embodiments, the anionic sweetener, the (C8-C22)alkyl polyglycoside surfactant, and multivalent cationic antiseptic are present in the instant compositions in amounts within the boundary defined by points A11, B11, C11, D11, E11, F11, G11, H11, I11, J11, and K11 and along the boundary lines B11-C11, C11-D11, D11-E11, E11-F11, F11-G11, G11-H11, H11-I11, I11-J11, J11-K11, and K11-A11 in FIG. 11. The boundary line A11-B11 is included in the area defined by the bold open circles. The amounts of the three components (% anionic compound/% solubilizing surfactant/% multivalent cationic antiseptic) with respect to each other at each of these points are as follows: A11=1.2/97.6/1.2; B11=17.0/1.4/81.6; C11=30.1/1.4/68.5; D11=19.4/49.6/31.0; E11=13.3/60.9/25.8; F11=22.7/58.2/19.1; G11=34.7/48.6/16.7; H11=43.1/48.6/8.3; I11=48.8/43.0/8.2; J11=50.3/43.0/6.7; and K11=21.5/76.1/2.4.

For certain embodiments, preferably for longer term stability the anionic sweetener, (C8-C22)alkyl polyglycoside surfactant, and multivalent cationic antiseptic are present in the instant compositions in amounts within the boundary defined by points A11, L11, M11, and K11, and along the boundary lines L11-M11, M11-K11, and K11-A11 of FIG. 11. The boundary line A11-L11 is included in the area defined by the bold open circles. The amounts of the three components (% anionic compound/% solubilizing surfactant/% multivalent cationic antiseptic) with respect to each other at each of these points are as follows: A11=1.2/97.6/1.2; L11=2.7/84.3/13.0; M11=10.9/76.1/13.0; K11=21.5/76.1/2.4.

Based upon the phase diagram of FIG. 11, in embodiments wherein the solubilizing surfactant is a (C8-C22)alkyl polyglycoside surfactant as described above, the amounts of the three components with respect to each other may be expressed as follows for the present compositions without precipitate: at least 1.4% (C8-C22)alkyl polyglycoside surfactant (APGS), not more than 30.1% A, not more than 81.6% MCA; and at least 40% APGS, not more than 20% A, less than 40% MCA; and at least 55% APGS, not more than 16% A, and less than 30% MCA; and at least 59% APGS, less than 40% A, and less than 25% MCA; and at least 48% APGS, not more than 43.1% A, and less than 18% MCA; and at least 43% APGS, not more than 50.3% A, not more than 8.3% MCA; but at least 3% MCA at above 30% A. For certain of these embodiments, for longer term stability the amounts of the three components are preferably: greater than 76% APGS, less than 21.5% A, and not more than 13% MCA.

For certain of these embodiments, the (C8-C22)alkyl polyglycoside comprises (C8-C12)fatty alcohol ethers. Preferably, for certain embodiments the (C8-C22)alkyl polyglycoside includes mono and oligoglycosides, for example, mono and oligoglucopyranosides. For certain of these embodiments, the (C8-C22)alkyl polyglycoside is a (C8-C10)fatty alcohol ether, for example, a (C8-C10) fatty alcohol ether of mono and oligoglucopyranosides, such as GLUCOPON 225DK.

For certain of these embodiments, the anionic sweetener is sodium saccharin.

Referring to FIG. 12, a phase diagram is provided showing areas without and with precipitate based upon the relative amounts of a dihydrogen phosphate salt, poly(oxyethylene)sorbitan fatty acid ester surfactant, and multivalent cationic antiseptic represented by CHG. In FIG. 12, the area defined by the bold open circles, the open circles, and the solid circles are as described in FIG. 1. For certain embodiments, the dihydrogen phosphate salt, the poly(oxyethylene)sorbitan fatty acid ester surfactant, and multivalent cationic antiseptic are present in the instant compositions in amounts within the boundary defined by points A12, B12, C12, D12, E12, F12, G12, H12, I12 and J12, and along the boundary lines B12-C12, C12-D12, D12-E12, E12-F12, F12-G12, G12-H12, H12-I12, I12-J12, and J12-A12 in FIG. 12. The boundary line A12-B12 is included in the area defined by the bold open circles. The amounts of the three components (% anionic compound/% solubilizing surfactant/% multivalent cationic antiseptic) with respect to each other at each of these points are as follows: A12=1.2/97.6/1.2; B12=16.9/2.0/81.1; C12=42.24/2.00/55.76; D12=35.2/20.4/44.4; E12=40.5/16.7/42.9; F12=60.5/16.7/22.8; G12=36.3/44.4/19.4; H12=39.8/48.6/11.6; I12=24.0/70.0/6.0; and J12=28.8/70.0/1.2.

For certain embodiments, preferably for longer term stability the dihydrogen phosphate anion, the poly(oxyethylene)sorbitan fatty acid ester surfactant, and multivalent cationic antiseptic are present in the instant compositions in amounts within the boundary defined by points A12, K12, I12, and J12 and along the boundary lines A12-K12, K12-I12, I12-J12, and J12-A12 in FIG. 12. The amounts of the three components (% anionic compound/% solubilizing surfactant/% multivalent cationic antiseptic) with respect to each other at each of these points are as follows: A12=1.2/97.6/1.2; K12=7.5/74.6/17.9; I12=24.0/70.0/6.0; and J12=28.8/70.0/1.2.

Based upon the phase diagram of FIG. 12, in embodiments wherein the solubilizing surfactant is a poly(oxyethylene)sorbitan fatty acid ester surfactant as described above, the amounts of the three components with respect to each other may be expressed as follows for the present compositions without precipitate: at least 2% poly(oxyethylene)sorbitan fatty acid ester surfactant (PSFAS), less than 43% A, not more than 81% MCA; and at least 8% PSFAS, less than 40% A, less than 52% MCA; and at least 17% PSFAS, less than 36% A, less than 48% MCA; at least 17% PSFAS, less than 61% A, and less than 43% MCA; wherein the MCA is greater than 7.4% at above 30% A, at least 10% at greater than 35% A, and at least 20% at above 40% A. For certain of these embodiments, for longer term stability the amounts of the three components are preferably: at least 70% PSFAS, less than 30% A, and less than 18% MCA.

For certain of these embodiments the dihydrogen phosphate is sodium dihydrogen phosphate.

Figure 13:
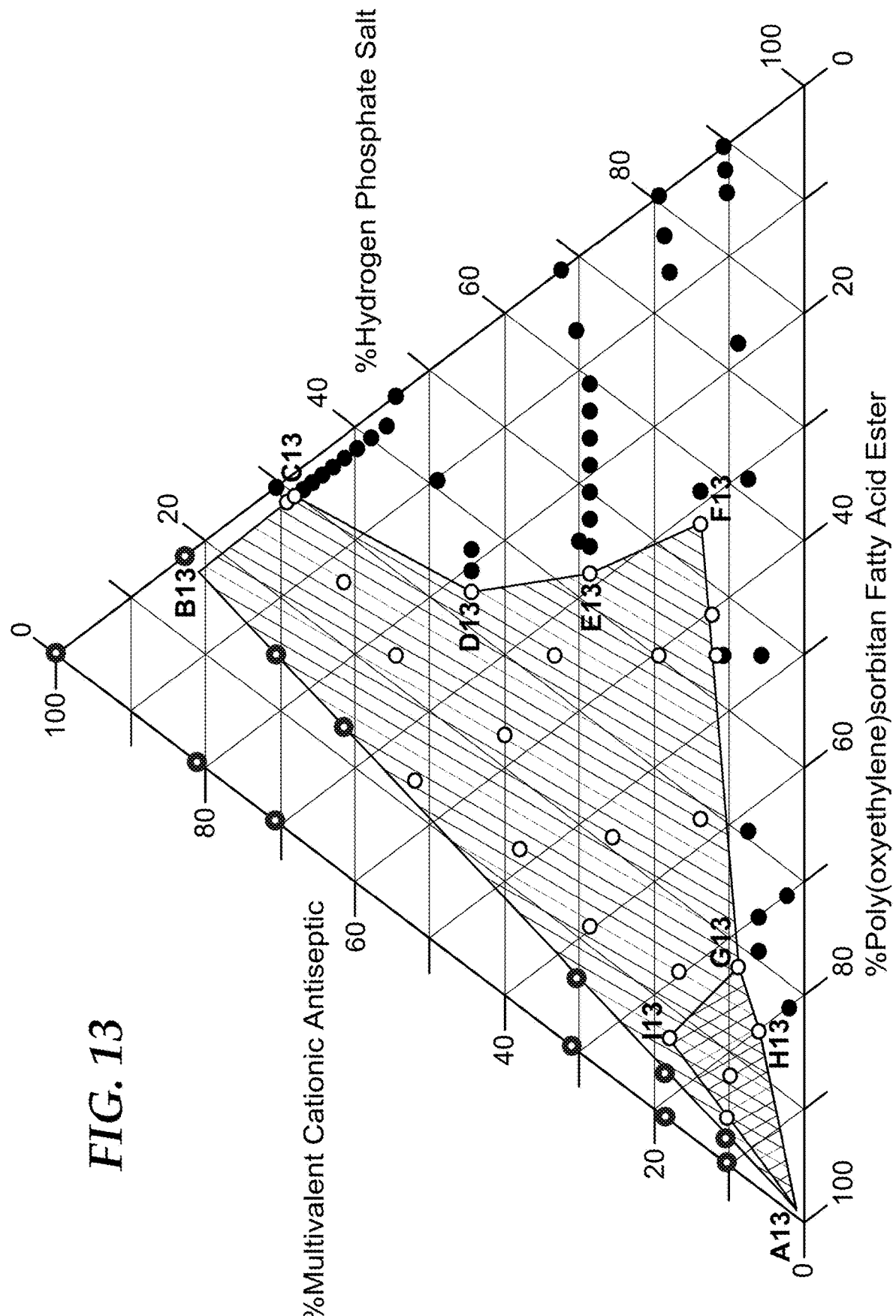
FIG. 13 is a phase diagram of % multivalent cationic antiseptic, % hydrogen phosphate salt, and % poly(oxyethylene)sorbitan fatty acid ester surfactant, showing regions without and with precipitate.

Referring to FIG. 13, a phase diagram is provided showing areas without and with precipitate based upon the relative amounts of a hydrogen phosphate salt, poly(oxyethylene)sorbitan fatty acid ester surfactant, and multivalent cationic antiseptic. In FIG. 13, the area defined by the bold open circles, the open circles, and the solid circles are as described in FIG. 1. For certain embodiments, the hydrogen phosphate salt, the poly(oxyethylene)sorbitan fatty acid ester surfactant, and multivalent cationic antiseptic are present in the instant compositions in amounts within the boundary defined by points A13, B13, C13, D13, E13, F13, G13, and H13, and along the boundary lines B13-C13, C13-D13, D13-E13, E13-F13, F13-G13, G13-H13, and H13-A13 in FIG. 13. The boundary line A13-B13 is included in the area defined by the bold open circles. The amounts of the three components (% anionic compound/% solubilizing surfactant/% multivalent cationic antiseptic) with respect to each other at each of these points are as follows: A13=1.2/97.6/1.2; B13=16.9/2.0/81.1; C13=29.9/2.0/68.1; D13=33.3/22.2/44.4; E13=42.9/28.6/28.6; F13=54.6/31.6/13.8; G13=18.3/723.0/8.8; and H13=14.0/80.0/6.0.

For certain embodiments, preferably for longer term stability the hydrogen phosphate salt, the poly(oxyethylene)sorbitan fatty acid ester surfactant, and multivalent cationic antiseptic are present in the instant compositions in amounts within the boundary defined by points A13, I13, G13, H13, and along the boundary lines A13-I13, I13-G13, G13-H13, and H13-A13 in FIG. 13. The amounts of the three components (% anionic compound/% solubilizing surfactant/% multivalent cationic antiseptic) with respect to each other at each of these points are as follows: A13=1.2/97.6/1.2; I13=7.5/74.6/17.9; G13=18.3/73.0/8.8; and H13=14.0/80.0/6.0.

Based upon the phase diagram of FIG. 13, in embodiments wherein the solubilizing surfactant is a poly(oxyethylene)sorbitan fatty acid ester surfactant as described above, the amounts of the three components with respect to each other may be expressed as follows for the present compositions without precipitate: at least 2% poly(oxyethylene)sorbitan fatty acid ester surfactant (PSFAS), not more than 30% A, not more than 81% MCA; and at least 18% PSFAS, not more than 33% A, not more than 50% MCA; and at least 22% PSFAS, not more than 43% A, less than 45% MCA; more than 28% PSFAS, less than 55% A, and less than 29% but at least 12% MCA; and more than 60% PSFAS, less than 30% A, and less than 33% MCA but greater than 8% MCA; and greater than 70% PSFAS, less than 20% A and less than 24% MCA but at least 2% MCA. For certain of these embodiments, for longer term stability the amounts of the three components are preferably: greater than 72% PSFAS, less than 20% A, and less than 18% MCA but at least 2% MCA.

For certain of these embodiments the hydrogen phosphate is disodium hydrogen phosphate.

Referring to FIG. 14, a phase diagram is provided showing areas without and with precipitate based upon the relative amounts of a bicarbonate salt, poly(oxyethylene)sorbitan fatty acid ester surfactant, and multivalent cationic antiseptic represented by CHG, wherein the pH of the composition is 6 to 8, preferably 6.5 to 8, or about 7. In FIG. 14, the area defined by the bold open circles, the open circles, and the solid circles are as described in FIG. 1. For certain embodiments, the bicarbonate salt, the poly(oxyethylene)sorbitan fatty acid ester surfactant, and multivalent cationic antiseptic are present in the instant compositions in amounts within the boundary defined by points A14, B14, C14, D14, and E14, and along the boundary lines B14-C14, C14-D14, D14-E14, and E15-A14 in FIG. 14. The boundary line A14-B14 is included in the area defined by the bold open circles. The amounts of the three components (% anionic compound/% solubilizing surfactant/% multivalent cationic antiseptic) with respect to each other at each of these points are as follows: A14=1.2/97.6/1.2; B14=77.8/4.3/17.9; C14=85.5/4.3/10.3; D14=61.7/30.9/7.4; E14=52.9/45.9/1.2.

For certain embodiments, preferably for longer term stability the bicarbonate salt, the poly(oxyethylene)sorbitan fatty acid ester surfactant, and multivalent cationic antiseptic are present in the instant compositions in amounts within the boundary defined by points A14, F14, G14, and H14 and along the boundary lines A14-F14, F14-G14, G14-H14, and H14-A14. The amounts of the three components (% anionic compound/% solubilizing surfactant/% multivalent cationic antiseptic) with respect to each other at each of these points are as follows: A14=1.2/97.6/1.2; F14=76.4/6.0/17.6; G14=80.0/6.0/14.0; H14=30.8/68.0/1.2.

Based upon the phase diagram of FIG. 14, in embodiments wherein the solubilizing surfactant is a poly(oxyethylene)sorbitan fatty acid ester surfactant as described above, the amounts of the three components with respect to each other may be expressed as follows for the present compositions without precipitate: at least 4% poly(oxyethylene) sorbitan fatty acid ester surfactant (PSFAS), less than 86% A, less than 19% but not less than 10% MCA; and at least 10% PSFAS, less than 80% A, less than 17% MCA but at least 7% MCA; and at least 40% PSFAS, less than 59% A, less than 13% MCA. For certain of these embodiments, for longer term stability the amounts of the three components are preferably: at least 6% PSFAS, not more than 80% A, and less than 18% MCA but at least 11% MCA; and at least 20% PSFAS, less than 70% A, and less than 15% MCA but at least 8% MCA; and at least 40% PSFAS, less than 55% A, and less than 12% MCA but greater than 5% MCA at less than 60% PSFAS and greater than 3% MCA at less than 70% PSFAS.

Referring to FIG. 15, a phase diagram is provided showing areas without and with precipitate based upon the relative amounts of the bicarbonate salt, poly(oxyethylene) sorbitan fatty acid ester surfactant, and multivalent cationic antiseptic represented by CHG, wherein the pH of the composition is about 9.1. Because CHG is unstable at higher pH, a pH of not more than 9.1 is preferred, not more than 9 being more preferred and not more than 8 being most preferred. A pH of at least 6 or 6.5 is preferred. For certain embodiments for chemical long term stability a pH of 6-7 is preferred. In FIG. 15, the area defined by the bold open circles, the open circles, and the solid circles are as described in FIG. 1. For certain embodiments, the bicarbonate salt, the poly(oxyethylene)sorbitan fatty acid ester surfactant, and multivalent cationic antiseptic are present in the instant compositions in amounts within the boundary defined by points A15, B15, C15, D15, and E15, and along the boundary lines B15-C15, C15-D15, D15-E15, and E15-A15 in FIG. 15. The boundary line A15-B15 is included in the area defined by the bold open circles. The amounts of the three components (% anionic compound/% solubilizing surfactant/% multivalent cationic antiseptic) with respect to each other at each of these points are as follows: A15=1.2/97.6/1.2; B15=79.5/2.2/18.3; C15=87.3/2.2/10.5; D15=47.2/47.2/5.7; E15=43.7/55.1/1.2.

For certain embodiments, preferably for longer term stability at this pH the bicarbonate salt, the poly(oxyethylene) sorbitan fatty acid ester surfactant, and multivalent cationic antiseptic are present in the instant compositions in amounts within the boundary defined by points A15, F15, D15, and G15, and along the boundary lines F15-D15, D15-G15, G15-A15 in FIG. 15. The boundary line A15-F15 is included in the area defined by the bold open circles. The amounts of the three components (% anionic compound/% solubilizing surfactant/% multivalent cationic antiseptic) with respect to each other at each of these points are as follows: A15=1.2/97.6/1.2; F15=42.8/47.2/10.0; D15=47.2/47.2/5.7; G15=12.7/86.1/1.2.

Based upon the phase diagram of FIG. 15, in embodiments wherein the solubilizing surfactant is a poly(oxyethylene)sorbitan fatty acid ester surfactant as described above, the amounts of the three components with respect to each other may be expressed as follows for the present compositions without precipitate: at least 2% poly(oxyethylene) sorbitan fatty acid ester surfactant (PSFAS), not more than 87.3% A, less than 19% but at least 10% MCA; and at least 10% PSFAS, less than 81% A, and less than 17% MCA but at least 7% MCA; and at least 30% PSFAS, less than 65% A, and less than 14% MCA but at least 5% MCA, and at least 47% PSFAS, less than 47% A, not more than 10% MCA. For certain of these embodiments, for longer term stability the amounts of the three components are preferably: at least 47% PSFAS, less than 47%% A, and not more than 10% MCA but at least 5.5%, wherein the MCA is greater than 2.1% but less than 6% at less than 80% PSFAS; and at least 3% but less than 8% at less than 70% PSFAS.

For certain of these embodiments wherein the anionic compound is a bicarbonate salt, the salt is an alkali metal bicarbonate or an alkaline earth metal bicarbonate. In some embodiments the salt is sodium bicarbonate or potassium bicarbonate.

Referring to FIG. 16, a phase diagram is provided showing areas without and with precipitate based upon the relative amounts of an anionic dye, poly(oxyethylene)sorbitan fatty acid ester surfactant, and multivalent cationic antiseptic represented by CHG. The bold open circles, the open circles, and the solid circles are as described in FIG. 1. For certain embodiments, the anionic dye, the poly(oxyethylene)sorbitan fatty acid ester surfactant, and multivalent cationic antiseptic are present in the instant compositions in amounts within the boundary defined by points A16, B16, C16, and D16, and along the boundary lines A16-B16, B16-C16, C16-D16, and D16-A16 in FIG. 16. The amounts of the three components (% anionic compound/% solubilizing surfactant/% multivalent cationic antiseptic) with respect to each other at each of these points are as follows: A16=1.2/97.6/1.2; B16=2.2/87.3/10.5; C16=44.8/49.5/5.7; and D16=49.3/49.5/1.20.

For certain embodiments, preferably for longer term stability the anionic dye, poly(oxyethylene)sorbitan fatty acid ester surfactant, and multivalent cationic antiseptic are present in the instant compositions in amounts within the boundary defined by points A16, B16, E16, and D16 and along the boundary lines A16-B16, B16-E16, E16-D16, and D16-A16 in FIG. 16. The amounts of the three components (% anionic compound/% solubilizing surfactant/% multivalent cationic antiseptic) with respect to each other at each of these points are as follows: A16=1.2/97.6/1.2; B16=2.2/87.3/10.5; E16=47.1/49.9/3.0; and D16=49.3/49.5/1.20.

Based upon the phase diagram of FIG. 16, in embodiments wherein the solubilizing surfactant is a poly(oxyethylene)sorbitan fatty acid ester surfactant as described above, the amounts of the three components with respect to each other may be expressed as follows for the present compositions without precipitate: at least 49% poly(oxyethylene) sorbitan fatty acid ester surfactant (PSFAS), less than 50% A, less than 6% MCA; and at least 63% PSFAS, less than 30% A, less than 7% MCA; and at least 70% PSFAS, not more than 20% A, not more than 10% MCA. For certain of these embodiments, for longer term stability the amounts of the three components are preferably: at least 49% poly(oxyethylene)sorbitan fatty acid ester surfactant (PSFAS), less than 50% A, less than 3% MCA; and at least 60% PSFAS, less than 35% A, less than 7% MCA; and at least 70% PSFAS, not more than 20% A, not more than 8.5% MCA; and at least 80% PSFAS, not more than 10% A, and not more than 10% MCA.

For certain of these embodiments, the anionic dye is a red dye comprising at least one sulfonate group, in certain embodiments, preferably not more than two sulfonate groups. For certain of these embodiments, the red dye is Allura Red AC (also known as FD&C Red 40).

Referring to FIG. 17, a phase diagram is provided showing areas without and with precipitate based upon the relative amounts of an anionic cellulosic thickener, poly(oxyethylene)sorbitan fatty acid ester surfactant, and multivalent cationic antiseptic represented by CHG. The bold open circles, the open circles, and the solid circles are as described in FIG. 1. For certain embodiments, the anionic cellulosic thickener, the poly(oxyethylene)sorbitan fatty acid ester surfactant, and multivalent cationic antiseptic are present in the instant compositions in amounts within the boundary defined by points A17, B17, C17, and D17, and along the boundary lines A17-B17, B17-C17, C17-D17, and D17-A17 in FIG. 17. The B17 point is established by running a straight line from the C17 point to the minimum amount of anionic compound (1.2%), keeping the level of multivalent cationic antiseptic constant. The amounts of the three components (% anionic compound/% solubilizing surfactant/% multivalent cationic antiseptic) with respect to each other at each of these points are as follows: A17=1.2/97.6/1.2; B17=1.2/89.0/9.8; C17=9.9/80.3/9.8; D17=18.5/80.3/1.2.

For certain embodiments, preferably for longer term stability the anionic cellulosic thickener, poly(oxyethylene)sorbitan fatty acid ester surfactant, and multivalent cationic antiseptic are present in the instant compositions in amounts within the boundary defined by points A17, E17, and F17, and along the boundary lines A17-E17, E17-F17, and F17-A17 in FIG. 17. The amounts of the three components (% anionic compound/% solubilizing surfactant/% multivalent cationic antiseptic) with respect to each other at each of these points are as follows: A17=1.2/97.6/1.2; E17=8.2/82.0/9.8; and F17=10.0/82.0/8.0.

Based upon the phase diagram of FIG. 17, in embodiments wherein the solubilizing surfactant is a poly(oxyethylene)sorbitan fatty acid ester surfactant as described above, the amounts of the three components with respect to each other may be expressed as follows for the present compositions without precipitate: at least 80% poly(oxyethylene)sorbitan fatty acid ester surfactant (PSFAS), less than 20% A, less than 10% MCA. For certain of these embodiments, for longer term stability the amounts of the three components are preferably: greater than 81% PSFAS, not more than 10% A, and less than 10% MCA; wherein at 83% or higher PSFAS the MCA is less than 9.8% but at least 8%, at greater than 85% PSFAS, the MCA is not more than 8.5% and not less than 7%, and at greater than 90% PSFAS, the MCA is not more than 7% but at least 5%.

For certain of these embodiments, the anionic cellulosic thickener is sodium carboxymethylcellulose. For certain embodiments, the pH of the composition is greater than 7 but not more than 9, preferably not more than 8.

For certain of these embodiments wherein the anionic compound is a phosphate, bicarbonate, dye, or cellulosic thickener salt, the poly(oxyethylene)sorbitan fatty acid ester comprises esters of (C12-C18) fatty acids. Preferably, for certain embodiments the poly(oxyethylene)sorbitan fatty acid ester includes at least 10 and not more than 40, more preferably at least 15 and not more than 30 or 25 repeating units of —CH$_2$CH$_2$—O—. For certain of these embodiments, the poly(oxyethylene)sorbitan fatty acid ester is a monoester, for example, polysorbate 20 or TWEEN 20.

Figure 18:
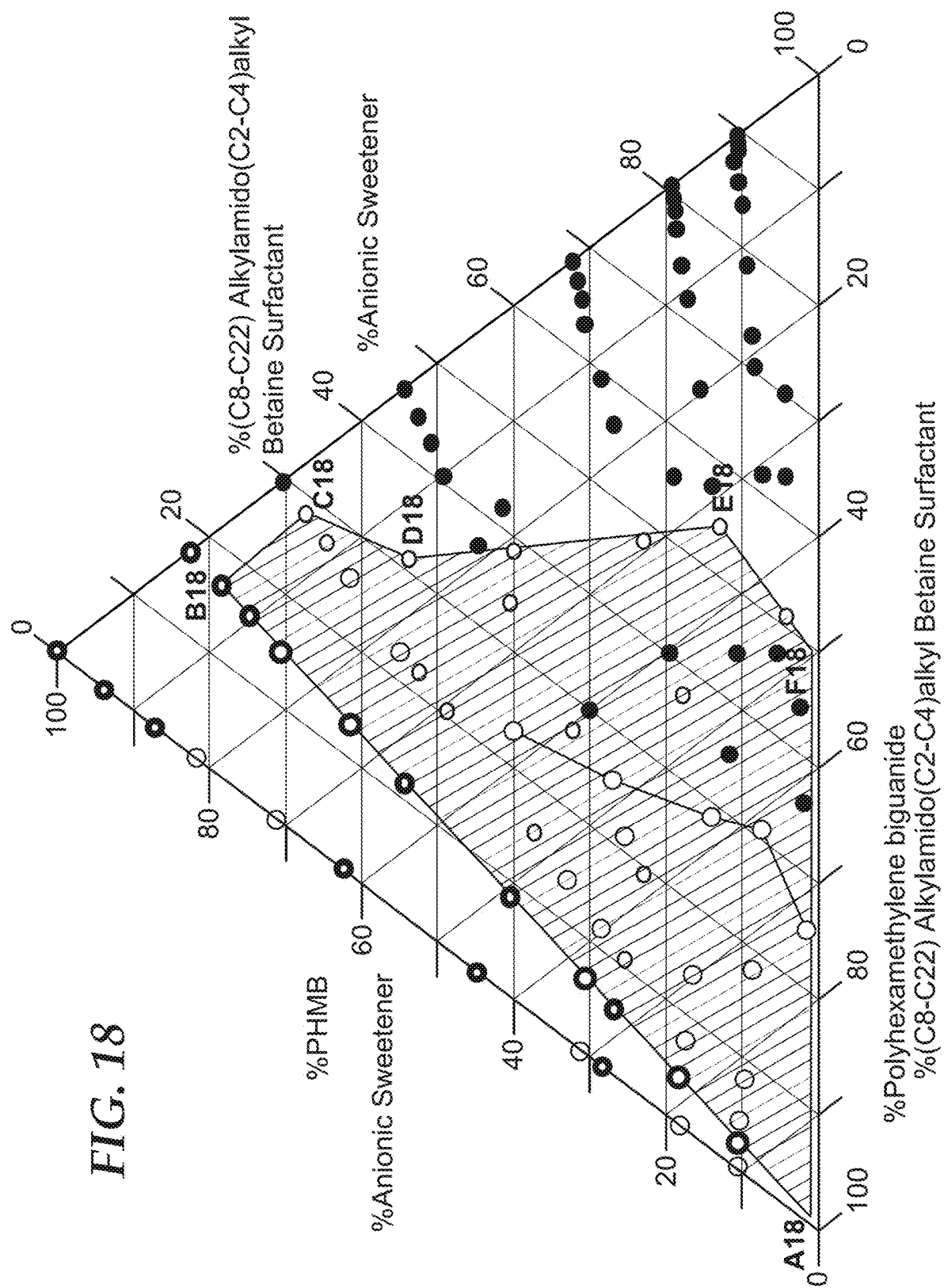
FIG. 18 is a phase diagram of % multivalent cationic antiseptic represented by poly(hexamethylene biguanide) (PHMB), % anionic sweetener, and % (C8-C22)alkylamido (C2-C4)alkyl betaine surfactant, showing regions without and with precipitate.
Figure 19:
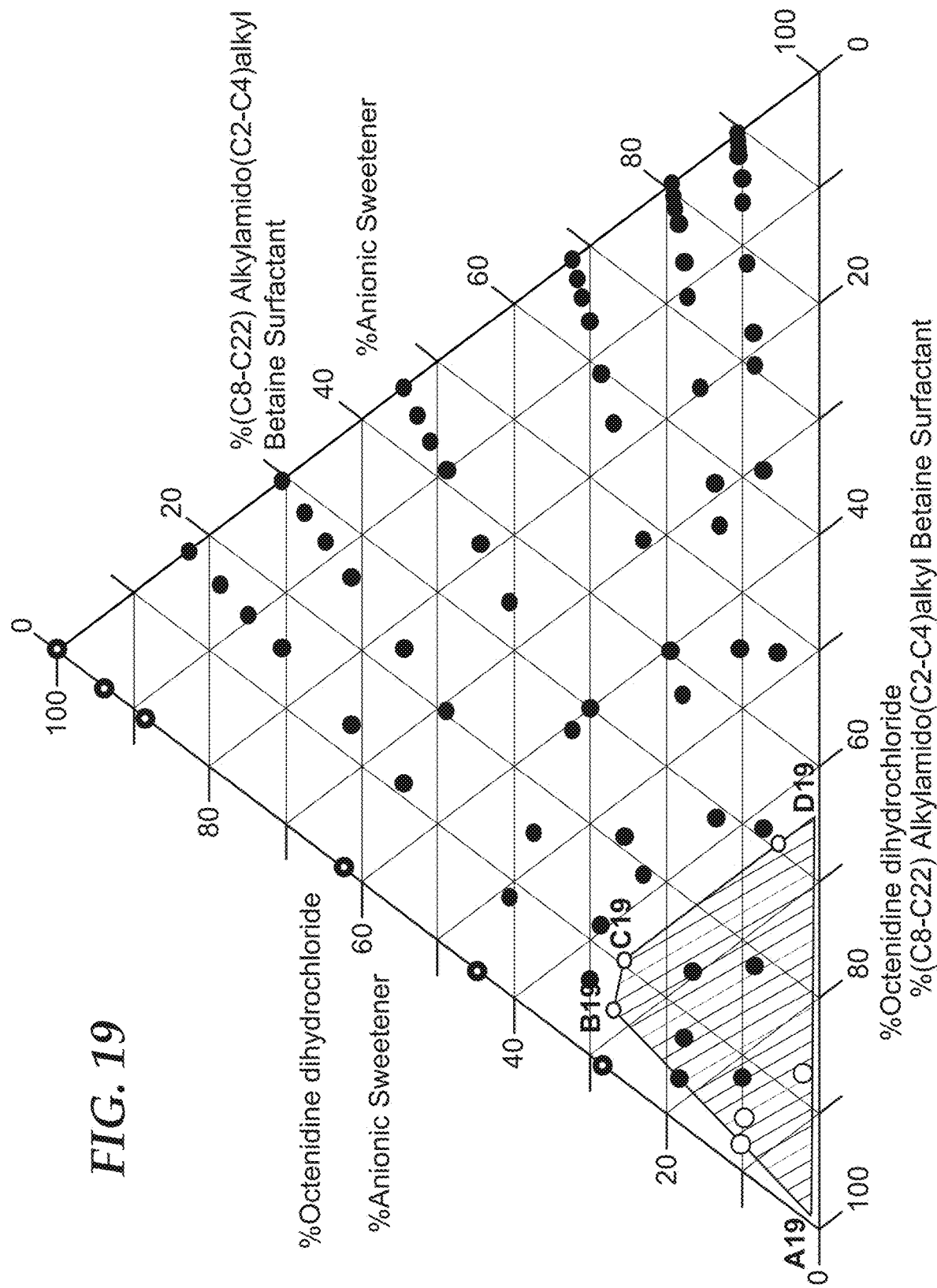
FIG. 19 is a phase diagram of % multivalent cationic antiseptic represented by octenidine, % anionic sweetener, and % (C8-C22)alkylamido(C2-C4)alkyl betaine surfactant, showing regions without and with precipitate.

Referring to FIG. 18, a phase diagram is provided showing areas without and with precipitate based upon the relative amounts of an anionic sweetener, (C8-C22) alkylamido(C2-C4)alkyl betaine surfactant, and multivalent cationic antiseptic represented by PHMB. The bold open circles, the open circles, and the solid circles are as described in FIG. 1. For certain embodiments, the anionic sweetener, (C8-C22) alkylamido(C2-C4)alkyl betaine surfactant, and multivalent cationic antiseptic are present in the instant compositions in amounts within the boundary defined by points A18, B18, C18, D18, E18, and F18, and along the boundary lines B18-C18, C18-D18, D18-E18, E18-F18, and F18-A18 in FIG. 18. The boundary line of A18-B18 is included in the area defined by the bold open circles. The amounts of the three components (% anionic compound/% solubilizing surfactant/% multivalent cationic antiseptic) with respect to each other at each of these points are as follows: A18=1.2/97.6/1.2; B18=16.6/4.2/79.2; C18=28.2/4.2/67.6; D18=31.0/15.0/54.0; E18=54.4/32.6/13.0; and F18=49.7/49.1/1.2.

Based upon the phase diagram of FIG. 18, in embodiments wherein the solubilizing surfactant is a (C12-C18) alkylamido(C2-C4)alkyl betaine surfactant as described above, the amounts of the three components with respect to each other may be expressed as follows for the present compositions without precipitate: at least 4.2% betaine surfactant (BS), less than 40% A, not more than 79.2%% MCA; and greater than 20% BS, not more than 54.4% A, and less than 40% MCA.

For certain of these embodiments, the (C8-C22)alkylamido(C2-C4)alkyl betaine comprises a (C12-C18)alkylamido(C2-C4)alkyl betaine, preferably a (C12-C18)alkylamidopropyl betaine. For certain of these embodiments, the anionic sweetener is sodium saccharin. For certain of these embodiments, preferably the poly(hexamethylene biguanide) is a hydrochloride salt.

Referring to FIG. 19, a phase diagram is provided showing areas without and with precipitate based upon the relative amounts of an anionic sweetener, (C8-C22) alkylamido(C2-C4)alkyl betaine surfactant, and multivalent cationic antiseptic represented by octenidine (dihydrochloride). The bold open circles, the open circles, and the solid circles are as described in FIG. 1. For certain embodiments, the anionic sweetener, (C8-C22) alkylamido(C2-C4)alkyl betaine surfactant, and multivalent cationic antiseptic are present in the instant compositions in amounts within the boundary defined by points A19, B19, C19, and D19, and along the boundary lines A19-B19, B19-C19, C19-D19, and D19-A19 in FIG. 19. The amounts of the three components (% anionic compound/% solubilizing surfactant/% multivalent cationic antiseptic) with respect to each other at each of these points are as follows: A19=1.2/97.6/1.2; B19=5.6/67.4/27.0; C19=10.7/63.8/25.5; and D19=34.9/63.9/1.2.

Based upon the phase diagram of FIG. 19, in embodiments wherein the solubilizing surfactant is a (C12-C18) alkylamido(C2-C4)alkyl betaine surfactant as described above, the amounts of the three components with respect to each other may be expressed as follows for the present compositions without precipitate: at least 63.8% betaine surfactant (BS), not more than 34.9% A, not more than 27.0% MCA.

For certain of these embodiments, the (C8-C22)alkylamido(C2-C4)alkyl betaine comprises a (C12-C18)alkylamido(C2-C4)alkyl betaine, preferably a (C12-C18)alkylamidopropyl betaine. For certain of these embodiments, the anionic sweetener is sodium saccharin. For certain embodiments, preferably the octenidine is a dihydrochloride salt.

For certain of these embodiments, the multivalent cationic antiseptic is a multifunctional biguanide such as a salt of chlorhexidine or PHMB. For certain of these embodiments, the multivalent cationic antiseptic is PHMB, for example, the hydrochloride salt of PHMB. When the multivalent cationic antiseptic is PHMB, for certain embodiment, the amount of anionic compound, for example, an anionic sweetener, is less than 55%, based upon the total weight of the anionic compound, the solubilizing surfactant and the PHMB.

Alternatively, for certain of these embodiments, the multivalent cationic antiseptic is a chlorhexidine disalt of acetate, gluconate, lactate, methosulfate ($CH_3OSO_3^-$), or combinations thereof. For certain of these embodiments, preferably the multivalent cationic antiseptic is chlorhexidine digluconate (CHG).

Compositions used in the present method and kit can be applied with a delivery device such as a squeeze bottle, a spray bottle, swabs, cloth, sponges, foams, bristle brush, and non-woven and paper products (e.g., paper towels and wipes), a dual- or multi-component delivery device, such as two or more tubes associated with a static mixer or the like, allowing two or more solutions to be delivered simultaneously, or a combination thereof. The composition may be applied to a catheter or an intubation device, which in effect may then be a delivery device. The delivery device may be used to deliver a significant portion of the antiseptic composition to the tissue, such as mucosal or oral tissue. By "significant portion" it is meant that enough composition is applied and allowed to remain on the tissue when applied in a dose, at a frequency, and in an amount sufficient to reduce or eliminate the microorganisms on or in the tissue.

The present compositions can be provided as a one-part, two-part, or multiple-part composition. As a one-part composition, the composition is free of precipitate resulting from interaction of the anionic component with the multivalent cationic antiseptic for at least two weeks, at least three months and preferably for at least six months.

As a two-part or multiple-part composition, the separate parts maintain physical and chemical stability. When the parts are combined just prior to application, no precipitation resulting from interaction of the anionic component with the multivalent cationic antiseptic occurs within the first 15 minutes and preferably within the first hour or longer. Preferably no visible precipitation occurs for 2 hours, more preferably 4 hours and most preferably 8 hours or longer. As such, the combined parts can be applied, and the multivalent cationic antiseptic can attach to the tissue and provide antimicrobial efficacy before precipitation, if any, with the anionic compound can occur. The added stability also allows the clinician to prepare the composition prior to the procedure and/or to use the combined composition multiple times throughout longer procedures such as surgical procedures or periodic procedures such as periodic oral rinsing, for example, with ventilated patients in an intensive care unit.

The present compositions exhibit good chemical stability. This can be a concern with compounds that may hydrolyze or undergo heat and/or light degradation such as chlorhexidine. The most preferred compositions retain an average of at least 97% of the antiseptic component after aging for 4 weeks at 40° C. in a sealed container beyond an initial 5-day equilibration period at 25° C. The percent retention is understood to mean the weight percent of antiseptic component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 25° C. for five days. The level of antiseptic component may be determined using known methods such as gas chromatography or high performance liquid chromatography using appropriate standards and controls.

The present compositions preferably exhibit good physical stable. As defined herein "physically stable" compositions are those that do not significantly change due to substantial precipitation, crystallization, phase separation, and the like, from their original ready to use condition until used. The amount of time will depend upon whether the composition is provided as a ready to use one-part composition or as a multiple part composition, the parts of which are combined just prior to application. The compositions are preferably physically stable for at least two weeks, more preferably at least 3 months or 6 months. Particularly preferred compositions are completely physically stable if a 10-milliliter (10-ml) sample of the composition when placed in a 15-ml conical-shaped graduated plastic centrifuge tube (Corning) and centrifuged at about 2275×g (e.g. 3,000 revolutions per minute (rpm) for 10 minutes using a Labofuge B, model 2650 manufactured by Heraeus Sepatech GmbH, Osterode, West Germany) or similar centrifuge at a centrifugal force of 2275×g has no visible phase separation in the bottom or top of the tube. Phase separation of less than 0.5 ml is also considered stable as long as there is no other sign of physical separation in the sample.

In another alternative, the parts of the two-part or multiple-part composition are not combined with each other prior to application. In this case each part is applied separately to the tissue, allowing one part to be applied a small number of times and the second or other parts to be applied a greater number of times. In one example, a first part comprises the multivalent cationic antiseptic, and a second part comprises the anionic compound, with the surfactant included in the first part, the second part, or both. The second part may be a moisturizer composition. The first part is applied, and then the second part is applied. In this case, no precipitation resulting from interaction of the anionic component with the multivalent cationic antiseptic occurs on the tissue within the first 15 minutes and preferably within the first hour or longer. As such, the combined parts can be applied, and the multivalent cationic antiseptic can attach to the tissue and provide antimicrobial efficacy before precipitation, if any, on the tissue with the anionic compound can occur.

In the present methods, the multivalent cationic antiseptic is applied as a composition comprising a solution of the multivalent cationic antiseptic. For certain embodiments, the solution is an aqueous solution or a water/alcohol solution of the antiseptic. Alternative compositions where the multivalent cationic antiseptic is dissolved in or mixed with a non-aqueous hydrophilic material are also contemplated.

Compositions which are to act as a moisturizer may be used or provided in various forms including, for example, hydrophobic ointments, oil in water emulsions, water in oil emulsions, thickened aqueous gels, and hydrophilic gels.

Hydrophobic compositions include a hydrophobic base or vehicle (e.g., petrolatum, insoluble oils, thickened or gelled water insoluble oils and the like) and may include a minor amount of a water-soluble phase, which would include the multivalent cationic antiseptic if present. Acceptable salts, surfactants, emulsifiers, humectants and/or other components may also be included. Care must be taken to ensure that the composition does not degrade or negatively affect any medical device to which the composition is applied, such as an endotracheal tube used for ventilation or other medical devices that may be in contact with or in proximity to mucosal tissue. Certain hydrophobic components can degrade plasticized PVC which is commonly used as endotracheal tube material. Preferably the compositions do not negatively affect natural rubber latex or nitrile gloves.

Oil in water emulsion compositions include a discrete phase of a hydrophobic component and a continuous aqueous phase comprising water and optionally one or more polar hydrophilic carriers, where either or both phases include the multivalent cationic antiseptic if present. Acceptable salts, surfactants, emulsifiers, humectants, and/or other components may also be included. These emulsions may comprise acceptable water-soluble or water swellable polymers as well as one or more emulsifiers that help to stabilize the emulsion.

Water in oil emulsion compositions include a continuous phase of a hydrophobic component and an aqueous phase comprising water and optionally one or more polar hydrophilic carriers as well as acceptable salts or other components, where the multivalent cationic antiseptic if present is in either or both phases. Acceptable salts, surfactants, emulsifiers, humectants and/or other components may also be included. These emulsions may comprise oil soluble or oil swellable polymers and one or more emulsifiers, as well as inorganic salts such as magnesium sulfate, that help to stabilize the emulsion.

Thickened aqueous gel compositions include an aqueous phase, which would include the multivalent cationic antiseptic if present, that has been thickened to achieve a sufficiently high viscosity as described above, for example, a viscosity of at least 10 cps and preferably at least 20 cps. Viscosities of at least 50 cps, at least 100 cps, at least 250 cps, or at least 500 cps may also be preferred. The viscosity can be determined using conventional methods. These compositions are thickened by suitable natural, modified natural, or synthetic polymers. The thickened aqueous gels can also be thickened using suitable emulsifiers such as alkyl alcohols and polyethoxylated alkyl chain surfactants that effectively thicken the composition. Examples include the Polawax, Behenyl TMS, Crodaphos CES, Cosmowax, and Crothix systems from Croda Inc.

Hydrophilic gel compositions include a continuous phase comprised of at least one water soluble hydrophilic component other than water. These formulations may contain water up to 90% by weight. The higher concentrations may be suitable in some compositions. Suitable hydrophilic components are described below. For certain embodiments, suitable hydrophilic components include one or more glycols (such as glycerin, propylene glycol, butylenes glycol, etc.), polyethylene glycols (PEG), random or block copolymers of ethylene oxide, propylene oxide, and/or butylenes oxide, polyalkoxylated surfactants having one or more hydrophobic moieties per molecule, silicone copolyols, as well as combinations thereof. One skilled in the art will recognize that the level of ethoxylation must be sufficient to render the hydrophilic component water-soluble or water dispersible at 23° C.

The present compositions may include at least one additional component selected from the group consisting of enhancers, surfactants, hydrophilic compounds, hydrophobic compounds, and combinations thereof.

Enhancers increase the antimicrobial effectiveness of the antiseptic, although alone may not provide any appreciable antimicrobial activity. The activity enhancement may be especially useful against Gram negative bacteria, such as *E. coli* and *Psuedomonas* sp. The enhancer chosen preferably affects the cell envelope of the bacteria, for example, by allowing the antiseptic to more easily enter the cell cytoplasm and/or by facilitating disruption of the cell envelope. The enhancer component may include an alpha- or beta hydroxyl carboxylic acid, a (C1-C4)alkyl carboxylic acid, a (C6-C12)aryl or (C6-C12)aralkyl carboxylic acid, a chelator, a phenolic compound (such as certain antioxidants and parabens), a (C1-C10)monohydroxy alcohol, a glycol ether (i.e., ether glycol), and combinations thereof. Useful enhancers are further described in U.S. Patent Application Publication No. 2006/0051385.

In addition to the surfactants included in the present compositions, which prevent precipitation of the multivalent cationic antiseptic in the presence of a precipitating anionic compound, one or more additional surfactants may be used to emulsify the composition and to help the composition wet the surface and/or to aid in contacting the microorganisms. As used herein the term "surfactant" means an amphiphile capable of reducing the surface tension of water and/or the interfacial tension between water and an immiscible liquid. The additional surfactant can be cationic or nonionic (e.g., poloxamers). Combinations of surfactants can be used if desired. Such surfactants are further described in U.S. Patent Application Publication No. 2006/0051385.

The present compositions can include a hydrophilic or water-soluble component to help solubilize and/or physically stabilize the antiseptic and/or enhancer component in the composition and/or to enhance the antimicrobial efficacy and/or the speed of antimicrobial efficacy. The incorporation of a sufficient amount of a hydrophilic component in a hydrophobic ointment may provide significantly better antimicrobial activity both in terms of speed of kill and extent of kill. While not intended to be bound by theory it is believed that the incorporation of the hydrophilic component allows more antiseptic to be available at the surface or to more rapidly diffuse to the surface of the ointment during use. Certain compositions may be solutions, emulsions (one liquid/gel/paste dispersed in another liquid/gel/paste), or dispersions (solid in liquid/paste/gel). In general, for improved antimicrobial activity the ratio of total hydrophilic component to total hydrophobic component (water insoluble ingredients) should be at least 5:95 wt/wt, preferably at least 10:90 wt/wt, more preferably at least 15:85 wt/wt and most preferably at least 20:80 wt/wt. Levels as high as 30:70, 40:60, 50:50 wt/wt of total hydrophilic component to total hydrophobic component (water insoluble ingredients) or higher may be appropriate for certain compositions.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols. Such hydrophilic components are further described in U.S. Patent Application Publication No. 2006/0051385.

The present compositions may also include one or more hydrophobic materials. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of hydrophobic components useful in the present composition include those selected from the group consisting of vegetable oils, (C6-C22)alkyl mono, di and tri esters of glycerin and propylene glycol, petrolatum USP and short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12)diacids or (C4-C12)diols optionally substituted in available positions by —OH (such as diisopropyladipate, diisopropylsebacate); (C1-C9)alkyl or (C6-C12) aryl esters of glycerol, pentaerythritol, ethylene glycol, propylene glycol (such as glyceryl tricaprylate/caprate); and mixtures thereof. For certain embodiments, preferably the hydrophobic component is selected from one or more vegetable oils, (C6-C22)alkyl mono, di and tri esters of glycerin and diesters of propylene glycol, and combinations thereof. Such hydrophobic components are further described in U.S. Patent Application Publication No. 2006/0051385.

The present compositions may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, steroids, non-steroidal antiinflammatory agents, or other anti-inflammatory agents), antiplaque, antigingivitis, antibiofilm, or may contain materials useful in physically formulating various dosage forms of the present invention, such as excipients, flavors, vitamins, dyes, perfumes, fragrances, lubricants, thickening agents, stabilizers, tissue penetration enhancers, preservatives, or antioxidants.

With some tissues, saliva and/or mucus secretions as well as other medicaments or compositions that may be administered are present. Here the present compositions are preferably substantive to resist being washed or dislodged from the tissue for a period of time. Preferably at least a portion of the present composition remains at the site of application for at least 1 hour, at least 2 hours, or more preferably at least 4 hours. Substantivity may be evaluated using known methods, for example, as described at pages 75-76 in International Publication No. WO 2010/129795A1. Relatively high viscosities are preferred to reduce migration as well as to provide substantivity (resistance to removal by fluids). Preferably the composition has a viscosity of at least 20 centipoise (cps), preferably at least 50 cps, preferably at least 100 cps, more preferably at least 500 cps. For certain embodiments, the composition has a viscosity of at least 1,000 cps, more preferably at least 10,000 cps. Other preferred compositions have viscosities of at least 20,000 cps, more preferably in excess of 50,000 cps. For certain embodiments, the viscosity can be at least 100,000 cps or even at least 1,000,000. These viscosities can be conveniently measured using known methods, for example, as described at page 68 in International Publication No. WO 2010/129795A1. Compositions meet these viscosity values at 22-25° C., and in certain embodiments even after heating to 32° C., 35° C. or as high as 37° C., so that when in contact with mammalian tissue the compositions remain substantive. For certain of these embodiments, preferably the composition includes a hydrophobic component (e.g., as described below) and/or a polyhydroxy compound and can be spread evenly across the tissue. Preferably the composition wets the tissue in order to easily coat the tissue without dewetting. This can help achieve substantivity. Wetting can be achieved by adjusting the vehicle components and/or addition of surfactant(s).

As noted above, certain anionic thickeners, such as anionic cellulosic thickeners, can be used in the present compositions to provide the desired viscosity. Further enhancements in substantivity of the compositions can be obtained with polycationic polymers. These are not only compatible with the multivalent cationic antiseptic and improve retention by increasing viscosity, but they also may increase retention or substantivity by ionically binding with the oral tissue.

Retention may also be increased using hydrophobic water insoluble components. For example, high oil in water emulsions or water in oil emulsions can resist removal from mucosal tissue due to the water insoluble nature of the oil. Suitable oils include any of the hydrophobic emollients and emulsifiers disclosed in U.S. Pat. No. 6,562,360. Emollients and emulsifiers that are approved for use as food additives are particularly preferred in the oral cavity. For example, C8 to C18 mono-, di- and tri-esters of glycerin and propylene glycol may be used as well as a variety of edible oils such as vegetable oils.

In some embodiments an oral care kit may be provided. The oral care kit includes at least one dose of the multivalent cationic antiseptic composition. One dose is an amount sufficient for application to cover at least a portion of the oral tissue of a subject, preferably all of the oral mucosal tissue of a subject. For certain embodiments, one dose is 1 to 15 mL of the antiseptic composition. For certain embodiments, preferably the kit includes at least 15 or 30 mL of the multivalent cationic antiseptic composition. For certain of these embodiments, the kit includes at least two 15 mL unit dose containers of the multivalent cationic antiseptic composition. Although the amounts are expressed in mL units, these amounts are understood to include their mass equivalents. For example, 1 mL of the multivalent antiseptic composition is equivalent to an amount of 0.9 to 1.1 grams, depending upon the particular formulation density. In the case of the composition being in the form of a foam, the amount in grams may be less than this.

Subjects who may benefit from the present compositions and kits, which include a moisturizer component or moisturizing composition, include any who have a condition of dry tissue or dry oral tissue. Included among these are mechanically ventilated patients and those in an Intensive Care Unit, such as those in a hospital setting, who may receive significantly improved care with the present compositions.

For certain embodiments, the oral care kit includes a moisturizing composition supplied in an amount sufficient to cover at least a portion of the oral tissue of a subject, preferably all of the oral mucosal tissue of a subject, more preferably also including the lips. For certain of these embodiments, the moisturizing composition is supplied in an amount sufficient for at least one application to the oral tissue of the subject at 1 to 10 grams per application. Preferably, the moisturizing composition is supplied in an amount sufficient for at least 4 applications to the oral tissue of the subject at 1 to 10 grams per application, for example, at least 4 unit dose packages of 1 to 10 grams per package.

Significantly improved flexibility is provided by the oral care kit for applying the moisturizer composition whenever a subject is in need of an additional application. For example, some patients have significantly drier mouths than others and may benefit from more frequent applications of the moisturizer or substantive moisturizer composition. For certain embodiments, preferably the moisturizing composition is supplied in a single container, for example, in an amount sufficient for at least 4 separate applications to all of the oral mucosal tissue and lips of a subject.

Subjects who are unable to clean their oral tissue, such as ventilated patients, are in need of periodic oral tissue cleaning. This can be carried out using a de-briding composition, such as a hydrogen peroxide composition. Oral debriding refers to removal of plaque and calculus from the teeth but also may assist in breaking down thick mucous in the oral cavity that is otherwise difficult to remove. For certain embodiments, the oral care kit further comprises a de-briding composition, which in one embodiment comprises hydrogen peroxide. Preferably, the hydrogen peroxide is stabilized, for example with a stabilizing component which maintains the de-briding composition at a pH of 2.5 to 4, preferably 2.8 to 3.8. A buffer component may be used, such as monovalent alkyl carboxylic acids and alkyl phosphoric acids wherein the alkyl group optionally comprises a carbon chain substituted with or interrupted by one or more N, O, or S atoms; polyalkoxylated derivatives such as phosphate or carboxylate terminated polyethoxylated and/or propoxylated alkyl alcohols; alpha-hydroxy acids such as lactic acid, gluconic acid, citric acid (when used at a pH where only one acid group is ionized); amino acids; phosphoric acid; and boric acid. Such buffer components are selected and used at concentrations with the surfactant present such that a precipitate is not formed when the buffer component is combined with or brought into contact with the multivalent cationic antiseptic. Preferred acids have only substantially a single acid group at least partially ionized at pH 3.5. For example, phosphoric acid is useful since it has pKa values of 2.15, 7.2, and 12.35. Thus, at pH 3.5 there is predominantly a single ionized group. Preferably, the buffer has a pKa less than 3.5, and if it comprises a second acid functionality the second pKa is greater than 4.5 as determined by standard potentiometric titration.

The de-briding composition may further include a sweetener such as an anionic sweetener (e.g., sodium saccharin) and/or other sweeteners including, for example, sucralose, aspartame, sugars and sugar alcohols including but not limited to xylose, sucrose, maltose, mannose, glucose, xylitol, sorbitol, mannitol, erythritol, maltitol, lactitol, and a combination thereof.

The de-briding composition is supplied in an amount sufficient for at least one application to the oral tissue of the subject. The de-briding composition may be supplied in at least 4 unit dose containers, each containing an amount sufficient for a single application to the oral tissue of the subject, or in a single container in an amount sufficient for at least 4 applications to the oral tissue of the subject.

The oral care kit may further comprise an additional oral care composition selected from the group consisting of an oral rinse, a toothpaste, a lip care composition, a mouth care composition, and combinations thereof. A mouth care composition may include an analgesic, wound healing paste, tooth care composition, or other oral composition.

The presently provided oral care kit comprises the antiseptic composition and a delivery device. The delivery device may be one or a plurality of applicator tools for applying at least one composition to tissue (e.g., oral tissue) of a subject. Examples include swabs, suction swabs, toothbrushes, suction toothbrushes, and combinations thereof. The kit may further include a written protocol for treating oral tissue of a subject. At least a portion of the applicator tools may be packaged so that usage of at least a portion of the applicator tools shows compliance with at least a portion of a protocol for treating the oral tissue of a subject. For example, removal of a tool from a particular section of the kit indicates that an application of a particular composition was carried out within a particular time frame. At least a portion of the applicator tools may be packaged with an indication of at least one time frame for applying at least one composition comprising the kit. The indication may be a color code, a symbol, a picture, or a printed number.

For certain embodiments, the oral care kit comprises a plurality of packages, wherein each package contains at least one kit component selected from the group consisting of an applicator tool, a suction yankaeur, a suction catheter, a Y-connector, a vacuum adapter handle, a multivalent cationic antiseptic composition, a moisturizing composition, a de-briding composition, other mouth care products, and combinations thereof. For certain of these embodiments, the package is a bag, a box, a tray, or a combination thereof.

As indicated above, there is provided a method of decolonizing mucosal tissue comprising contacting the mucosal tissue with the antiseptic composition. This may be carried out using the compositions and delivery devices provided in the kit and/or utilizing any of the embodiments described herein. For certain of these embodiments, the tissue is oral tissue.

Similarly, there is provided a method of decontaminating wound tissue by contacting the wound tissue with the antiseptic composition. This may also be carried out using the compositions and delivery devices provided in the kit and/or utilizing any of the embodiments described herein. For certain of these embodiments, the wound tissue is an acute surgical wound or a chronic wound, and the composition is used to irrigate the surgical or chronic wound or to debride the chronic wound. An acute surgical wound includes an incision.

The present antiseptic compositions may also be suitable for killing microorganisms on medical devices, including any device used to treat or which contacts animal tissue. This is considered a pretreatment as it is carried out prior to contacting the tissue with the antiseptic composition using the device. Therefore, there is also provided a method of pretreating a medical device by contacting the device with the antiseptic composition.

As indicated above, methods of preparing the present antiseptic compositions are provided herein. Such methods enable preventing or significantly retarding (delaying) precipitation of the multivalent cationic antiseptic in the presence of a precipitating anionic compound via the presence of the solubilizing surfactant when combining the antiseptic and anionic compound. These methods can also enable reversing the precipitation by adding the solubilizing surfactant to the mixture of antiseptic and anionic compound which already contains precipitated antiseptic.

Objects and advantages of this invention are further illustrated by the following examples, but the particular materials and amounts thereof recited in these examples, as well as other conditions and details, should not be construed to unduly limit this invention.

EXAMPLES

Example Components

| Trade Name/ Abbreviation | Description | Source | Location |
|---|---|---|---|
| SURFACTANTS | | | |
| AMMONYX LMDO | Laurylamidopropyldimethylamine oxide; 33 wt. % active (an amine oxide surfactant) | Stepan Company | Northfield, IL, USA |
| BRIJ 78 | poly(oxyethylene) 20 octadecyl ether (a micelle-forming nonionic surfactant) | Sigma-Aldrich Company | Milwaukee, WI, USA |
| CANARCEL TW 62 | Poly(oxyethylene) 40 sorbitan diisostearate (a micelle-forming nonionic surfactant) | Kraft Chemical Company | Melrose Park, IL, USA |
| DECAGLYN 1M | Polyglyceryl-10 Myristate (a micelle-forming nonionic surfactant) | Barnet Products Corp | Englewood Cliffs, NJ, USA |
| GLUCOPON 225DK | (C8-C10) fatty alcohol ether of mono and oligoglucopyranosides; 70 wt. % actives (a micelle-forming nonionic surfactant) | BASF Corporation | Florham Park, NJ, USA |
| TRITON X-100 | Polyethylene glycol p-(1,1,3,3-tetramethylbutyl)-phenylether (a micelle-forming nonionic surfactant) | DOW-Union Carbide Corp | Danbury, CT, USA |
| PLANTACARE 818 UP | Alkylpolyglucosides (a micelle-forming nonionic surfactant) | Cognis | Cincinnati, OH, USA |
| TRYLOX | 5906(CO-30) POE(30) Ethoxylated castor oil (a micelle-forming nonionic surfactant) | Cognis | Cincinnati, OH, USA |
| TWEEN 20 | Polyethylene glycol 20 sorbitan monolaurate (a micelle-forming nonionic surfactant) | Sigma-Aldrich Company | Milwaukee, WI, USA |
| LECITHIN | Refined from soybean, [(2R)-2,3-di(tetradecanoyloxy)propyl] 2-(trimethylazaniumyl)ethyl phosphate (a zwitterionic surfactant) | Alfa Aesar | Pelham, NH, USA |
| MACKAM L | Cocamidopropyl Betaine; 30 wt. % active (a zwitterionic surfactant) | McIntyre Group LTD. | University Park, IL, USA |
| MACKAM 50-SB | Cocamidopropylhydroxysultaine; 43 wt. % active (a zwitterionic surfactant) | McIntyre Group LTD. | University Park, IL, USA |
| CPC | Cetylpyridinium chloride (a cationic surfactant) | Sigma-Aldrich Company | Milwaukee, WI, USA |
| PEG400 | Polyethylene glycol 400 | ChemCentral | Chicago, IL, USA |
| MULTIVALENT CATIONIC ANTISEPTICS | | | |
| CHG | Chlorhexidine Digluconate 20% USP | American International Chemical Inc. | Framingham, MA, USA |
| PHMB | Polyhexamethylene biguanide, available as COSMOCIL 100, 20% wt/wt aqueous solution | Lonza Inc. | Allendale, NJ, USA |
| OCT | Octenidine HCl | Dishman Pharmaceuticals | Ahmedabad, India |
| ANIONIC COMPOUNDS | | | |
| CARBOPOL 954 | Polyacrylic acid | BF Goodrich Co. | Cleveland, OH, USA |
| FD&C RED 40 | Disodium 6-hydroxy-5-((2-methoxy-5-methyl-4-sulfophenyl)azo)-2-naphthalenesulfonate | Whittaker (Brenntag) | South Plainfield, NJ, USA |
| Hyaluronic acid, potassium salt | Poly($\beta$-glucuronic acid-[1→3]-$\beta$-N-acetylglucosamine-[1→4], alternating | Sigma Aldrich Company | St. Louis, MO, USA |
| LUBRAJEL NP | Glycerin (and) Glyceryl Acrylate/Acrylic Acid Copolymer | ISP | Wayne, NJ, USA |
| Na2HPO4 | Disodium Phosphate | Sigma Aldrich | St. Louis, MO, USA |
| NaHCO3 | Sodium Bicarbonate | EM Science | Cherry Hill, NJ, USA |
| NaSaccharin | Benzoic Sulfimide Sodium Salt | Alfa Aesar | Pelham, NH, USA |
| NaH2PO4 | Sodium dihydrogen phosphate | Sigma-Aldrich Company | Milwaukee, WI, USA |

-continued

| Trade Name/ Abbreviation | Description | Source | Location |
|---|---|---|---|
| NaCMC | Sodium carboxymethyl cellulose | Fisher Scientific | Fair Lawn, NJ, USA |
| FD&C Yellow No. 6 | Disodium 6-hydroxy-5-[(4-sulfophenyl)azo]-2-naphthalenesulfonate | Chromatech Incorporated | Canton MI |

Test Method A—Precipitation Test

Example test solutions were observed for the formation of a precipitate in the prepared formations when the multivalent cationic antiseptic (e.g. CHG) was mixed with an anionic compound (optionally) in the presence of the selected surfactants.

STEP 1. Anionic Compound Solution

An amount of 2.5 grams of sodium saccharin (or other anionic compound) was added to 97.5 grams of water. For solutions of sodium bicarbonate the pH was either 9.1 or was adjusted with 1M HCl to pH 7. The disodium phosphate solution was pH adjusted to 7, and the sodium dihydrogen phosphate solution was pH adjusted up to pH 6.5 with 1M NaOH.

STEP 2. Surfactant Solution

An amount of 10 grams of surfactant material was added to 40 grams of water. The surfactant material was used "as is" as received from the supplier. For some surfactants the weight percent of active material is less than 100% of the material as received. Therefore, in the case of MACKAM L (30 wt. % active), MACKAM 50-SB (43 wt. % active), AMMONYX LMDO (33 wt. % active), and GLUCOPON 225DK (70 wt. % active), the percent active was taken into account to calculate the final weight percent of active surfactant reported in the Examples tables below. The prepared surfactant solution was left to roll for an hour at 60 rpm to ensure dissolution of the surfactant.

STEP 3. To an amount of the 2.5% Anionic Compound Solution was added a calculated amount of water and a calculated amount of the surfactant solution of STEP 2. This was shaken to ensure proper mixing. The total weight of the solution at this point was 9.88 grams. The appropriate amounts of solutions added were calculated to achieve the target concentrations described in the Examples below.

STEP 4. An amount of 0.12 grams of a 20% aqueous solution of CHG or other multivalent cationic antiseptic was added to the solution of STEP 3, to bring the total weight to 10 grams and bring the anionic compound, surfactant and CHG to their respective target concentrations. This solution was shaken to ensure mixing and then observed initially, and at a 15 minute (or other time periods as noted). The confirmed observation of a precipitate designated "yes," included visually observing either a solid precipitate or cloudiness to the overall solution. If no precipitate was observed the result was "no."

STEP 5. (OPTIONAL) For some Examples in Tables A-P, observations of precipitate in Example solutions were also conducted for "Long Term" stability after at least two weeks of letting the solutions stand at room temperature and ambient conditions.

NOTE: The order of addition was: anion, surfactant, cationic antiseptic. Additionally, as noted in the Examples below, the final concentrations of cationic antiseptic, the surfactant, and the anionic compound were changed to achieve various target final concentrations. Unless otherwise stated, water comprised the remaining percentage of each sample formulation. All percentages are in weight percent unless otherwise noted.

Test Method B—Antimicrobial Efficacy Test

An overnight suspension of $10^8$ cfu/ml of *Staphylococcus aureus* (methicillin-resistant *Staphylococcus aureus*, ATCC® 33592™) was prepared in BD Tryptic Soy Broth (TSB), available from BD Diagnostic Systems of Sparks, Md., USA; and diluted 1:10 in PBW (phosphate buffered water). This became the working innoculum. In triplicate, an amount of 3 mL of each test Example was placed in 15 mL tubes. A recovery control was also prepared by using 3 mL of PBW in place of the test Example. An amount of 120 µL working innoculum was added to each of the 15 mL tubes containing the Examples and likewise the control. The inoculated Examples were vortexed and allowed to stand at ambient temperature for 5 minutes. After 5 minutes, 1 mL of each inoculated Examples was placed in 20 mL of BD Difco™ Neutralizing Buffer, available from BD Diagnostic Systems.

Serial dilutions of 1:10 were prepared from neat through 1:10,000 by serial pipetting 1 mL of sample into 9 mL of Butterfield's phosphate buffer. Each dilution (including the neat solution) was plated in duplicate by pipetting 1 mL of sample onto 3M PETRIFILM AEROBIC COUNT PLATES, 3M Company. All plates were incubated at 35-37° C. for 24 hours. Plates were counted with a PETRIFILM PLATE READER (available from 3M Company of St. Paul, Minn.), and confirmed manually. Colony Forming Units (CFU) were counted, duplicate plates averaged and multiplied by the dilution factor for CFU/mL, and multiplied by the total test volume after neutralization for the CFU/test sample. The number of colonies recorded were reported as Log(10) Recovery. In some instances Log(10) Reduction was also calculated and reported. Log Reduction is calculated by subtracting the Log(10) Recovery from the Log(10) input control.

Example 1

The following samples of Example 1 were prepared and tested as described above in TEST METHOD A—PRECIPITATION TEST and the TEST METHOD B—ANTIMICROBIAL EFFICACY TEST. For each sample a "placebo" was also prepared in similar fashion using the same stock solution of sodium saccharin and surfactant from STEPS 1-2 except water was substituted for CHG solution. No precipitate was observed in the placebos. It was observed that solutions prepared with final concentrations of 0.2% sodium saccharin and 0.12% CHG, but without surfactant resulted in precipitation. Example 1 was conducted to demonstrate the addition of the appropriate surfactant will prevent that precipitation. Before the addition of CHG in STEP 4 of the samples of Example 1, all solutions were clear and free of precipitate. Samples were observed for precipitation (PPT) initially, which was immediately after the CHG was added and then again later, 30 minutes after the CHG was added.

TABLE 1

EXAMPLE 1

| EX. 1 | Sodium Saccharin Final wt % | Surfactant Final wt % | CHG Final wt % | pH Initial | PPT Initial | PPT @ 30 min | Log Reduction |
|---|---|---|---|---|---|---|---|
| EX. 1-1 | 0.2 | 0.5% TRITON X100 | 0.12 | 7.3 | no | no | 5.6 |
| EX. 1-2 | 0.2 | 0.5% TWEEN 20 | 0.12 | 7.8 | no | no | 5.6 |
| EX. 1-3 | 0.2 | 0.5% Castor Oil | 0.12 | 7.4 | no | no | 5.6 |
| EX. 1-4 | 0.2 | 0.5% MACKAM L (0.15 wt. % active) | 0.12 | 7.9 | no | no | 5.6 |
| EX. 1-5 | 0.2 | 0.5% CANARCEL | 0.12 | 7.4 | no | no | 3.5 |
| EX. 1-6 | 0.2 | 0.5% PLANTACARE | 0.12 | 7.6 | no | no | 5.6 |
| EX. 1-7 | 0.2 | 0.5% PEG400 | 0.12 | 7.7 | yes | yes | 0.4 |
| EX. 1-C1 Control #1 | 0 | 0 | 0.12 | 8.3 | no | no | 5.4 |
| EX. 1-C2 Control #2 | 0.2 | 0 | 0.12 | 8.4 | yes | yes | 0.4 |

Examples 2A-2C

The following samples of Example 2 were prepared and tested as described above in TEST METHOD A—PRECIPITATION TEST to evaluate a range of concentrations of the surfactant CANARCEL and precipitate causing anion, sodium saccharin in the presence of CHG at 0.06%, 0.12%, and 0.24%. Comparative examples designated with the suffix: C1, C2, C3, etc., are those in which precipitation DOES NOT occur because there is not enough sodium saccharin to cause precipitation with the CHG or are comparative examples in which precipitation DOES occur because there is not enough surfactant (CANARCEL) to counteract the precipitating effect of the sodium saccharin.

TABLE 2A

EXAMPLE 2A

| EX. 2A | NaSaccharin Final wt % | CANARCEL Final wt % | CHG Final wt % | PPT Initial | PPT after 1 hr. |
|---|---|---|---|---|---|
| EX. 2A-C1 | 0.05 | 0.00 | 0.24 | no | no |
| EX. 2A-C2 | 0.10 | 0.00 | 0.24 | yes | yes |
| EX. 2A-1 | 0.10 | 0.05 | 0.24 | no | no |
| EX. 2A-2 | 0.10 | 0.10 | 0.24 | no | no |
| EX. 2A-3 | 0.10 | 2.00 | 0.24 | no | no |
| EX. 2A-C3 | 0.20 | 0.05 | 0.24 | yes | yes |
| EX. 2A-C4 | 0.20 | 0.10 | 0.24 | yes | yes |
| EX. 2A-4 | 0.20 | 0.50 | 0.24 | no | no |
| EX. 2A-5 | 0.20 | 2.00 | 0.24 | no | no |
| EX. 2A-C5 | 0.50 | 0.10 | 0.24 | yes | yes |
| EX. 2A-C6 | 0.50 | 0.50 | 0.24 | yes | yes |
| EX. 2A-6 | 0.50 | 1.00 | 0.24 | no | no |
| EX. 2A-7 | 0.50 | 2.00 | 0.24 | no | no |
| EX. 2A-C7 | 1.00 | 0.50 | 0.24 | yes | yes |
| EX. 2A-8 | 1.00 | 1.00 | 0.24 | no | no |
| EX. 2A-9 | 1.00 | 2.00 | 0.24 | no | no |
| EX. 2A-C8 | 2.00 | 0.50 | 0.24 | yes | yes |
| EX. 2A-10 | 2.00 | 1.00 | 0.24 | no | no |
| EX. 2A-11 | 2.00 | 2.00 | 0.24 | no | no |

TABLE 2B

EXAMPLE 2B

| EX. 2B | NaSaccharin Final wt % | CANARCEL Final wt % | CHG Final wt % | PPT Initial | PPT after 1 hr. |
|---|---|---|---|---|---|
| EX. 2B-C1 | 0.10 | 0.00 | 0.12 | no | no |
| EX. 2B-C2 | 0.20 | 0.00 | 0.12 | yes | yes |
| EX. 2B-C3 | 0.20 | 0.05 | 0.12 | yes | yes |
| EX. 2B-1 | 0.20 | 0.10 | 0.12 | no | no |
| EX. 2B-2 | 0.20 | 2.00 | 0.12 | no | no |
| EX. 2B-C4 | 0.50 | 0.10 | 0.12 | yes | yes |
| EX. 2B-3 | 0.50 | 0.50 | 0.12 | no | no |
| EX. 2B-4 | 0.50 | 2.00 | 0.12 | no | no |
| EX. 2B-C5 | 1.00 | 0.10 | 0.12 | yes | yes |
| EX. 2B-5 | 1.00 | 0.50 | 0.12 | no | no |
| EX. 2B-6 | 1.00 | 2.00 | 0.12 | no | no |
| EX. 2B-C6 | 2.00 | 0.05 | 0.12 | yes | yes |
| EX. 2B-C7 | 2.00 | 0.10 | 0.12 | yes | yes |
| EX. 2B-7 | 2.00 | 0.50 | 0.12 | no | no |
| EX. 2B-8 | 2.00 | 2.00 | 0.12 | no | no |

TABLE 2C

EXAMPLE 2C

| EX. 2C | NaSaccharin Final wt % | CANARCEL Final wt % | CHG Final wt % | PPT Initial | PPT after 1 hr. |
|---|---|---|---|---|---|
| EX. 2C-C1 | 0.05 | 0.00 | 0.06 | no | no |
| EX. 2C-C2 | 0.10 | 0.00 | 0.06 | no | no |
| EX. 2C-C3 | 0.20 | 0.00 | 0.06 | no | no |
| EX. 2C-C4 | 0.50 | 0.00 | 0.06 | yes | yes |
| EX. 2C-C5 | 0.50 | 0.05 | 0.06 | yes | yes |
| EX. 2C-1 | 0.50 | 0.10 | 0.06 | no | yes |
| EX. 2C-2 | 0.50 | 2.00 | 0.06 | no | no |
| EX. 2C-C6 | 1.00 | 0.00 | 0.06 | no | yes |
| EX. 2C-3 | 1.00 | 0.05 | 0.06 | no | yes |
| EX. 2C-4 | 1.00 | 0.10 | 0.06 | no | yes |
| EX. 2C-5 | 1.00 | 2.00 | 0.06 | no | no |
| EX. 2C-C7 | 2.00 | 0.05 | 0.06 | yes | yes |
| EX. 2C-6 | 2.00 | 0.10 | 0.06 | no | yes |
| EX. 2C-7 | 2.00 | 2.00 | 0.06 | no | no |

Example 2D

The following samples of Example 2D were prepared in the concentrations described in Table 2D and tested as describe above in the ANTIMICROBIAL EFFICACY TEST. Comparative examples were designated: EX.2D-C1, EX.2D-C2, EX.2D-C3, etc.

TABLE 2D

EXAMPLE 2D

| EX. 2D | NaSaccharin Final wt % | CANARCEL Final wt % | CHG Final wt % | Log Reduction |
|---|---|---|---|---|
| EX. 2D-1 | 0.20 | 0.20 | 0.12 | 4.9 |
| EX. 2D-2 | 0.10 | 0.20 | 0.12 | 4.9 |
| EX. 2D-C1 | 0.20 | 0.00 | 0.12 | 1.2 |
| EX. 2D-C2 | 0.00 | 0.20 | 0.12 | 4.9 |
| EX. 2D-C3 | 0.10 | 0.00 | 0.12 | 4.9 |
| EX. 2D-C4 | 0.20 | 0.20 | 0.00 | 0.0 |
| EX. 2D-C5 | 0.00 | 0.00 | 0.12 | 4.9 |
| EX. 2D-C6 | 0.10 | 0.20 | 0.00 | −0.1 |

Example 3

The following samples of Example 3 were prepared and tested as described above in PRECIPITATION TEST and the ANTIMICROBIAL EFFICACY TEST to study the effect of AMMONYX and sodium saccharin on CHG precipitation and biological activity. The test organism used was Staphylococcus aureus (ATCC® 25923™) instead of methicillin-resistant Staphylococcus aureus, (ATCC® 33592™). Comparative examples were designated: EX.3-C1, EX.3-C2, EX.3-C3, etc.

TABLE 3

EXAMPLE 3

| EX.3 | NaSaccharin Final wt % | AMMONYX Final wt % | CHG Final wt % | PPT (1 min) | Log Reduction | Log Red. St. Dev. |
|---|---|---|---|---|---|---|
| EX.3-1 | 0.2 | 0.2* | 0.12 | no | 5.3 | 0.0 |
| EX.3-C1 | 0.0 | 0.2* | 0.0 | no | 1.6 | 0.2 |
| EX.3-C2 | 0.2 | 0.2* | 0.0 | no | 0.6 | 0.0 |
| EX.3-C3 | 0.0 | 0.2* | 0.12 | no | 5.3 | 0.0 |
| EX.3-C4 | 0.2 | 0.0 | 0.12 | yes | 0.6 | 0.1 |
| EX.3-C5 | 0.0 | 0.0 | 0.12 | no | 5.3 | 0.0 |
| EX.3-C6 PBW Control | 0.0 | 0.0 | 0.0 | no | n/a | n/a |

*(0.066 wt. % active in 0.2 wt. % AMMONYX))

Comparative Example 4

The following samples of Comparative Example 4 were prepared and tested as described above in the ANTIMICROBIAL EFFICACY TEST to study the effect of CANARCEL and TWEEN 20 on the antimicrobial activity of CHG, absent a precipitating anion. The test organism used was Staphylococcus aureus (ATCC® 25923™) instead of methicillin-resistant Staphylococcus aureus, (ATCC® 33592™), and the incubation time was 48 hours. These results show that at certain concentrations some surfactants can have a negative effect on the antimicrobial activity of CHG and that certain optimum concentrations of surfactants may exist. At a surfactant to CHG concentration below 2/0.12 or 17:1 for TWEEN 20 and below 1/0.12 or 8.3:1 for CANARCEL at least a 2 log reduction was achieved.

TABLE 4

COMPARATIVE EXAMPLE 4

| EX. 4 | NaSaccharin Final wt % | CANARCEL Final wt % | TWEEN 20 Final wt % | CHG Final wt % | Log Reduction |
|---|---|---|---|---|---|
| EX. 4-C1 | 0 | 0.0 | — | 0.12 | 4.7 |
| EX. 4-C2 | 0 | 0.5 | — | 0.12 | 2.0 |
| EX. 4-C3 | 0 | 1.0 | — | 0.12 | 0.8 |
| EX. 4-C4 | 0 | 2.0 | — | 0.12 | 0.4 |
| EX. 4-C5 | 0 | 3.0 | — | 0.12 | 0.3 |
| EX. 4-C7 | 0 | — | 1.0 | 0.12 | 4.2 |
| EX. 4-C8 | 0 | — | 2.0 | 0.12 | 0.6 |
| EX. 4-C9 | 0 | — | 3.0 | 0.12 | 0.4 |

Comparative Examples 5A and 5B

Similar to Comparative Example 4, the following samples of Comparative Examples 5A and 5B were prepared and tested on different days as described above in the ANTIMICROBIAL EFFICACY TEST to study the effect of various surfactants on the antimicrobial activity of CHG, absent a precipitating anion. The test organism used was Staphylococcus aureus (ATCC® 25923™) instead of methicillin-resistant Staphylococcus aureus, (ATCC® 33592™), and the incubation time was 48 hours. These results show that at certain concentrations some surfactants can have a negative effect on the antimicrobial activity of CHG and that certain optimum concentrations of surfactants may exist.

TABLE 5A

COMPARATIVE EXAMPLE 5A

| EX. 5A | NaSaccharin Final wt % | CHG Final wt % | Surfactant Final wt % | Log Reduction | Log Red. St. Dev. |
|---|---|---|---|---|---|
| EX. 5A-C1 | 0 | 0 | 0.5% MACKAM L (0.15% active) | 0.5 | 0.0 |
| EX. 5A-C2 | 0 | 0.12 | 0.5% MACKAM L (0.15% active) | 5.5 | 0.1 |
| EX. 5A-C3 | 0 | 0.12 | 0.35% MACKAM L (0.11% active) | 5.5 | 0.0 |
| EX. 5A-C4 | 0 | 0.12 | 0.2% MACKAM L (0.06% active) | 5.6 | 0.0 |
| EX. 5A-C5 | 0 | 0 | 0.5% TWEEN 20 | 0.0 | 0.0 |
| EX. 5A-C6 | 0 | 0.12 | 0.5% TWEEN 20 | 5.5 | 0.2 |
| EX. 5A-C7 | 0 | 0.12 | 0.35% TWEEN 20 | 5.5 | 0.0 |
| EX. 5A-C8 | 0 | 0.12 | 0.2% TWEEN 20 | 5.6 | 0.0 |
| EX. 5A-C9 | 0 | 0.12 | 0.5% CANARCEL | 1.5 | 0.0 |

TABLE 5A-continued

COMPARATIVE EXAMPLE 5A

| EX. 5A | NaSaccharin Final wt % | CHG Final wt % | Surfactant Final wt % | Log Reduction | Log Red. St. Dev. |
|---|---|---|---|---|---|
| EX. 5A-C10 | 0 | 0.12 | 0.35% CANARCEL | 1.8 | 0.0 |
| EX. 5A-C11 | 0 | 0.12 | 0.2% CANARCEL | 3.3 | 0.0 |
| EX. 5A-C12 Control | 0 | 0.12 | None | 5.4 | 0.1 |

At a surfactant to CHG concentration below 4.2:1 for TWEEN 20 and below 3:1 for CANARCEL, at least a 2 log reduction was achieved for these nonionic polyethoxylated surfactants. The MACKAM L zwitterionic betaine surfactant did not reduce CHG activity even up to a surfactant to CHG ratio of 4.2:1.

TABLE 5B

COMPARATIVE EXAMPLE 5B

| EX. 5B | NaSaccharin Final wt % | CHG Final wt % | Surfactant Final wt % | Log Reduction | Log Red. St. Dev. |
|---|---|---|---|---|---|
| EX. 5B-C13 | 0 | 0 | 0.5% AMMONYX LMDO (0.17% active) | 1.5 | 0.1 |
| EX. 5B-C14 | 0 | 0.12 | 0.5% AMMONYX LMDO (0.17% active) | 4.9 | 0.1 |
| EX. 5B-C15 | 0 | 0.12 | 0.35% AMMONYX LMDO (0.12% active) | 4.7 | 0.1 |
| EX. 5B-C16 | 0 | 0.12 | 0.2% AMMONYX LMDO (0.07% active) | 4.8 | 0.2 |
| EX. 5B-C17 | 0 | 0 | 0.5% TRITON X-100 | -0.1 | 0.1 |
| EX. 5B-C18 | 0 | 0.12 | 0.5% TRITON X-100 | 4.8 | 0.2 |
| EX. 5B-C19 | 0 | 0.12 | 0.35% TRITON X-100 | 4.8 | 0.1 |
| EX. 5B-C20 | 0 | 0.12 | 0.2% TRITON X-100 | 4.9 | 0.1 |
| EX. 5B-C21 | 0 | 0 | 0.5% LECITHIN | -0.1 | 0.0 |
| EX. 5B-C22 | 0 | 0.12 | 0.5% LECITHIN | -0.04 | 0.0 |
| EX. 5B-C23 | 0 | 0.12 | 0.35% LECITHIN | 2.3 | 0.1 |
| EX. 5B-C24 | 0 | 0.12 | 0.2% LECITHIN | 4.8 | 0.2 |
| EX. 5B-C25 Control | 0 | 0.12 | None | 4.8 | 0.1 |

At a surfactant to CHG concentration below 4.2:1 for TRITON X-100, at least a 2 log reduction was achieved for this nonionic polyethoxylated surfactants. The AMMONYX LMDO amine oxide surfactant did not reduce CHG activity even up to a surfactant to CHG ratio of 4.2:1. At a ratio of 4.2:1 surfactant to CHG, lecithin completely inactivated CHG, and at lower ratios some activity was retained.

Test Method C—Reversal of Precipitation Test Method

Example test solutions were observed for the formation of a precipitate when CHG was mixed with an anionic compound and then again after the addition of selected surfactants intended to "reverse" the formation of the precipitate.

STEP 1. An amount of 20 grams of 0.48% CHG was added to 20 grams of 0.8% sodium saccharin solution to form a 40 gram precipitate mixture with a 0.24% CHG concentration and a 0.4% sodium saccharin concentration. The formation of precipitate was observed and recorded as either "yes" or "no."

STEP 2. To a 10 gram aliquot of the precipitate mixture of STEP 1 was added 10 grams of a 4.0% surfactant solution to form a mixture with final concentrations of 0.12% CHG, 0.2% sodium saccharin, and 2.0% surfactant. The presence of precipitate was observed and recorded as either "yes" or "no."

A CONTROL sample was prepared by diluting 10 grams of a 0.48% CHG solution with 30 grams of water to form a 0.12% CHG solution.)

Example 6

The following samples of Example 6 were prepared and tested according to TEST METHOD C—REVERSAL OF PRECIPITATION TEST METHOD and the ANTIMICROBIAL EFFICACY TEST to study the effect of various surfactants on reversing the precipitation of CHG in the presence of an anionic compound. The test organism used was *Staphylococcus aureus* (ATCC® 25923™) instead of methicillin-resistant *Staphylococcus aureus*, (MRSA, ATCC® 33592™), and the incubation time was 48 hours. Comparative examples were designated: EX.6-C1, EX.6-C2, EX.6-C3, etc.

TABLE 6A

DILUTIONS OF EXAMPLE 6

| Initial Concentration | Intermediate concentration Before Surfactant added | Final Concentration After Surfactant added |
| --- | --- | --- |
| 0.48% CHG | 0.24% CHG | 0.12% CHG |
| 0.8% Sodium Saccharin | 0.4% Sodium Saccharin | 0.2% Sodium Saccharin |
| 2.0% NaH2PO4 | 1.0% NaH2PO4 | 0.5% NaH2PO4 |
| 2.0% Sodium Bicarbonate | 1.0% Sodium Bicarbonate | 0.5% Sodium Bicarbonate |
| 4.0% TWEEN 20, MACKAM L,CANARCEL TW 62) | N/A | 2.0% TWEEN 20, 2.0% CANARCEL TW 62, 2.0% MACKAM L (0.6% active) |

TABLE 6B

EXAMPLE 6 REVERSAL of PRECIPITATION

| EX. 6 | 1:1 Anion + CHG Initial Concentrations | PPT Initial Obs. After CHG added. | Surfactant Added | PPT Obs. After surfactant added. | Log Reduction |
| --- | --- | --- | --- | --- | --- |
| EX. 6-1 | 0.8% NaSaccharin + 0.48% CHG | yes | 2% TWEEN 20 | no | 2.0 |
| EX. 6-2 | 0.8% NaSaccharin + 0.48% CHG | yes | 2% MACKAM L | no | 0.4 |
| EX. 6-3 | 2.0% NaH2PO4 + 0.48% CHG | yes | 2% MACKAM L | no | 4.2 |
| EX. 6-4 | 2.0% NaH2PO4 + 0.48% CHG | yes | 2% CANARCEL | no | 0.8 |
| EX. 6-5 | 2.0% NaHCO3 + 0.48% CHG | yes | 2% MACKAM L | no | 4.5 |
| EX. 6-6 | 2.0% NaHCO3 + 0.48% CHG | yes | 2% CANARCEL | no | 4.2 |
| EX. 6-C1 | 0.8% NaSaccharin + 0.48% CHG | yes | Water | yes | 0.4 |
| EX. 6-C2 | 2.0% NaH2PO4 + 0.48% CHG | yes | Water | yes | 3.3 |
| EX. 6-C3 | 2.0% NaHCO3 + 0.48% CHG | yes | Water | yes | 4.5 |
| EX. 6-C4 CONTROL | 0.12% CHG | no | Water | no | 4.4 |

Example 7

The following samples of Example 7 were prepared and tested according to TEST METHOD C—REVERSAL OF PRECIPITATION TEST METHOD and the ANTIMICROBIAL EFFICACY TEST to study the effect of various surfactants on reversing the precipitation of CHG in the presence of an anionic compound. The test organism used was *Staphylococcus aureus* (ATCC® 25923™) instead of methicillin-resistant *Staphylococcus aureus*, (MRSA, ATCC® 33592™), and the incubation time was 48 hours. Comparative examples were designated: EX.7-C1, EX.7-C2, EX.7-C3, etc.

TABLE 7A

DILUTIONS OF EXAMPLE 7

| Initial Concentration | Intermediate concentration Before Surfactant added | Final Concentration After Surfactant added |
|---|---|---|
| 0.48% CHG 0.8% Sodium Saccharin 0.4% CANARCEL TW 62 Or 1.0% CANARCEL TW 62 | 0.24% CHG 0.4% Sodium Saccharin N/A | 0.12% CHG 0.2% Sodium Saccharin 0.2% CANARCEL TW 62 Or 0.5% CANARCEL TW 62 |

TABLE 7B

EXAMPLE 7 - REVERSAL of PRECIPITATION

| EX. 7 | 1:1 Anion + CHG Initial Concentrations | PPT Initial Obs. After CHG added. | Surfactant Added | PPT Obs. After surfactant added. | Log Reduction |
|---|---|---|---|---|---|
| EX. 7-1 | 0.8% NaSaccharin + 0.48% CHG | yes | 0.4% CANARCEL | yes (less PPT) | 1.5 |
| EX. 7-2 | 0.8% NaSaccharin + 0.48% CHG | yes | 1.0% CANARCEL | no | 0.7 |
| EX. 7-C1 | 0.8% NaSaccharin + 0.48% CHG | yes | Water | yes | 0.1 |
| EX. 7-C2 | 0.48% CHG | no | 0.4% CANARCEL | no | 3.2 |
| EX. 7-C3 | 0.48% CHG | no | 1.0% CANARCEL | no | 0.9 |
| EX. 7-C4 CONTROL | Final conc. 0.12% CHG | no | Water | no | 4.8 |

Example 8

The following samples of Example 8 were prepared and tested according to TEST METHOD A—PRECIPITATION TEST to study the effect of various surfactants on the precipitation of CHG in the presence of various polyanionic compounds (thickeners), such as CARBOPOL 954, NaCMC, LUBRAGEL NP, and hyaluronic acid. The results of Example 8 show that precipitation cannot always be prevented with the addition of a surfactant for all anionic compounds (particularly some anionic thickeners) that precipitate with CHG.

Comparative Example 8A

Mixtures were prepared according to TEST METHOD A with the following final concentrations. For all samples the final CHG concentration was 0.12 wt %. The CARBOPOL 954 concentration was at four levels: 0.05%, 0.1%, 0.25%, and 0.5%; and one of the following surfactants: MACKAM L, TWEEN 20 and CANARCEL were each added to provide one of the following final concentrations of surfactants for each sample. The final wt. % concentrations of TWEEN20, MACKAM L, and CANARCEL were 0%, 0.05%, 0.1% or 0.5%. The active wt. % concentrations when using MACKAM L were 0%, 0.015%, 0.03% or 0.15%, respectively. At all levels of CARBOPOL 954, and at all concentrations of all three surfactants (MACKAM L, TWEEN 20 and CANARCEL), precipitation was observed initially after the addition of CHG and after standing for 1 hour.

Comparative Example 8B

Comparative Example 8B was prepared and tested in the same way as Comparative Example 8A, except that hyaluronic acid was used instead of CARBOPOL 954 and only one level of hyaluronic acid concentration was assessed: 0.125% final concentration. At all concentrations of all three surfactants (MACKAM L, TWEEN 20 and CANARCEL) described above in Comparative Example 8A, in the presence of hyaluronic acid, precipitation was observed initially after the addition of CHG and after standing for 1 hour.

Comparative Example 8C

Comparative Example 8C was prepared and tested in the same way as Comparative Example 8A, except that LUBRAJEL NP was used instead of CARBOPOL 954. At all levels of LUBRAJEL (0%, 0.05%, 0.1% and 0.5%), and at all concentrations of all three surfactants (MACKAM L, TWEEN 20 and CANARCEL), precipitation was observed initially after the addition of CHG and after standing for 1 hour.

Example 8D and Comparative Example 8D-C

Example 8D and Comparative Example 8D-C were prepared and tested in the same way as Comparative Example 8A, except that sodium carboxymethyl cellulose (NaCMC) was used instead of CARBOPOL 954. Comparative examples were designated: EX.8D-C1, EX.8D-C2, EX.8D-C3, etc. There was no precipitation observed after the combination of NaCMC with each of the surfactants. The precipitation results are reported in Table 8. In many cases, using the higher level of surfactant, prevented precipitate formation with NaCMC and CHG. However, the other thickeners: CARBOPOL 954, LUBRAGEL NP, and hyaluronic acid (Comparative Examples 8A-8C) all formed precipitates despite the addition of the surfactants evaluated.

TABLE 8

EXAMPLE 8D

| EX. 8D | NaCMC Thickener Final wt % | Surfactant | Surfactant Final wt % | PPT after just NaCMC + Surfactant | PPT Initially after CHG added | PPT 1 hour after CHG added |
| --- | --- | --- | --- | --- | --- | --- |
| EX. 8D-C1 | 0.500 | MACKAM L | 0.00 | no | yes | yes |
| EX. 8D-C2 | 0.500 | MACKAM L | 0.05* | no | yes | yes |
| EX. 8D-C3 | 0.500 | MACKAM L | 0.10* | no | yes | yes |
| EX. 8D-1 | 0.500 | MACKAM L | 0.50* | no | no | no |
| EX. 8D-C4 | 0.250 | MACKAM L | 0.00 | no | yes | yes |
| EX. 8D-C5 | 0.250 | MACKAM L | 0.05* | no | yes | yes |
| EX. 8D-C6 | 0.250 | MACKAM L | 0.10* | no | yes | yes |
| EX. 8D-2 | 0.250 | MACKAM L | 0.50* | no | no | no |
| EX. 8D-C7 | 0.100 | MACKAM L | 0.00 | no | yes | yes |
| EX. 8D-C8 | 0.100 | MACKAM L | 0.05* | no | yes | yes |
| EX. 8D-C9 | 0.100 | MACKAM L | 0.10* | no | yes | yes |
| EX. 8D-C10 | 0.100 | MACKAM L | 0.50* | no | yes | yes |
| EX. 8D-C11 | 0.050 | MACKAM L | 0.00 | no | yes | yes |
| EX. 8D-C12 | 0.050 | MACKAM L | 0.05* | no | yes | yes |
| EX. 8D-C13 | 0.050 | MACKAM L | 0.10* | no | yes | yes |
| EX. 8D-C14 | 0.050 | MACKAM L | 0.50* | no | yes | yes |
| EX. 8D-C15 | 0.500 | TWEEN | 0.00 | no | yes | yes |
| EX. 8D-C16 | 0.500 | TWEEN | 0.05 | no | yes | yes |
| EX. 8D-C17 | 0.500 | TWEEN | 0.10 | no | yes | yes |
| EX. 8D-3 | 0.500 | TWEEN | 0.50 | no | no | no |
| EX. 8D-C18 | 0.250 | TWEEN | 0.00 | no | yes | yes |
| EX. 8D-C19 | 0.250 | TWEEN | 0.05 | no | yes | yes |
| EX. 8D-C20 | 0.250 | TWEEN | 0.10 | no | yes | yes |
| EX. 8D-4 | 0.250 | TWEEN | 0.50 | no | no | no |
| EX. 8D-C21 | 0.100 | TWEEN | 0.00 | no | yes | yes |
| EX. 8D-C22 | 0.100 | TWEEN | 0.05 | no | yes | yes |
| EX. 8D-C23 | 0.100 | TWEEN | 0.10 | no | yes | yes |
| EX. 8D-5 | 0.100 | TWEEN | 0.50 | no | no | no |
| EX. 8D-C24 | 0.050 | TWEEN | 0.00 | no | yes | yes |
| EX. 8D-C25 | 0.050 | TWEEN | 0.05 | no | yes | yes |
| EX. 8D-C26 | 0.050 | TWEEN | 0.10 | no | yes | yes |
| EX. 8D-6 | 0.050 | TWEEN | 0.50 | no | no | no |
| EX. 8D-C27 | 0.500 | CANARCEL | 0.00 | no | yes | yes |
| EX. 8D-C28 | 0.500 | CANARCEL | 0.05 | no | yes | yes |
| EX. 8D-C29 | 0.500 | CANARCEL | 0.10 | no | yes | yes |
| EX. 8D-7 | 0.500 | CANARCEL | 0.50 | no | no | no |
| EX. 8D-C30 | 0.250 | CANARCEL | 0.00 | no | yes | yes |
| EX. 8D-C31 | 0.250 | CANARCEL | 0.05 | no | yes | yes |
| EX. 8D-C32 | 0.250 | CANARCEL | 0.10 | no | yes | yes |
| EX. 8D-8 | 0.250 | CANARCEL | 0.50 | no | no | no |
| EX. 8D-C33 | 0.100 | CANARCEL | 0.00 | no | yes | yes |
| EX. 8D-C34 | 0.100 | CANARCEL | 0.05 | no | yes | yes |
| EX. 8D-C35 | 0.100 | CANARCEL | 0.10 | no | yes | yes |
| EX. 8D-9 | 0.100 | CANARCEL | 0.50 | no | no | no |
| EX. 8D-C36 | 0.050 | CANARCEL | 0.00 | no | yes | yes |
| EX. 8D-C37 | 0.050 | CANARCEL | 0.05 | no | yes | yes |
| EX. 8D-10 | 0.050 | CANARCEL | 0.10 | no | no | yes |
| EX. 8D-11 | 0.050 | CANARCEL | 0.50 | no | no | no |

*MACKAM L contains only 30 wt. % active

Comparative Example 9

PERIDEX Chlorhexidine Gluconate 0.12% Oral Rinse (available from 3M Company of St. Paul, Minn., USA) is an oral rinse product that contains CHG, sodium saccharin and the surfactant CANARCEL. However the level of saccharin is low enough that even without the surfactant there would be no precipitate formed, as shown by the following experiment. An amount of 0.22 grams of a prepared 0.01% aqueous solution of FD&C Blue 1 (available from Warner-Jenkinson Company INC, South Plainfield N.J., now a part of Sensient Technologies Corporation, Milwaukee, Wis.) was added to each of two 25 mL vials (Vial #1 and Vial #2). To both vials was added 0.40 grams of a 0.5% sodium saccharin solution. After each addition the vials were briefly swirled to aid mixing. To Vial #1, 0.34 grams of a 4% CANARCEL TW62 (surfactant) solution was added. No CANARCEL was added to Vial #2. To each vial 1.60 grams of glycerol (available from MP Biomedicals, Solon, Ohio) was added, followed by 2.00 grams of 200 proof ethanol (available from Columbus Chemical Industries, Columbus, Wis.). To Vial #1, 15.20 grams of purified water was added and the solution was shaken to mix well. To Vial #2, 15.54 grams of purified water was added and the solution was shaken to mix. To each vial 0.24 grams of a 10% CHG solution was added and the solutions were shaken vigorously to mix and left to stand. Example 9 Vial #1 was equivalent to that of PERIDEX oral rinse, except that it did not contain a flavoring that is present in PERIDEX at a final concentration of 0.036% of the solution. Example 9 Vial #2 was equivalent to that of Example 9 Vial #1, except that did NOT contain the surfactant CANARCEL. Both vials were checked for precipitate directly after the CHG had been added, 25 minutes later and four days later. Both solutions remained free of precipitate, which demonstrates that the surfactant in commercially available PERIDEX formulation is not preventing the precipitate of CHG and saccharin since there is no precipitate even when the surfactant is removed from the formulation.

Comparative Example 10

As described in Example 4 of published U.S. Patent Publication No. 2008/0108674 a cationic excipient (surfactant) can stabilize a mixture of an anionic dye and CHG.

Comparative Example 10A

In a 100 mL jar (Jar #1), 0.13 grams of FD&C Yellow dye No. 6 was mixed with 0.858 grams of 30 wt. % active MACKAM L and 6 mL of a 50% v/v of isopropyl alcohol (available from EMD Millipore, Billerica Mass.) in distilled water. In a separate 100 mL jar (Jar #2), 1.0 grams of PVP (average molecular weight 8,000, available from ISP Technologies, Wayne, N.J.) was dissolved in 30 grams of distilled water. After the PVP was completely dissolved, the contents of Jar #2 were added to Jar #1. Next, 5.662 grams of PEG (average molecular weight of 300, available from Sigma-Aldrich Company, Milwaukee Wis.) was added and the solution was mixed. To this 10.6 g of 20% w/v CHG solution was added. Finally, distilled water was added to bring the total weight of the solution to 100 grams. It was noticed when the CHG was added that the solution became very cloudy which did not clear up upon standing but sank to the bottom within 24 hours.

Comparative Example 10B

Comparative Example 10B was prepared in the same fashion as Comparative Example 10A except that 0.3 grams of the surfactant TWEEN 20 dissolved in 6 mL of distilled water was used to replace the MACKAM L dissolved in 6 mL of a 50% v/v of isopropyl alcohol and distilled water. Upon addition of the CHG, the solution became cloudy and the precipitate sank to the bottom of the jar within 24 hours.

Comparative Examples 10C-10E

Comparative Examples 10C-10E were prepared in the same fashion as Comparative Example 10A, with the exceptions described in Table 9, to compare the cationic and non-ionic (or zwitterionic) surfactants. In Comparative Example 10C, an amount of 0.3 grams of CPC was used as the surfactant. Comparative Example 10D, no surfactant was added. Comparative Example 10E, an amount of 0.3 grams of CPC was dissolved in 6 mL distilled water, instead of IPA/water.

TABLE 9

| COMPARATIVE EXAMPLE 10 | | | | | | | | |
|---|---|---|---|---|---|---|---|---|
| Comp. EX. 10 | Surfactant | Dye | Solvent | Excipients | CHG | PPT Initial | PPT @ 15 Min. | PPT @ 24 hrs. |
| EX. 10A | MACKAM L | Yellow #6 | IPA/H2O | PVP/PEG | 2.1% | yes | yes | yes |
| EX. 10B | TWEEN 20 | Yellow #6 | H2O | PVP/PEG | 2.1% | yes | yes | yes |
| EX. 10C | CPC | Yellow #6 | IPA/H2O | PVP/PEG | 2.1% | no | no | no |
| EX. 10D | None | Yellow #6 | IPA/H2O | PVP/PEG | 2.1% | yes | yes | yes |
| EX. 10E | CPC | Yellow #6 | H2O | PVP/PEG | 2.1% | no | no | no |

Examples A-Q

The following samples of Examples A-Q were prepared and tested as describe above in TEST METHOD A—PRECIPITATION TEST. The presence of a precipitate was evaluated for Short Term stability, at 15 minutes and for the Long Term stability, after at least 2 weeks. The sum total amount of multivalent cationic antiseptic (MCA)+solubilizing surfactant+anionic compound is reported in the columns labeled "(CHG or OCT or PHMB+Surf.+Anion) as % of Total." The remaining portion of each solution is water. The relative amount of the three components: MCA, surfactant and anion are also reported in weight percent relative to each other. The actual final concentration of MCA in the solution was always targeted to be 0.24%

The data collected for EXAMPLES A-P were plotted using TRI-PLOT (Graham and Midgley 2000; copyright 2003 David Graham and Nicholas Midgley). TRI-PLOT is a MICROSOFT EXCEL spreadsheet for the preparation of triangular (ternary) diagrams for tri-variate data. The conventional triangular diagrams were used to represent tri-variate data in which the three variables: (1) multivalent cationic antiseptic, (2) anionic compound, (3) a solubilizing surfactant; together represented proportions of a whole (100%)

TABLE A

EXAMPLE A - CHG/NaSaccharin/AMMONYX LMDO (amine oxide) - FIG. 3

| Point | (CHG + Surf. + Anion) as % of total | ST & LT Stability Points | Relative % CHG | Relative % NaSaccharin | Relative % Active Amine oxide Surfactant | PPT @ 15 min | PPT @ 2 weeks |
|---|---|---|---|---|---|---|---|
| A1 | 0.2 | — | 100.0 | 0.0 | 0.0 | no | n/a |
| A2 | 0.3 | — | 93.6 | 0.0 | 6.4 | no | n/a |
| A3 | 0.3 | — | 87.9 | 0.0 | 12.1 | no | n/a |
| A4 | 0.4 | — | 59.3 | 0.0 | 40.7 | no | n/a |
| A5 | 0.6 | — | 42.1 | 0.0 | 57.9 | no | n/a |
| A6 | 0.9 | — | 26.7 | 0.0 | 73.3 | no | n/a |
| A7 | 0.3 | — | 82.8 | 17.2 | 0.0 | no | n/a |
| A8 | 0.3 | — | 78.3 | 16.3 | 5.4 | no | n/a |
| A9 | 0.3 | — | 74.3 | 15.5 | 10.2 | no | n/a |
| A10 | 0.5 | — | 52.7 | 11.0 | 36.3 | no | n/a |
| A11 | 0.6 | — | 38.7 | 8.1 | 53.2 | no | n/a |
| A12 | 0.9 | — | 25.3 | 5.3 | 69.5 | no | n/a |
| A13 | 0.3 | — | 70.6 | 29.4 | 0.0 | yes | yes |
| A14 | 0.4 | — | 67.3 | 28.0 | 4.6 | no | yes |
| A15 | 0.4 | — | 64.3 | 26.8 | 8.8 | no | yes |
| A16 | 0.5 | — | 47.5 | 19.8 | 32.7 | no | yes |
| A17 | 0.7 | — | 35.8 | 14.9 | 49.3 | no | yes |
| A18 | 1.0 | — | 24.0 | 10.0 | 66.0 | no | yes |
| A19 | 0.4 | — | 54.6 | 45.5 | 0.0 | yes | yes |
| A20 | 0.5 | — | 52.6 | 43.8 | 3.6 | yes | yes |
| A21 | 0.5 | — | 50.7 | 42.3 | 7.0 | yes | yes |
| A22 | 0.6 | — | 39.7 | 33.1 | 27.3 | no | yes |
| A23 | 0.8 | G3 | 31.2 | 26.0 | 42.9 | no | no |
| A24 | 1.1 | — | 21.8 | 18.2 | 60.0 | no | no |
| A25 | 0.7 | — | 32.4 | 67.6 | 0.0 | yes | yes |
| A26 | 0.8 | — | 31.7 | 66.1 | 2.2 | yes | yes |
| A27 | 0.8 | — | 31.1 | 64.7 | 4.3 | yes | yes |
| A28 | 0.9 | — | 26.5 | 55.2 | 18.2 | no | yes |
| A29 | 1.1 | H3 | 22.5 | 46.7 | 30.8 | no | no |
| A30 | 1.4 | — | 17.1 | 35.7 | 47.1 | no | no |
| A31 | 1.2 | — | 19.4 | 80.7 | 0.0 | yes | yes |
| A32 | 1.3 | — | 19.1 | 79.6 | 1.3 | yes | yes |
| A33 | 1.3 | — | 18.9 | 78.6 | 2.6 | yes | yes |
| A34 | 1.4 | — | 17.1 | 71.2 | 11.7 | yes | yes |
| A35 | 1.6 | — | 15.3 | 63.7 | 21.0 | no | yes |
| A36 | 1.9 | J3 | 12.6 | 52.7 | 34.7 | no | no |
| A37 | 2.2 | — | 10.7 | 89.3 | 0.0 | yes | yes |
| A38 | 2.3 | — | 10.6 | 88.6 | 0.7 | yes | yes |
| A39 | 2.3 | — | 10.6 | 88.0 | 1.5 | yes | yes |
| A40 | 2.4 | — | 10.0 | 83.2 | 6.9 | yes | yes |
| A41 | 2.6 | — | 9.3 | 77.8 | 12.8 | yes | yes |
| A42 | 2.9 | I3 | 8.2 | 69.0 | 22.8 | no | no |
| A43 | 0.3 | — | 70.1 | 29.2 | 0.7 | no | yes |
| A44 | 0.5 | — | 49.6 | 49.7 | 0.7 | yes | yes |
| A45 | 0.5 | — | 50.3 | 48.3 | 1.4 | yes | yes |
| A46 | 0.5 | — | 51.0 | 46.9 | 2.1 | yes | yes |
| A47 | 0.5 | — | 51.8 | 45.5 | 2.8 | yes | yes |
| A48 | 0.7 | — | 32.1 | 65.1 | 2.8 | yes | yes |
| A49 | 0.7 | — | 32.6 | 63.9 | 3.5 | yes | yes |
| A50 | 1.3 | — | 19.1 | 77.8 | 3.1 | yes | yes |
| A51 | 1.2 | — | 19.3 | 77.0 | 3.7 | yes | yes |
| A52 | 1.2 | — | 19.5 | 76.3 | 4.3 | yes | yes |
| A53 | 1.2 | — | 19.7 | 75.5 | 4.9 | yes | yes |
| A54 | 1.2 | — | 19.9 | 74.6 | 5.5 | yes | yes |
| A55 | 1.2 | — | 20.1 | 73.8 | 6.1 | yes | yes |
| A56 | 1.2 | — | 20.4 | 72.9 | 6.7 | yes | yes |

TABLE A-continued

EXAMPLE A - CHG/NaSaccharin/AMMONYX LMDO (amine oxide) - FIG. 3

| Point | (CHG + Surf. + Anion) as % of total | ST & LT Stability Points | Relative % CHG | Relative % NaSaccharin | Relative % Active Amine oxide Surfactant | PPT @ 15 min | PPT @ 2 weeks |
|---|---|---|---|---|---|---|---|
| A57 | 1.2 | — | 20.6 | 72.1 | 7.4 | yes | yes |
| A58 | 1.2 | — | 20.8 | 71.2 | 8.0 | yes | yes |
| A59 | 1.1 | — | 21.1 | 70.2 | 8.7 | yes | yes |
| A60 | 1.1 | — | 21.3 | 69.3 | 9.4 | yes | yes |
| A61 | 0.6 | — | 42.9 | 42.9 | 14.2 | yes | yes |
| A62 | 0.4 | — | 56.0 | 20.6 | 23.3 | no | yes |
| A63 | 0.4 | — | 67.9 | 17.0 | 15.1 | no | yes |
| A64 | 0.7 | — | 36.0 | 54.1 | 9.9 | yes | yes |
| A65 | 2.5 | — | 9.6 | 75.9 | 14.5 | yes | yes |
| A66 | 2.4 | — | 9.9 | 73.9 | 16.3 | no | yes |
| A67 | 0.5 | — | 47.2 | 38.6 | 14.2 | yes | yes |
| A68 | 0.6 | — | 38.6 | 47.2 | 14.2 | yes | yes |
| A69 | 0.5 | — | 44.2 | 39.8 | 16.0 | yes | yes |
| A70 | 0.6 | — | 41.7 | 45.9 | 12.4 | yes | yes |
| A71 | 0.5 | — | 51.5 | 34.4 | 14.2 | yes | yes |
| A72 | 0.4 | D3 | 55.8 | 30.1 | 14.2 | no | yes |
| A73 | 0.7 | — | 34.3 | 51.5 | 14.2 | yes | yes |
| A74 | 0.8 | — | 30.1 | 55.8 | 14.2 | yes | yes |
| A75 | 0.9 | — | 25.8 | 60.1 | 14.2 | yes | yes |
| A76 | 1.1 | — | 21.5 | 64.4 | 14.2 | yes | yes |
| A77 | 0.5 | — | 45.5 | 36.4 | 18.0 | yes | yes |
| A78 | 0.5 | E3 | 47.0 | 32.9 | 20.1 | no | yes |
| A79 | 0.6 | — | 40.6 | 48.7 | 10.7 | yes | yes |
| A80 | 0.6 | — | 39.5 | 51.4 | 9.1 | yes | yes |
| A81 | 0.6 | — | 38.5 | 53.9 | 7.6 | yes | yes |
| A82 | 0.6 | — | 37.5 | 56.3 | 6.2 | yes | yes |
| A83 | 0.7 | — | 36.6 | 58.6 | 4.8 | yes | yes |
| A84 | 0.7 | — | 35.7 | 60.7 | 3.5 | yes | yes |
| A85 | 0.7 | — | 34.9 | 62.8 | 2.3 | yes | yes |
| A86 | 0.7 | — | 34.1 | 64.8 | 1.1 | yes | yes |
| A87 | 1.4 | — | 17.2 | 68.7 | 14.1 | yes | yes |
| A88 | 1.9 | — | 12.9 | 73.0 | 14.1 | yes | yes |
| A89 | 0.6 | — | 39.3 | 57.2 | 3.5 | yes | yes |
| A90 | 0.6 | — | 42.8 | 53.6 | 3.5 | yes | yes |
| A91 | 0.5 | — | 46.4 | 50.1 | 3.5 | yes | yes |
| A92 | 0.5 | — | 50.0 | 46.5 | 3.5 | yes | yes |
| A93 | 0.7 | — | 34.6 | 57.7 | 7.6 | yes | yes |
| A94 | 0.8 | — | 30.8 | 61.6 | 7.6 | yes | yes |
| A95 | 0.9 | — | 27.0 | 65.4 | 7.6 | yes | yes |
| A96 | 1.0 | — | 23.1 | 69.3 | 7.6 | yes | yes |
| A97 | 3.0 | F3 | 8.0 | 76.0 | 16.0 | no | yes |
| A98 | 0.4 | — | 56.5 | 42.8 | 0.7 | yes | yes |
| A99 | 0.4 | — | 58.6 | 40.7 | 0.7 | yes | yes |
| A100 | 0.4 | — | 60.5 | 38.8 | 0.7 | yes | yes |
| A101 | 0.4 | — | 62.3 | 37.1 | 0.7 | yes | yes |
| A102 | 0.4 | — | 63.9 | 35.5 | 0.7 | yes | yes |
| A103 | 0.4 | — | 65.3 | 34.0 | 0.7 | yes | yes |
| A104 | 0.4 | — | 66.7 | 32.7 | 0.7 | yes | yes |
| A105 | 0.4 | C3 | 67.9 | 31.4 | 0.7 | no | yes |
| A106 | 0.3 | — | 69.0 | 30.3 | 0.7 | no | yes |
| A107 | 5.5 | — | 4.4 | 72.9 | 22.8 | yes | yes |
| A108 | 5.4 | — | 4.5 | 80.2 | 15.4 | yes | yes |
| A109 | 5.4 | — | 4.4 | 76.7 | 18.9 | yes | yes |
| A110 | 3.6 | — | 6.7 | 47.0 | 46.4 | no | yes |
| A111 | — | A3 | 1.2 | 1.2 | 97.6 | — | — |
| A112 | — | B3 | 82.2 | 17.1 | 0.7 | — | — |

The lightly shaded (diagonal lines) area of FIG. 3 represents compositions that do not have precipitate in the Short Term, graphically depicted within the boundaries defined by vertices: A3, B3, C3, D3, E3, and F3. The darker shaded (crossing diagonal lines) area of FIG. 3 represents compositions that do not have precipitate in the Long Term, graphically depicted within the boundaries defined by vertices: A3, G3, H3, I3, and J3.

TABLE B

EXAMPLE B - CHG/NaSaccharin/BRIJ 78 (poly(oxyethylene)(C8-C22)alkyl ether) - FIG. 10

| Point | (CHG + Surf. + Anion) as % of total | Short Term Stability Points | Relative % CHG | Relative % NaSaccharin | Relative % BRIJ 78 | PPT @ 15 min |
|---|---|---|---|---|---|---|
| B1 | 0.2 | — | 100.0 | 0.0 | 0.0 | no |
| B2 | 0.3 | — | 82.8 | 0.0 | 17.2 | no |
| B3 | 0.3 | — | 70.6 | 0.0 | 29.4 | no |
| B4 | 0.7 | — | 32.4 | 0.0 | 67.6 | no |
| B5 | 1.2 | — | 19.4 | 0.0 | 80.7 | no |
| B6 | 2.2 | — | 10.7 | 0.0 | 89.3 | no |
| B7 | 0.3 | — | 82.8 | 17.2 | 0.0 | no |
| B8 | 0.3 | — | 70.6 | 14.7 | 14.7 | no |
| B9 | 0.4 | — | 61.5 | 12.8 | 25.6 | no |
| B10 | 0.8 | — | 30.4 | 6.3 | 63.3 | no |
| B11 | 1.3 | — | 18.6 | 3.9 | 77.5 | no |
| B12 | 2.3 | — | 10.5 | 2.2 | 87.3 | no |
| B13 | 0.3 | — | 70.6 | 29.4 | 0.0 | yes |
| B14 | 0.4 | — | 61.5 | 25.6 | 12.8 | no |
| B15 | 0.4 | — | 54.5 | 22.7 | 22.7 | no |
| B16 | 0.8 | — | 28.6 | 11.9 | 59.5 | no |
| B17 | 1.3 | — | 17.9 | 7.5 | 74.6 | no |
| B18 | 2.3 | — | 10.3 | 4.3 | 85.5 | no |
| B19 | 0.4 | — | 54.6 | 45.5 | 0.0 | yes |
| B20 | 0.5 | — | 49.0 | 40.8 | 10.2 | yes |
| B21 | 0.5 | — | 44.4 | 37.0 | 18.5 | yes |
| B22 | 0.9 | — | 25.5 | 21.3 | 53.2 | no |
| B23 | 1.4 | — | 16.7 | 13.9 | 69.4 | no |
| B24 | 2.4 | — | 9.8 | 8.2 | 82.0 | no |
| B25 | 0.7 | — | 32.4 | 67.6 | 0.0 | yes |
| B26 | 0.8 | — | 30.4 | 63.3 | 6.3 | yes |
| B27 | 0.8 | — | 28.6 | 59.5 | 11.9 | yes |
| B28 | 1.2 | — | 19.4 | 40.3 | 40.3 | no |
| B29 | 1.7 | — | 13.8 | 28.7 | 57.5 | no |
| B30 | 2.7 | — | 8.8 | 18.3 | 73.0 | no |
| B31 | 1.2 | — | 19.4 | 80.7 | 0.0 | yes |
| B32 | 1.3 | — | 18.6 | 77.5 | 3.9 | yes |
| B33 | 1.3 | — | 17.9 | 74.6 | 7.5 | yes |
| B34 | 1.7 | — | 13.8 | 57.5 | 28.7 | no |
| B35 | 2.2 | — | 10.7 | 44.6 | 44.6 | no |
| B36 | 3.2 | — | 7.4 | 30.9 | 61.7 | no |
| B37 | 2.2 | — | 10.7 | 89.3 | 0.0 | yes |
| B38 | 2.3 | — | 10.5 | 87.3 | 2.2 | yes |
| B39 | 2.3 | — | 10.3 | 85.5 | 4.3 | yes |
| B40 | 2.7 | — | 8.8 | 73.0 | 18.3 | yes |
| B41 | 3.2 | — | 7.4 | 61.7 | 30.9 | no |
| B42 | 4.2 | — | 5.7 | 47.2 | 47.2 | no |
| B43 | 0.3 | — | 69.2 | 28.8 | 2.0 | yes |
| B44 | 0.4 | — | 67.8 | 28.2 | 4.0 | yes |
| B45 | 0.4 | — | 66.4 | 27.7 | 6.0 | no |
| B46 | 0.7 | — | 33.3 | 33.3 | 33.3 | yes |
| B47 | 0.4 | — | 53.5 | 40.5 | 6.0 | yes |
| B48 | 0.4 | — | 55.5 | 38.5 | 6.0 | yes |
| B49 | 0.4 | — | 57.3 | 36.7 | 6.0 | yes |
| B50 | 0.4 | — | 58.9 | 35.1 | 6.0 | yes |
| B51 | 0.4 | — | 60.4 | 33.6 | 6.0 | yes |
| B52 | 0.4 | — | 61.8 | 32.2 | 6.0 | yes |
| B53 | 0.4 | — | 63.1 | 30.9 | 6.0 | yes |
| B54 | 0.4 | — | 64.3 | 29.8 | 6.0 | yes |
| B55 | 0.4 | C10 | 65.3 | 28.7 | 6.0 | no |
| B56 | 0.5 | — | 44.4 | 35.2 | 20.4 | yes |
| B57 | 0.5 | — | 44.4 | 33.3 | 22.2 | yes |
| B58 | 0.5 | — | 44.4 | 31.5 | 24.1 | yes |
| B59 | 0.5 | — | 44.4 | 29.6 | 25.9 | yes |
| B60 | 0.5 | — | 44.4 | 27.8 | 27.8 | no |
| B61 | 0.6 | — | 38.0 | 14.0 | 48.0 | no |
| B62 | 0.5 | — | 52.0 | 13.0 | 35.0 | no |
| B63 | 1.5 | — | 16.0 | 39.0 | 45.0 | no |
| B64 | 0.6 | — | 40.0 | 15.0 | 45.0 | no |
| B65 | 2.7 | — | 8.8 | 71.2 | 20.1 | yes |
| B66 | 2.7 | — | 8.8 | 69.3 | 21.9 | yes |

TABLE B-continued

EXAMPLE B - CHG/NaSaccharin/BRIJ 78 (poly(oxyethylene)(C8-C22)alkyl ether) - FIG. 10

| Point | (CHG + Surf. + Anion) as % of total | Short Term Stability Points | Relative % CHG | Relative % NaSaccharin | Relative % BRIJ 78 | PPT @ 15 min |
|---|---|---|---|---|---|---|
| B67 | 2.7 | — | 8.8 | 67.5 | 23.7 | yes |
| B68 | 2.7 | — | 8.8 | 65.7 | 25.6 | yes |
| B69 | 2.7 | — | 8.8 | 63.9 | 27.4 | yes |
| B70 | 2.7 | — | 8.8 | 62.0 | 29.2 | no |
| B71 | 1.2 | — | 19.4 | 26.7 | 53.9 | no |
| B72 | 1.3 | — | 17.9 | 50.9 | 31.2 | no |
| B73 | 1.2 | F10 | 19.4 | 51.9 | 28.7 | no |
| B74 | 6.6 | — | 3.7 | 67.6 | 28.7 | yes |
| B75 | 8.0 | — | 3.0 | 49.8 | 47.2 | no |
| B76 | 15.0 | — | 1.6 | 11.1 | 87.3 | no |
| B77 | 0.8 | — | 30.0 | 33.3 | 36.7 | yes |
| B78 | 0.9 | — | 26.7 | 33.3 | 40.0 | yes |
| B79 | 1.0 | — | 23.3 | 33.3 | 43.3 | yes |
| B80 | 1.2 | E10 | 20.0 | 33.3 | 46.7 | no |
| B81 | 4.8 | — | 5.0 | 66.3 | 28.7 | yes |
| B82 | 4.0 | — | 6.0 | 65.3 | 28.7 | yes |
| B83 | 3.4 | — | 7.0 | 64.3 | 28.7 | yes |
| B84 | 3.0 | G10 | 8.0 | 63.3 | 28.7 | no |
| B85 | 1.2 | D10 | 20.0 | 26.1 | 53.9 | no |
| B86 | 1.2 | — | 20.0 | 51.3 | 28.7 | yes |
| B87 | — | A10 | 1.2 | 1.2 | 97.6 | — |
| B88 | — | B10 | 77.8 | 16.2 | 6.0 | — |
| B89 | — | H10 | 1.2 | 45.0 | 53.8 | — |

The lightly shaded area of FIG. 10 represents compositions that do not have precipitate in the Short Term, graphically depicted within the boundaries defined by vertices: A10, B10, C10, D10, E10, F10, G10, and H10.

TABLE C

EXAMPLE C - CHG/NaSaccharin/CANARCEL (poly(oxyethylene)sorbitan fatty acid diester) - FIG. 8

| Point | (CHG + Surf. + Anion) as % of total | Short Term Stability Points | Relative % CHG | Relative % NaSaccharin | Relative % CANARCEL | PPT @ 15 min |
|---|---|---|---|---|---|---|
| C1 | 0.2 | — | 100.0 | 0.0 | 0.0 | no |
| C2 | 0.3 | — | 82.8 | 0.0 | 17.2 | no |
| C3 | 0.3 | — | 70.6 | 0.0 | 29.4 | no |
| C4 | 0.7 | — | 32.4 | 0.0 | 67.6 | no |
| C5 | 1.2 | — | 19.4 | 0.0 | 80.7 | no |
| C6 | 2.2 | — | 10.7 | 0.0 | 89.3 | no |
| C7 | 0.3 | — | 82.8 | 17.2 | 0.0 | no |
| C8 | 0.3 | — | 70.6 | 14.7 | 14.7 | no |
| C9 | 0.4 | — | 61.5 | 12.8 | 25.6 | no |
| C10 | 0.8 | — | 30.4 | 6.3 | 63.3 | no |
| C11 | 1.3 | — | 18.6 | 3.9 | 77.5 | no |
| C12 | 2.3 | — | 10.5 | 2.2 | 87.3 | no |
| C13 | 0.3 | — | 70.6 | 29.4 | 0.0 | yes |
| C14 | 0.4 | — | 61.5 | 25.6 | 12.8 | no |
| C15 | 0.4 | — | 54.5 | 22.7 | 22.7 | no |
| C16 | 0.8 | — | 28.6 | 11.9 | 59.5 | no |
| C17 | 1.3 | — | 17.9 | 7.5 | 74.6 | no |
| C18 | 2.3 | — | 10.3 | 4.3 | 85.5 | no |
| C19 | 0.4 | — | 54.6 | 45.5 | 0.0 | yes |
| C20 | 0.5 | — | 49.0 | 40.8 | 10.2 | yes |
| C21 | 0.5 | — | 44.4 | 37.0 | 18.5 | yes |
| C22 | 0.9 | — | 25.5 | 21.3 | 53.2 | no |
| C23 | 1.4 | — | 16.7 | 13.9 | 69.4 | no |
| C24 | 2.4 | — | 9.8 | 8.2 | 82.0 | no |
| C25 | 0.7 | — | 32.4 | 67.6 | 0.0 | yes |
| C26 | 0.8 | — | 30.4 | 63.3 | 6.3 | yes |
| C27 | 0.8 | — | 28.6 | 59.5 | 11.9 | yes |
| C28 | 1.2 | — | 19.4 | 40.3 | 40.3 | yes |
| C29 | 1.7 | — | 13.8 | 28.7 | 57.5 | no |
| C30 | 2.7 | — | 8.8 | 18.3 | 73.0 | no |

TABLE C-continued

EXAMPLE C - CHG/NaSaccharin/CANARCEL (poly(oxyethylene)sorbitan fatty acid diester) - FIG. 8

| Point | (CHG + Surf. + Anion) as % of total | Short Term Stability Points | Relative % CHG | Relative % NaSaccharin | Relative % CANARCEL | PPT @ 15 min |
|---|---|---|---|---|---|---|
| C31 | 1.2 | — | 19.4 | 80.7 | 0.0 | yes |
| C32 | 1.3 | — | 18.6 | 77.5 | 3.9 | yes |
| C33 | 1.3 | — | 17.9 | 74.6 | 7.5 | yes |
| C34 | 1.7 | — | 13.8 | 57.5 | 28.7 | yes |
| C35 | 2.2 | E8 | 10.7 | 44.6 | 44.6 | no |
| C36 | 3.2 | — | 7.4 | 30.9 | 61.7 | no |
| C37 | 2.2 | — | 10.7 | 89.3 | 0.0 | yes |
| C38 | 2.3 | — | 10.5 | 87.3 | 2.2 | yes |
| C39 | 2.3 | — | 10.3 | 85.5 | 4.3 | yes |
| C40 | 2.7 | — | 8.8 | 73.0 | 18.3 | yes |
| C41 | 3.2 | H8 | 7.4 | 61.7 | 30.9 | no |
| C42 | 4.2 | I8 | 5.7 | 47.2 | 47.2 | no |
| C43 | 0.3 | — | 69.2 | 28.8 | 2.0 | yes |
| C44 | 0.4 | — | 67.8 | 28.2 | 4.0 | no |
| C45 | 0.7 | — | 33.3 | 33.3 | 33.3 | yes |
| C46 | 0.4 | — | 54.6 | 41.4 | 4.0 | yes |
| C47 | 0.4 | — | 56.7 | 39.3 | 4.0 | yes |
| C48 | 0.4 | — | 58.5 | 37.5 | 4.0 | yes |
| C49 | 0.4 | — | 60.2 | 35.8 | 4.0 | yes |
| C50 | 0.4 | — | 61.7 | 34.3 | 4.0 | yes |
| C51 | 0.4 | — | 63.1 | 32.9 | 4.0 | yes |
| C52 | 0.4 | — | 64.4 | 31.6 | 4.0 | yes |
| C53 | 0.4 | C8 | 65.6 | 30.4 | 4.0 | no |
| C54 | 1.2 | — | 19.4 | 39.5 | 41.1 | yes |
| C55 | 1.2 | — | 19.4 | 38.7 | 41.9 | yes |
| C56 | 1.2 | — | 19.4 | 37.9 | 42.7 | yes |
| C57 | 1.2 | — | 19.4 | 37.1 | 43.6 | yes |
| C58 | 1.9 | — | 12.4 | 57.5 | 30.1 | yes |
| C59 | 2.2 | — | 11.0 | 57.5 | 31.5 | yes |
| C60 | 2.5 | — | 9.7 | 57.5 | 32.9 | yes |
| C61 | 2.9 | F8 | 8.3 | 57.5 | 34.3 | no |
| C62 | 2.7 | — | 8.8 | 71.2 | 20.1 | yes |
| C63 | 2.7 | — | 8.8 | 69.3 | 21.9 | yes |
| C64 | 2.7 | — | 8.8 | 67.5 | 23.7 | yes |
| C65 | 2.7 | G8 | 8.8 | 65.7 | 25.6 | no |
| C66 | 0.6 | — | 38.0 | 14.0 | 48.0 | no |
| C67 | 0.5 | — | 52.0 | 13.0 | 35.0 | no |
| C68 | 0.6 | D8 | 38.5 | 16.9 | 44.6 | no |
| C69 | 8.0 | — | 3.0 | 49.8 | 47.2 | yes |
| C70 | 15.0 | — | 1.6 | 11.1 | 87.3 | yes |
| C71 | 6.4 | — | 3.8 | 70.7 | 25.6 | no |
| C72 | 5.9 | — | 4.1 | 34.2 | 61.7 | yes |
| C73 | 7.5 | — | 3.2 | 23.8 | 73.0 | yes |
| C74 | 9.4 | J8 | 2.6 | 15.5 | 82.0 | no |
| C75 | — | A8 | 1.2 | 1.2 | 97.6 | — |
| C76 | — | B8 | 79.4 | 16.6 | 4.0 | — |
| C77 | — | K8 | 1.2 | 9.2 | 89.6 | — |

The lightly shaded area of FIG. 8 represents compositions that do not have precipitate in the Short Term, graphically depicted within the boundaries defined by vertices: A8, B8, C8, D8, E8, F8, G8, H8, I8, J8, and K8.

TABLE D

EXAMPLE D - CHG/NaSaccharin/Decaglyn 1M (polyglycerol (C8-C22)fatty acid ester) - FIG. 9

| Point | (CHG + Surf. + Anion) as % of total | Short Term Stability Points | Relative % CHG | Relative % NaSaccharin | Relative % Decaglyn 1M | PPT @ 15 min |
|---|---|---|---|---|---|---|
| D1 | 0.2 | — | 100.0 | 0.0 | 0.0 | no |
| D2 | 0.3 | — | 82.8 | 0.0 | 17.2 | no |
| D3 | 0.3 | — | 70.6 | 0.0 | 29.4 | no |
| D4 | 0.7 | — | 32.4 | 0.0 | 67.6 | no |
| D5 | 1.2 | — | 19.4 | 0.0 | 80.7 | no |
| D6 | 2.2 | — | 10.7 | 0.0 | 89.3 | no |

TABLE D-continued

EXAMPLE D - CHG/NaSaccharin/Decaglyn 1M (polyglycerol (C8-C22)fatty acid ester) - FIG. 9

| Point | (CHG + Surf. + Anion) as % of total | Short Term Stability Points | Relative % CHG | Relative % NaSaccharin | Relative % Decaglyn 1M | PPT @ 15 min |
|---|---|---|---|---|---|---|
| D7 | 0.3 | — | 82.8 | 17.2 | 0.0 | no |
| D8 | 0.3 | — | 70.6 | 14.7 | 14.7 | no |
| D9 | 0.4 | — | 61.5 | 12.8 | 25.6 | no |
| D10 | 0.8 | — | 30.4 | 6.3 | 63.3 | no |
| D11 | 1.3 | — | 18.6 | 3.9 | 77.5 | no |
| D12 | 2.3 | — | 10.5 | 2.2 | 87.3 | no |
| D13 | 0.3 | — | 70.6 | 29.4 | 0.0 | yes |
| D14 | 0.4 | — | 61.5 | 25.6 | 12.8 | no |
| D15 | 0.4 | — | 54.5 | 22.7 | 22.7 | no |
| D16 | 0.8 | — | 28.6 | 11.9 | 59.5 | no |
| D17 | 1.3 | — | 17.9 | 7.5 | 74.6 | no |
| D18 | 2.3 | — | 10.3 | 4.3 | 85.5 | no |
| D19 | 0.4 | — | 54.6 | 45.5 | 0.0 | yes |
| D20 | 0.5 | — | 49.0 | 40.8 | 10.2 | yes |
| D21 | 0.5 | — | 44.4 | 37.0 | 18.5 | yes |
| D22 | 0.9 | D9 | 25.5 | 21.3 | 53.2 | no |
| D23 | 1.4 | — | 16.7 | 13.9 | 69.4 | no |
| D24 | 2.4 | — | 9.8 | 8.2 | 82.0 | no |
| D25 | 0.7 | — | 32.4 | 67.6 | 0.0 | yes |
| D26 | 0.8 | — | 30.4 | 63.3 | 6.3 | yes |
| D27 | 0.8 | — | 28.6 | 59.5 | 11.9 | yes |
| D28 | 1.2 | F9 | 19.4 | 40.3 | 40.3 | no |
| D29 | 1.7 | — | 13.8 | 28.7 | 57.5 | no |
| D30 | 2.7 | — | 8.8 | 18.3 | 73.0 | no |
| D31 | 1.2 | — | 19.4 | 80.7 | 0.0 | yes |
| D32 | 1.3 | — | 18.6 | 77.5 | 3.9 | yes |
| D33 | 1.3 | — | 17.9 | 74.6 | 7.5 | yes |
| D34 | 1.7 | — | 13.8 | 57.5 | 28.7 | yes |
| D35 | 2.2 | — | 10.7 | 44.6 | 44.6 | no |
| D36 | 3.2 | — | 7.4 | 30.9 | 61.7 | no |
| D37 | 2.2 | — | 10.7 | 89.3 | 0.0 | yes |
| D38 | 2.3 | — | 10.5 | 87.3 | 2.2 | yes |
| D39 | 2.3 | — | 10.3 | 85.5 | 4.3 | yes |
| D40 | 2.7 | — | 8.8 | 73.0 | 18.3 | yes |
| D41 | 3.2 | — | 7.4 | 61.7 | 30.9 | yes |
| D42 | 4.2 | H9 | 5.7 | 47.2 | 47.2 | no |
| D43 | 0.3 | — | 69.2 | 28.8 | 2.0 | yes |
| D44 | 0.4 | — | 67.8 | 28.2 | 4.0 | no |
| D45 | 0.7 | — | 33.3 | 33.3 | 33.3 | yes |
| D46 | 0.4 | — | 54.6 | 41.4 | 4.0 | yes |
| D47 | 0.4 | — | 56.7 | 39.3 | 4.0 | yes |
| D48 | 0.4 | — | 58.5 | 37.5 | 4.0 | yes |
| D49 | 0.4 | — | 60.2 | 35.8 | 4.0 | yes |
| D50 | 0.4 | — | 61.7 | 34.3 | 4.0 | yes |
| D51 | 0.4 | — | 63.1 | 32.9 | 4.0 | yes |
| D52 | 0.4 | — | 64.4 | 31.6 | 4.0 | yes |
| D53 | 0.4 | — | 65.6 | 30.4 | 4.0 | yes |
| D54 | 0.4 | C9 | 66.7 | 29.3 | 4.0 | no |
| D55 | 3.2 | — | 7.4 | 58.6 | 34.0 | yes |
| D56 | 3.2 | — | 7.4 | 55.6 | 37.0 | yes |
| D57 | 3.2 | G9 | 7.4 | 52.5 | 40.1 | no |
| D58 | 0.6 | — | 38.0 | 14.0 | 48.0 | no |
| D59 | 0.5 | — | 52.0 | 13.0 | 35.0 | no |
| D60 | 1.0 | — | 25.0 | 30.0 | 45.0 | yes |
| D61 | 1.2 | — | 19.4 | 29.4 | 51.3 | yes |
| D62 | 1.2 | — | 19.4 | 28.2 | 52.5 | no |
| D63 | 1.2 | — | 19.4 | 30.7 | 50.0 | yes |
| D64 | 1.3 | E9 | 18.5 | 29.0 | 52.5 | no |
| D65 | 7.4 | — | 3.3 | 56.4 | 40.3 | yes |
| D66 | 8.0 | — | 3.0 | 49.8 | 47.2 | yes |
| D67 | 15.0 | — | 1.6 | 11.1 | 87.3 | yes |
| D68 | — | A9 | 1.2 | 1.2 | 97.6 | — |
| D69 | — | B9 | 79.4 | 16.6 | 4.0 | — |

The lightly shaded area of FIG. 9 represents compositions that do not have precipitate in the Short Term, graphically depicted within the boundaries defined by vertices: A9, B9, C9, D9, E9, F9, G9, and H9.

TABLE E

EXAMPLE E - CHG/NaSaccharin/GLUCOPON 225DK ((C8-C22)alkyl polyglycoside) - FIG. 11

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| E1  | 0.2 | —   | 100.0 | 0.0  | 0.0  | no  | n/a |
| E2  | 0.3 | —   | 87.3  | 0.0  | 12.7 | no  | n/a |
| E3  | 0.3 | —   | 77.4  | 0.0  | 22.6 | no  | n/a |
| E4  | 0.6 | —   | 40.7  | 0.0  | 59.3 | no  | n/a |
| E5  | 0.9 | —   | 25.5  | 0.0  | 74.5 | no  | n/a |
| E6  | 1.6 | —   | 14.6  | 0.0  | 85.4 | no  | n/a |
| E7  | 0.3 | —   | 82.8  | 17.2 | 0.0  | no  | n/a |
| E8  | 0.3 | —   | 73.8  | 15.4 | 10.8 | no  | n/a |
| E9  | 0.4 | —   | 66.7  | 13.9 | 19.4 | no  | n/a |
| E10 | 0.6 | —   | 37.5  | 7.8  | 54.7 | no  | n/a |
| E11 | 1.0 | —   | 24.2  | 5.1  | 70.7 | no  | n/a |
| E12 | 1.7 | —   | 14.2  | 3.0  | 82.8 | no  | n/a |
| E13 | 0.3 | —   | 70.6  | 29.4 | 0.0  | yes | yes |
| E14 | 0.4 | —   | 64.0  | 26.7 | 9.3  | no  | yes |
| E15 | 0.4 | —   | 58.5  | 24.4 | 17.1 | no  | yes |
| E16 | 0.7 | —   | 34.8  | 14.5 | 50.7 | no  | yes |
| E17 | 1.0 | —   | 23.1  | 9.6  | 67.3 | no  | yes |
| E18 | 1.7 | —   | 13.8  | 5.7  | 80.5 | no  | yes |
| E19 | 0.4 | —   | 54.6  | 45.5 | 0.0  | yes | yes |
| E20 | 0.5 | —   | 50.5  | 42.1 | 7.4  | yes | yes |
| E21 | 0.5 | —   | 47.1  | 39.2 | 13.7 | yes | yes |
| E22 | 0.8 | —   | 30.4  | 25.3 | 44.3 | yes | yes |
| E23 | 1.1 | —   | 21.1  | 17.5 | 61.4 | no  | yes |
| E24 | 1.8 | M11 | 13.0  | 10.9 | 76.1 | no  | no  |
| E25 | 0.7 | —   | 32.4  | 67.6 | 0.0  | yes | yes |
| E26 | 0.8 | —   | 31.0  | 64.5 | 4.5  | yes | yes |
| E27 | 0.8 | —   | 29.6  | 61.7 | 8.6  | yes | yes |
| E28 | 1.1 | —   | 22.0  | 45.9 | 32.1 | yes | yes |
| E29 | 1.4 | G11 | 16.7  | 34.7 | 48.6 | no  | yes |
| E30 | 2.1 | —   | 11.2  | 23.4 | 65.4 | no  | yes |
| E31 | 1.2 | —   | 19.4  | 80.7 | 0.0  | yes | yes |
| E32 | 1.3 | —   | 18.8  | 78.4 | 2.7  | yes | yes |
| E33 | 1.3 | —   | 18.3  | 76.3 | 5.3  | yes | yes |
| E34 | 1.6 | —   | 15.1  | 62.9 | 22.0 | yes | yes |
| E35 | 1.9 | —   | 12.4  | 51.5 | 36.1 | yes | yes |
| E36 | 2.6 | —   | 9.1   | 37.9 | 53.0 | no  | yes |
| E37 | 2.2 | —   | 10.7  | 89.3 | 0.0  | yes | yes |
| E38 | 2.3 | —   | 10.5  | 87.9 | 1.5  | yes | yes |
| E39 | 2.3 | —   | 10.4  | 86.6 | 3.0  | yes | yes |
| E40 | 2.6 | —   | 9.3   | 77.2 | 13.5 | yes | yes |
| E41 | 2.9 | —   | 8.2   | 68.0 | 23.8 | yes | yes |
| E42 | 3.6 | —   | 6.6   | 54.9 | 38.5 | yes | yes |
| E43 | 0.3 | —   | 69.6  | 29.0 | 1.4  | no  | yes |
| E44 | 0.4 | —   | 56.1  | 42.5 | 1.4  | yes | yes |
| E45 | 0.4 | —   | 58.2  | 40.4 | 1.4  | yes | yes |
| E46 | 0.4 | —   | 60.1  | 38.5 | 1.4  | yes | yes |
| E47 | 0.4 | —   | 61.8  | 36.8 | 1.4  | yes | yes |
| E48 | 0.4 | —   | 63.4  | 35.2 | 1.4  | yes | yes |
| E49 | 0.4 | —   | 64.8  | 33.8 | 1.4  | yes | yes |
| E50 | 0.4 | —   | 66.2  | 32.4 | 1.4  | yes | yes |
| E51 | 0.4 | —   | 67.4  | 31.2 | 1.4  | yes | yes |
| E52 | 0.4 | C11 | 68.5  | 30.1 | 1.4  | no  | yes |
| E53 | 3.6 | J11 | 6.7   | 50.3 | 43.0 | no  | yes |
| E54 | 0.8 | —   | 30.7  | 22.4 | 47.0 | yes | yes |
| E55 | 0.8 | D11 | 31.0  | 19.4 | 49.6 | no  | yes |
| E56 | 0.6 | —   | 37.0  | 37.0 | 25.9 | yes | yes |
| E57 | 0.5 | —   | 44.4  | 16.4 | 39.3 | no  | yes |
| E58 | 0.4 | —   | 58.1  | 14.5 | 27.4 | no  | yes |
| E59 | 0.9 | —   | 27.5  | 26.4 | 46.1 | yes | yes |
| E60 | 1.0 | —   | 24.6  | 27.4 | 48.0 | yes | yes |
| E61 | 1.1 | —   | 21.7  | 28.5 | 49.8 | yes | yes |
| E62 | 1.3 | —   | 18.7  | 29.6 | 51.7 | yes | yes |
| E63 | 1.5 | —   | 16.3  | 40.6 | 43.0 | yes | yes |
| E64 | 1.3 | —   | 18.9  | 26.2 | 54.9 | yes | yes |
| E65 | 1.3 | F11 | 19.1  | 22.7 | 58.2 | no  | yes |
| E66 | 1.6 | —   | 14.7  | 42.3 | 43.0 | yes | yes |
| E67 | 1.8 | —   | 13.1  | 43.9 | 43.0 | yes | yes |

TABLE E-continued

EXAMPLE E - CHG/NaSaccharin/GLUCOPON 225DK
((C8-C22)alkyl polyglycoside) - FIG. 11

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| E68 | 2.1 | — | 11.4 | 45.5 | 43.0 | yes | yes |
| E69 | 2.4 | — | 9.8 | 47.2 | 43.0 | yes | yes |
| E70 | 2.9 | I11 | 8.2 | 48.8 | 43.0 | no | yes |
| E71 | 1.0 | — | 24.4 | 17.5 | 58.2 | yes | yes |
| E72 | 1.0 | — | 23.1 | 17.1 | 59.8 | no | yes |
| E73 | 2.9 | H11 | 8.3 | 43.1 | 48.6 | no | yes |
| E74 | 0.9 | E11 | 25.8 | 13.3 | 60.9 | no | yes |
| E75 | 10.1 | K11 | 2.4 | 21.5 | 76.1 | no | no |
| E76 | 7.1 | — | 3.4 | 53.6 | 43.0 | yes | yes |
| E77 | 8.2 | — | 2.9 | 38.4 | 58.6 | yes | yes |
| E78 | — | A11 | 1.2 | 1.2 | 97.6 | — | — |
| E79 | — | B11 | 81.6 | 17.0 | 1.4 | — | — |
| E80 | — | L11 | 13.0 | 2.7 | 84.3 | — | — |

The lightly shaded area of FIG. 11 represents compositions that do not have precipitate in the Short Term, graphically depicted within the boundaries defined by vertices: A11, B11, C11, D11, E11, F11, G11, H11, I11, J11, and K11. The darker shaded area of FIG. 11 represents compositions that do not have precipitate in the Long Term, graphically depicted within the boundaries defined by vertices: A11, L11, M11, and K11.

TABLE F

EXAMPLE F - CHG/NaSaccharin/MACKAM 50-SB ((C8-C22)alkylamido(C2-C4)alkylhydroxy sultaine) - FIG. 5

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| F1 | 0.2 | — | 100.0 | 0.0 | 0.0 | no | n/a |
| F2 | 0.3 | — | 91.8 | 0.0 | 8.2 | no | n/a |
| F3 | 0.3 | — | 84.8 | 0.0 | 15.2 | no | n/a |
| F4 | 0.5 | — | 52.7 | 0.0 | 47.3 | no | n/a |
| F5 | 0.7 | — | 35.8 | 0.0 | 64.2 | no | n/a |
| F6 | 1.1 | — | 21.8 | 0.0 | 78.2 | no | n/a |
| F7 | 0.3 | — | 82.8 | 17.2 | 0.0 | no | n/a |
| F8 | 0.3 | — | 77.1 | 16.0 | 6.9 | no | n/a |
| F9 | 0.3 | — | 72.1 | 15.0 | 12.9 | no | n/a |
| F10 | 0.5 | — | 47.5 | 9.9 | 42.6 | no | n/a |
| F11 | 0.7 | — | 33.3 | 7.0 | 59.7 | no | n/a |
| F12 | 1.1 | — | 20.9 | 4.3 | 74.8 | no | n/a |
| F13 | 0.3 | — | 70.6 | 29.4 | 0.0 | yes | yes |
| F14 | 0.4 | — | 66.4 | 27.7 | 5.9 | no | yes |
| F15 | 0.4 | — | 62.7 | 26.1 | 11.2 | no | yes |
| F16 | 0.6 | — | 43.2 | 18.0 | 38.7 | no | yes |
| F17 | 0.8 | D5 | 31.2 | 13.0 | 55.8 | no | yes |
| F18 | 1.2 | — | 20.0 | 8.3 | 71.7 | no | yes |
| F19 | 0.4 | — | 54.6 | 45.5 | 0.0 | yes | yes |
| F20 | 0.5 | — | 52.0 | 43.3 | 4.7 | yes | yes |
| F21 | 0.5 | — | 49.7 | 41.4 | 8.9 | yes | yes |
| F22 | 0.7 | — | 36.6 | 30.5 | 32.8 | yes | yes |
| F23 | 0.9 | — | 27.6 | 23.0 | 49.4 | yes | yes |
| F24 | 1.3 | G5 | 18.5 | 15.4 | 66.1 | no | no |
| F25 | 0.7 | — | 32.4 | 67.6 | 0.0 | yes | yes |
| F26 | 0.8 | — | 31.5 | 65.7 | 2.8 | yes | yes |
| F27 | 0.8 | — | 30.7 | 63.9 | 5.5 | yes | yes |
| F28 | 1.0 | — | 25.1 | 52.4 | 22.5 | yes | yes |
| F29 | 1.2 | — | 20.5 | 42.7 | 36.8 | yes | yes |
| F30 | 1.6 | E5 | 15.0 | 31.3 | 53.7 | no | no |
| F31 | 1.2 | — | 19.4 | 80.6 | 0.0 | yes | yes |
| F32 | 1.3 | — | 19.0 | 79.3 | 1.7 | yes | yes |
| F33 | 1.3 | — | 18.7 | 77.9 | 3.4 | yes | yes |
| F34 | 1.5 | — | 16.5 | 68.7 | 14.8 | yes | yes |
| F35 | 1.7 | — | 14.4 | 59.9 | 25.7 | yes | yes |
| F36 | 2.1 | H5 | 11.4 | 47.6 | 41.0 | no | no |
| F37 | 2.2 | — | 10.7 | 89.3 | 0.0 | yes | yes |

TABLE F-continued

EXAMPLE F - CHG/NaSaccharin/MACKAM 50-SB ((C8-C22)alkylamido(C2-C4)alkylhydroxy sultaine) - FIG. 5

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| F38 | 2.3 | — | 10.6 | 88.4 | 0.9 | yes | yes |
| F39 | 2.3 | — | 10.5 | 87.6 | 1.9 | yes | yes |
| F40 | 2.5 | — | 9.8 | 81.5 | 8.8 | yes | yes |
| F41 | 2.7 | F5 | 9.0 | 74.9 | 16.1 | no | yes |
| F42 | 3.1 | — | 7.7 | 64.5 | 27.7 | no | yes |
| F43 | 0.3 | C5 | 70.0 | 29.1 | 0.9 | no | yes |
| F44 | 0.6 | — | 41.2 | 41.2 | 17.7 | yes | yes |
| F45 | 0.4 | — | 56.4 | 42.7 | 0.9 | yes | yes |
| F46 | 0.4 | — | 58.5 | 40.6 | 0.9 | yes | yes |
| F47 | 0.4 | — | 60.4 | 38.7 | 0.9 | yes | yes |
| F48 | 0.4 | — | 62.1 | 37.0 | 0.9 | yes | yes |
| F49 | 0.4 | — | 63.7 | 35.4 | 0.9 | yes | yes |
| F50 | 0.4 | — | 65.2 | 33.9 | 0.9 | yes | yes |
| F51 | 0.4 | — | 66.5 | 32.6 | 0.9 | yes | yes |
| F52 | 0.4 | — | 67.8 | 31.4 | 0.9 | yes | yes |
| F53 | 0.3 | — | 68.9 | 30.2 | 0.9 | yes | yes |
| F54 | 0.9 | — | 28.0 | 21.0 | 51.1 | yes | yes |
| F55 | 0.8 | — | 28.3 | 18.9 | 52.8 | yes | yes |
| F56 | 0.5 | — | 52.3 | 19.3 | 28.4 | no | yes |
| F57 | 0.4 | — | 65.0 | 16.2 | 18.8 | no | yes |
| F58 | 1.8 | — | 13.0 | 60.9 | 26.2 | yes | yes |
| F59 | 2.1 | — | 11.6 | 61.8 | 26.6 | yes | yes |
| F60 | 2.4 | — | 10.2 | 62.8 | 27.0 | no | yes |
| F61 | 2.7 | — | 8.8 | 63.8 | 27.4 | no | yes |
| F62 | 2.4 | — | 9.9 | 80.4 | 9.8 | yes | yes |
| F63 | 2.4 | — | 10.0 | 79.2 | 10.8 | yes | yes |
| F64 | 2.4 | — | 10.1 | 78.1 | 11.8 | yes | yes |
| F65 | 2.3 | — | 10.3 | 76.9 | 12.9 | yes | yes |
| F66 | 2.3 | — | 10.4 | 75.7 | 14.0 | yes | yes |
| F67 | 2.3 | — | 10.5 | 74.4 | 15.1 | yes | yes |
| F68 | 6.2 | — | 3.9 | 55.2 | 41.0 | yes | yes |
| F69 | 5.5 | — | 4.4 | 79.5 | 16.1 | yes | yes |
| F70 | 5.8 | — | 4.1 | 68.8 | 27.0 | yes | yes |
| F71 | 4.1 | — | 5.8 | 41.2 | 53.0 | no | yes |
| F72 | — | A5 | 1.2 | 1.2 | 97.6 | — | — |
| F73 | — | B5 | 82.0 | 17.1 | 0.9 | — | — |

The lightly shaded area of FIG. 5 represents compositions that do not have precipitate in the Short Term, graphically depicted within the boundaries defined by vertices: A5, B5, C5, D5, E5, and F5. The darker shaded area of FIG. 5 represents compositions that do not have precipitate in the Long Term, graphically depicted within the boundaries defined by vertices: A5, G5, and H5.

TABLE G

EXAMPLE G - CHG/NaSaccharin/MACKAM L ((C8-C22)alkylamido(C2-C4)alkyl betaine) - FIG. 4

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| G1 | 0.2 | — | 100.0 | 0.0 | 0.0 | no | n/a |
| G2 | 0.3 | — | 94.1 | 0.0 | 5.9 | no | n/a |
| G3 | 0.3 | — | 88.9 | 0.0 | 11.1 | no | n/a |
| G4 | 0.4 | — | 61.5 | 0.0 | 38.5 | no | n/a |
| G5 | 0.5 | — | 44.5 | 0.0 | 55.5 | no | n/a |
| G6 | 0.8 | — | 28.5 | 0.0 | 71.5 | no | n/a |
| G7 | 0.3 | — | 82.8 | 17.2 | 0.0 | no | n/a |
| G8 | 0.3 | — | 78.7 | 16.4 | 4.9 | no | n/a |
| G9 | 0.3 | — | 75.0 | 15.6 | 9.4 | no | n/a |
| G10 | 0.4 | — | 54.6 | 11.3 | 34.1 | no | n/a |
| G11 | 0.6 | — | 40.7 | 8.5 | 50.8 | no | n/a |
| G12 | 0.9 | — | 27.0 | 5.7 | 67.3 | no | n/a |
| G13 | 0.3 | — | 70.6 | 29.4 | 0.0 | yes | yes |
| G14 | 0.4 | — | 67.6 | 28.2 | 4.2 | no | yes |
| G15 | 0.4 | — | 64.9 | 27.0 | 8.1 | no | yes |

TABLE G-continued

EXAMPLE G - CHG/NaSaccharin/MACKAM L ((C8-C22)alkylamido(C2-C4)alkyl betaine) - FIG. 4

| Point | (CHG + Surf. + Anion) as % of total | ST & LT Stability Points | Relative % CHG | Relative % NaSaccharin | Relative % Active Surfactant | PPT @ 15 min | PPT @ 2 weeks |
|---|---|---|---|---|---|---|---|
| G16 | 0.5 | — | 49.0 | 20.4 | 30.6 | no | yes |
| G17 | 0.6 | — | 37.5 | 15.7 | 46.8 | no | yes |
| G18 | 0.9 | — | 25.6 | 10.7 | 63.7 | no | yes |
| G19 | 0.4 | — | 54.5 | 45.5 | 0.0 | yes | yes |
| G20 | 0.5 | — | 52.8 | 43.9 | 3.3 | yes | yes |
| G21 | 0.5 | — | 51.1 | 42.6 | 6.4 | yes | yes |
| G22 | 0.6 | — | 40.6 | 33.9 | 25.4 | no | yes |
| G23 | 0.7 | I4 | 32.5 | 27.0 | 40.5 | no | no |
| G24 | 1.0 | — | 23.0 | 19.2 | 57.7 | no | no |
| G25 | 0.7 | — | 32.4 | 67.6 | 0.0 | yes | yes |
| G26 | 0.8 | — | 31.8 | 66.2 | 2.0 | yes | yes |
| G27 | 0.8 | — | 31.2 | 64.9 | 3.9 | yes | yes |
| G28 | 0.9 | E4 | 27.0 | 56.2 | 16.8 | no | yes |
| G29 | 1.0 | J4 | 23.1 | 48.0 | 28.9 | no | no |
| G30 | 1.3 | — | 18.0 | 37.3 | 44.7 | no | no |
| G31 | 1.2 | — | 19.4 | 80.6 | 0.0 | yes | yes |
| G32 | 1.3 | — | 19.1 | 79.7 | 1.2 | yes | yes |
| G33 | 1.3 | — | 18.9 | 78.7 | 2.4 | yes | yes |
| G34 | 1.4 | F4 | 17.2 | 72.0 | 10.8 | no | yes |
| G35 | 1.5 | — | 15.6 | 64.9 | 19.5 | no | yes |
| G36 | 1.8 | — | 13.0 | 54.4 | 32.6 | no | no |
| G37 | 2.2 | — | 10.7 | 89.3 | 0.0 | yes | yes |
| G38 | 2.3 | — | 10.7 | 88.7 | 0.7 | yes | yes |
| G39 | 2.3 | — | 10.6 | 88.1 | 1.3 | yes | yes |
| G40 | 2.4 | — | 10.1 | 83.6 | 6.3 | yes | yes |
| G41 | 2.5 | — | 9.4 | 78.7 | 11.8 | yes | yes |
| G42 | 2.8 | K4 | 8.5 | 70.4 | 21.1 | no | no |
| G43 | 0.3 | — | 70.2 | 29.2 | 0.6 | yes | yes |
| G44 | 0.3 | — | 69.8 | 29.0 | 1.2 | yes | yes |
| G45 | 0.3 | C4 | 69.2 | 28.9 | 1.9 | no | yes |
| G46 | 0.6 | — | 43.5 | 43.5 | 13.0 | yes | yes |
| G47 | 0.4 | — | 55.8 | 42.3 | 1.9 | yes | yes |
| G48 | 0.4 | — | 57.9 | 40.2 | 1.9 | yes | yes |
| G49 | 0.4 | — | 59.8 | 38.3 | 1.9 | yes | yes |
| G50 | 0.4 | — | 61.5 | 36.6 | 1.9 | yes | yes |
| G51 | 0.4 | — | 63.0 | 35.1 | 1.9 | yes | yes |
| G52 | 0.4 | — | 64.5 | 33.6 | 1.9 | yes | yes |
| G53 | 0.4 | — | 65.9 | 32.3 | 1.9 | yes | yes |
| G54 | 0.4 | — | 67.0 | 31.1 | 1.9 | yes | yes |
| G55 | 0.4 | — | 68.2 | 30.0 | 1.9 | yes | yes |
| G56 | 0.5 | — | 51.8 | 41.1 | 7.1 | yes | yes |
| G57 | 0.5 | — | 52.6 | 39.5 | 7.9 | yes | yes |
| G58 | 0.4 | — | 53.4 | 37.9 | 8.7 | yes | yes |
| G59 | 0.4 | — | 54.3 | 36.2 | 9.5 | yes | yes |
| G60 | 0.4 | — | 55.1 | 34.5 | 10.4 | yes | yes |
| G61 | 0.4 | — | 56.1 | 32.7 | 11.2 | yes | yes |
| G62 | 0.4 | — | 57.0 | 30.9 | 12.1 | no | yes |
| G63 | 2.5 | — | 9.7 | 76.9 | 13.4 | yes | yes |
| G64 | 2.4 | — | 10.0 | 75.0 | 15.0 | yes | yes |
| G65 | 2.3 | G4 | 10.3 | 73.0 | 16.7 | no | yes |
| G66 | 0.4 | — | 57.2 | 21.1 | 21.7 | no | yes |
| G67 | 0.3 | — | 68.9 | 17.2 | 13.9 | no | yes |
| G68 | 1.0 | — | 23.4 | 56.9 | 19.7 | no | yes |
| G69 | 0.5 | D4 | 51.3 | 31.8 | 16.9 | no | yes |
| G70 | 1.0 | — | 23.3 | 69.8 | 7.0 | yes | yes |
| G71 | 0.8 | — | 31.6 | 57.0 | 11.4 | yes | yes |
| G72 | 5.3 | — | 4.6 | 68.5 | 26.9 | no | yes |
| G73 | 5.3 | — | 4.5 | 71.5 | 23.9 | yes | yes |
| G74 | 5.4 | — | 4.5 | 70.1 | 25.4 | no | yes |
| G75 | — | A4 | 1.2 | 1.2 | 97.6 | — | — |
| G76 | — | B4 | 81.2 | 16.9 | 1.9 | — | — |
| G77 | — | H4 | 1.2 | 68.3 | 30.5 | — | — |

The lightly shaded area of FIG. 4 represents compositions that do not have precipitate in the Short Term, graphically depicted within the boundaries defined by vertices: A4, B4, C4, D4, E4, F4, G4, and H4. The darker shaded area of FIG. 4 represents compositions that do not have precipitate in the Long Term, graphically depicted within the boundaries defined by vertices: A4, I4, J4, and K4.

TABLE H

EXAMPLE H - CHG/NaSaccharin/TWEEN 20 (poly(oxyethylene)sorbitan fatty acid ester) - FIG. 7

| Point | (CHG + Surf. + Anion) as % of total | Short Term Stability Points | Relative % CHG | Relative % NaSaccharin | Relative % TWEEN 20 | PPT @ 15 min |
|---|---|---|---|---|---|---|
| H1 | 0.2 | — | 100.0 | 0.0 | 0.0 | no |
| H2 | 0.3 | — | 82.8 | 0.0 | 17.2 | no |
| H3 | 0.3 | — | 70.6 | 0.0 | 29.4 | no |
| H4 | 0.7 | — | 32.4 | 0.0 | 67.6 | no |
| H5 | 1.2 | — | 19.4 | 0.0 | 80.7 | no |
| H6 | 2.2 | — | 10.7 | 0.0 | 89.3 | no |
| H7 | 0.3 | — | 82.8 | 17.2 | 0.0 | no |
| H8 | 0.3 | — | 70.6 | 14.7 | 14.7 | no |
| H9 | 0.4 | — | 61.5 | 12.8 | 25.6 | no |
| H10 | 0.8 | — | 30.4 | 6.3 | 63.3 | no |
| H11 | 1.3 | — | 18.6 | 3.9 | 77.5 | no |
| H12 | 2.3 | — | 10.5 | 2.2 | 87.3 | no |
| H13 | 0.3 | — | 70.6 | 29.4 | 0.0 | yes |
| H14 | 0.4 | — | 61.5 | 25.6 | 12.8 | yes |
| H15 | 0.4 | — | 54.5 | 22.7 | 22.7 | yes |
| H16 | 0.8 | D7 | 28.6 | 11.9 | 59.5 | no |
| H17 | 1.3 | — | 17.9 | 7.5 | 74.6 | no |
| H18 | 2.3 | — | 10.3 | 4.3 | 85.5 | no |
| H19 | 0.4 | — | 54.6 | 45.5 | 0.0 | yes |
| H20 | 0.5 | — | 49.0 | 40.8 | 10.2 | yes |
| H21 | 0.5 | — | 44.4 | 37.0 | 18.5 | yes |
| H22 | 0.9 | — | 25.5 | 21.3 | 53.2 | yes |
| H23 | 1.4 | — | 16.7 | 13.9 | 69.4 | no |
| H24 | 2.4 | — | 9.8 | 8.2 | 82.0 | no |
| H25 | 0.7 | — | 32.4 | 67.6 | 0.0 | yes |
| H26 | 0.8 | — | 30.4 | 63.3 | 6.3 | yes |
| H27 | 0.8 | — | 28.6 | 59.5 | 11.9 | yes |
| H28 | 1.2 | — | 19.4 | 40.3 | 40.3 | yes |
| H29 | 1.7 | — | 13.8 | 28.7 | 57.5 | yes |
| H30 | 2.7 | — | 8.8 | 18.3 | 73.0 | no |
| H31 | 1.2 | — | 19.4 | 80.7 | 0.0 | yes |
| H32 | 1.3 | — | 18.6 | 77.5 | 3.9 | yes |
| H33 | 1.3 | — | 17.9 | 74.6 | 7.5 | yes |
| H34 | 1.7 | — | 13.8 | 57.5 | 28.7 | yes |
| H35 | 2.2 | — | 10.7 | 44.6 | 44.6 | no |
| H36 | 3.2 | — | 7.4 | 30.9 | 61.7 | no |
| H37 | 2.2 | — | 10.7 | 89.3 | 0.0 | yes |
| H38 | 2.3 | — | 10.5 | 87.3 | 2.2 | yes |
| H39 | 2.3 | — | 10.3 | 85.5 | 4.3 | yes |
| H40 | 2.7 | — | 8.8 | 73.0 | 18.3 | yes |
| H41 | 3.2 | H7 | 7.4 | 61.7 | 30.9 | no |
| H42 | 4.2 | — | 5.7 | 47.2 | 47.2 | no |
| H43 | 0.7 | — | 33.3 | 33.3 | 33.3 | no |
| H44 | 1.9 | — | 12.4 | 57.5 | 30.1 | yes |
| H45 | 2.2 | — | 11.0 | 57.5 | 31.5 | yes |
| H46 | 2.5 | — | 9.7 | 57.5 | 32.9 | yes |
| H47 | 2.9 | — | 8.3 | 57.5 | 34.3 | yes |
| H48 | 2.7 | — | 8.8 | 71.2 | 20.1 | yes |
| H49 | 2.7 | — | 8.8 | 69.3 | 21.9 | yes |
| H50 | 2.7 | — | 8.8 | 67.5 | 23.7 | yes |
| H51 | 2.7 | — | 8.8 | 65.7 | 25.6 | yes |
| H52 | 2.7 | — | 8.8 | 63.9 | 27.4 | yes |
| H53 | 2.7 | — | 8.8 | 62.0 | 29.2 | yes |
| H54 | 2.4 | F7 | 10.0 | 50.0 | 40.0 | no |
| H55 | 0.6 | — | 38.0 | 14.0 | 48.0 | no |
| H56 | 0.5 | — | 52.0 | 13.0 | 35.0 | no |
| H57 | 0.5 | C7 | 47.5 | 17.5 | 35.0 | no |
| H58 | 3.2 | G7 | 7.4 | 52.6 | 40.0 | no |
| H59 | 6.7 | — | 3.6 | 65.5 | 30.9 | yes |
| H60 | 8.0 | — | 3.0 | 49.8 | 47.2 | yes |
| H61 | 15.0 | — | 1.6 | 11.1 | 87.3 | no |
| H62 | 5.9 | — | 4.1 | 34.2 | 61.7 | yes |
| H63 | 7.5 | — | 3.2 | 23.8 | 73.0 | yes |

TABLE H-continued

EXAMPLE H - CHG/NaSaccharin/TWEEN 20 (poly(oxyethylene)sorbitan fatty acid ester) - FIG. 7

| Point | (CHG + Surf. + Anion) as % of total | Short Term Stability Points | Relative % CHG | Relative % NaSaccharin | Relative % TWEEN 20 | PPT @ 15 min |
|---|---|---|---|---|---|---|
| H64 | 9.4 | I7 | 2.6 | 15.5 | 82.0 | no |
| H65 | 2.2 | E7 | 10.7 | 29.8 | 59.5 | no |
| H66 | — | A7 | 1.2 | 1.2 | 97.6 | — |
| H67 | — | B7 | 53.8 | 11.2 | 35.0 | — |
| H68 | — | J7 | 1.2 | 9.2 | 89.6 | — |

The lightly shaded area of FIG. 7 represents compositions that do not have precipitate in the Short Term, graphically depicted within the boundaries defined by vertices: A7, B7, C7, D7, E7, F7, G7, H7, I7, and J7.

TABLE I

EXAMPLE I - CHG/Carboxymethycellulose ether sodium salt (CMC)/TWEEN 20 (poly(oxyethylene)sorbitan fatty acid ester) -FIG. 17

| Point | (CHG + Surf. + Anion) as % of total | ST & LT Stability Points | Relative % CHG | Relative % CMC | Relative % TWEEN 20 | PPT @ 15 min | PPT @ 2 weeks |
|---|---|---|---|---|---|---|---|
| I1 | 0.2 | — | 100.0 | 0.0 | 0.0 | no | n/a |
| I2 | 0.3 | — | 82.8 | 0.0 | 17.2 | no | n/a |
| I3 | 0.3 | — | 70.6 | 0.0 | 29.4 | no | n/a |
| I4 | 0.7 | — | 32.4 | 0.0 | 67.6 | no | n/a |
| I5 | 1.2 | — | 19.4 | 0.0 | 80.7 | no | n/a |
| I6 | 2.2 | — | 10.7 | 0.0 | 89.3 | no | n/a |
| I7 | 0.3 | — | 82.8 | 17.2 | 0.0 | yes | yes |
| I8 | 0.3 | — | 70.6 | 14.7 | 14.7 | yes | yes |
| I9 | 0.4 | — | 61.5 | 12.8 | 25.6 | yes | yes |
| I10 | 0.8 | — | 30.4 | 6.3 | 63.3 | yes | yes |
| I11 | 1.3 | — | 18.6 | 3.9 | 77.5 | yes | yes |
| I12 | 2.3 | — | 10.5 | 2.2 | 87.3 | yes | yes |
| I13 | 0.3 | — | 70.6 | 29.4 | 0.0 | yes | yes |
| I14 | 0.4 | — | 61.5 | 25.6 | 12.8 | yes | yes |
| I15 | 0.4 | — | 54.5 | 22.7 | 22.7 | yes | yes |
| I16 | 0.8 | — | 28.6 | 11.9 | 59.5 | yes | yes |
| I17 | 1.3 | — | 17.9 | 7.5 | 74.6 | yes | yes |
| I18 | 2.3 | — | 10.3 | 4.3 | 85.5 | yes | yes |
| I19 | 0.4 | — | 54.6 | 45.5 | 0.0 | yes | yes |
| I20 | 0.5 | — | 49.0 | 40.8 | 10.2 | yes | yes |
| I21 | 0.5 | — | 44.4 | 37.0 | 18.5 | yes | yes |
| I22 | 0.9 | — | 25.5 | 21.3 | 53.2 | yes | yes |
| I23 | 1.4 | — | 16.7 | 13.9 | 69.4 | yes | yes |
| I24 | 2.4 | E17 | 9.8 | 8.2 | 82.0 | no | no |
| I25 | 0.7 | — | 32.4 | 67.6 | 0.0 | yes | yes |
| I26 | 0.8 | — | 30.4 | 63.3 | 6.3 | yes | yes |
| I27 | 0.8 | — | 28.6 | 59.5 | 11.9 | yes | yes |
| I28 | 1.2 | — | 19.4 | 40.3 | 40.3 | yes | yes |
| I29 | 1.7 | — | 13.8 | 28.7 | 57.5 | yes | yes |
| I30 | 2.7 | — | 8.8 | 18.3 | 73.0 | yes | yes |
| I31 | 1.2 | — | 19.4 | 80.7 | 0.0 | yes | yes |
| I32 | 1.3 | — | 18.6 | 77.5 | 3.9 | yes | yes |
| I33 | 1.3 | — | 17.9 | 74.6 | 7.5 | yes | yes |
| I34 | 1.7 | — | 13.8 | 57.5 | 28.7 | yes | yes |
| I35 | 2.2 | — | 10.7 | 44.6 | 44.6 | yes | yes |
| I36 | 3.2 | — | 7.4 | 30.9 | 61.7 | yes | yes |
| I37 | 2.2 | — | 10.7 | 89.3 | 0.0 | yes | yes |
| I38 | 2.3 | — | 10.5 | 87.3 | 2.2 | yes | yes |
| I39 | 2.3 | — | 10.3 | 85.5 | 4.3 | yes | yes |
| I40 | 2.7 | — | 8.8 | 73.0 | 18.3 | yes | yes |
| I41 | 3.2 | — | 7.4 | 61.7 | 30.9 | yes | yes |
| I42 | 4.2 | — | 5.7 | 47.2 | 47.2 | yes | yes |
| I43 | 2.7 | — | 8.8 | 14.6 | 76.6 | yes | yes |
| I44 | 2.7 | — | 8.8 | 11.0 | 80.3 | no | yes |
| I45 | 2.4 | — | 9.8 | 6.2 | 84.0 | no | yes |
| I46 | 2.4 | — | 9.8 | 4.2 | 86.0 | no | yes |
| I47 | 8.5 | — | 2.8 | 16.9 | 80.3 | no | yes |
| I48 | 2.4 | C17 | 9.8 | 9.9 | 80.3 | no | yes |
| I49 | 2.4 | — | 9.8 | 7.2 | 83.0 | no | yes |

TABLE I-continued

EXAMPLE I - CHG/Carboxymethycellulose ether sodium salt (CMC)/TWEEN 20 (poly(oxyethylene)sorbitan fatty acid ester) -FIG. 17

| Point | (CHG + Surf. + Anion) as % of total | ST & LT Stability Points | Relative % CHG | Relative % CMC | Relative % TWEEN 20 | PPT @ 15 min | PPT @ 2 weeks |
|---|---|---|---|---|---|---|---|
| I50 | 3.0 | F17 | 8.0 | 10.0 | 82.0 | no | no |
| I51 | — | A17 | 1.2 | 1.2 | 97.6 | — | — |
| I52 | — | B17 | 9.8 | 1.2 | 89.0 | — | — |
| I53 | — | D17 | 1.2 | 18.5 | 80.3 | — | — |

The lightly shaded area of FIG. 17 represents compositions that do not have precipitate in the Short Term, graphically depicted within the boundaries defined by vertices: A17, B17, C17, and D17. The darker shaded area of FIG. 17 represents compositions that do not have precipitate in the Long Term, graphically depicted within the boundaries defined by vertices: A17, E17, and F17.

TABLE J

EXAMPLE J - CHG/Disodium Phosphate/TWEEN 20 (poly(oxyethylene)sorbitan fatty acid ester) - FIG. 13

| Point | (CHG + Surf. + Anion) as % of total | ST & LT Stability Points | Relative % CHG | Relative % Na2HPO4 | Relative % TWEEN 20 | PPT @ 15 min | PPT @ 2 weeks |
|---|---|---|---|---|---|---|---|
| J1 | 0.2 | — | 100.0 | 0.0 | 0.0 | no | n/a |
| J2 | 0.3 | — | 82.8 | 0.0 | 17.2 | no | n/a |
| J3 | 0.3 | — | 70.6 | 0.0 | 29.4 | no | n/a |
| J4 | 0.7 | — | 32.4 | 0.0 | 67.6 | no | n/a |
| J5 | 1.2 | — | 19.4 | 0.0 | 80.7 | no | n/a |
| J6 | 2.2 | — | 10.7 | 0.0 | 89.3 | no | n/a |
| J7 | 0.3 | — | 82.8 | 17.2 | 0.0 | no | n/a |
| J8 | 0.3 | — | 70.6 | 14.7 | 14.7 | no | n/a |
| J9 | 0.4 | — | 61.5 | 12.8 | 25.6 | no | n/a |
| J10 | 0.8 | — | 30.4 | 6.3 | 63.3 | no | n/a |
| J11 | 1.3 | — | 18.6 | 3.9 | 77.5 | no | n/a |
| J12 | 2.3 | — | 10.5 | 2.2 | 87.3 | no | n/a |
| J13 | 0.3 | — | 70.6 | 29.4 | 0.0 | yes | yes |
| J14 | 0.4 | — | 61.5 | 25.6 | 12.8 | no | yes |
| J15 | 0.4 | — | 54.5 | 22.7 | 22.7 | no | yes |
| J16 | 0.8 | — | 28.6 | 11.9 | 59.5 | no | yes |
| J17 | 1.3 | I13 | 17.9 | 7.5 | 74.6 | no | no |
| J18 | 2.3 | — | 10.3 | 4.3 | 85.5 | no | no |
| J19 | 0.4 | — | 54.6 | 45.5 | 0.0 | yes | yes |
| J20 | 0.5 | — | 49.0 | 40.8 | 10.2 | yes | yes |
| J21 | 0.5 | — | 44.4 | 37.0 | 18.5 | yes | yes |
| J22 | 0.9 | — | 25.5 | 21.3 | 53.2 | no | yes |
| J23 | 1.4 | — | 16.7 | 13.9 | 69.4 | no | yes |
| J24 | 2.4 | — | 9.8 | 8.2 | 82.0 | no | no |
| J25 | 0.7 | — | 32.4 | 67.6 | 0.0 | yes | yes |
| J26 | 0.8 | — | 30.4 | 63.3 | 6.3 | yes | yes |
| J27 | 0.8 | — | 28.6 | 59.5 | 11.9 | yes | yes |
| J28 | 1.2 | — | 19.4 | 40.3 | 40.3 | no | yes |
| J29 | 1.7 | — | 13.8 | 28.7 | 57.5 | no | yes |
| J30 | 2.7 | G13 | 8.8 | 18.3 | 73.0 | no | no |
| J31 | 1.2 | — | 19.4 | 80.7 | 0.0 | yes | yes |
| J32 | 1.3 | — | 18.6 | 77.5 | 3.9 | yes | yes |
| J33 | 1.3 | — | 17.9 | 74.6 | 7.5 | yes | yes |
| J34 | 1.7 | — | 13.8 | 57.5 | 28.7 | yes | yes |
| J35 | 2.2 | — | 10.7 | 44.6 | 44.6 | yes | yes |
| J36 | 3.2 | — | 7.4 | 30.9 | 61.7 | yes | yes |
| J37 | 2.2 | — | 10.7 | 89.3 | 0.0 | yes | yes |
| J38 | 2.3 | — | 10.5 | 87.3 | 2.2 | yes | yes |
| J39 | 2.3 | — | 10.3 | 85.5 | 4.3 | yes | yes |
| J40 | 2.7 | — | 8.8 | 73.0 | 18.3 | yes | yes |
| J41 | 3.2 | — | 7.4 | 61.7 | 30.9 | yes | yes |
| J42 | 4.2 | — | 5.7 | 47.2 | 47.2 | yes | yes |
| J43 | 0.3 | — | 69.2 | 28.8 | 2.0 | no | yes |
| J44 | 0.4 | — | 55.8 | 42.2 | 2.0 | yes | yes |
| J45 | 0.4 | — | 57.8 | 40.2 | 2.0 | yes | yes |
| J46 | 0.4 | — | 59.7 | 38.3 | 2.0 | yes | yes |
| J47 | 0.4 | — | 61.4 | 36.6 | 2.0 | yes | yes |

TABLE J-continued

EXAMPLE J - CHG/Disodium Phosphate/TWEEN 20 (poly(oxyethylene)sorbitan fatty acid ester) - FIG. 13

| Point | (CHG + Surf. + Anion) as % of total | ST & LT Stability Points | Relative % CHG | Relative % Na2HPO4 | Relative % TWEEN 20 | PPT @ 15 min | PPT @ 2 weeks |
|---|---|---|---|---|---|---|---|
| J48 | 0.4 | — | 63.0 | 35.0 | 2.0 | yes | yes |
| J49 | 0.4 | — | 64.4 | 33.6 | 2.0 | yes | yes |
| J50 | 0.4 | — | 65.8 | 32.2 | 2.0 | yes | yes |
| J51 | 0.4 | — | 67.0 | 31.0 | 2.0 | yes | yes |
| J52 | 0.4 | C13 | 68.1 | 29.9 | 2.0 | no | yes |
| J53 | 0.5 | — | 44.4 | 35.2 | 20.4 | yes | yes |
| J54 | 0.5 | D13 | 44.4 | 33.3 | 22.2 | no | yes |
| J55 | 2.1 | — | 11.7 | 44.2 | 44.2 | no | yes |
| J56 | 0.7 | — | 33.3 | 33.3 | 33.3 | no | yes |
| J57 | 0.6 | — | 38.0 | 14.0 | 48.0 | no | yes |
| J58 | 0.5 | — | 52.0 | 13.0 | 35.0 | no | yes |
| J59 | 2.0 | — | 12.2 | 47.4 | 40.3 | no | yes |
| J60 | 0.8 | — | 30.0 | 45.0 | 25.0 | yes | yes |
| J61 | 0.8 | — | 28.6 | 57.2 | 14.3 | yes | yes |
| J62 | 0.8 | — | 28.6 | 54.8 | 16.7 | yes | yes |
| J63 | 0.8 | — | 28.6 | 52.4 | 19.0 | yes | yes |
| J64 | 0.8 | — | 28.6 | 50.0 | 21.4 | yes | yes |
| J65 | 0.8 | — | 28.6 | 47.6 | 23.8 | yes | yes |
| J66 | 0.8 | — | 28.6 | 45.3 | 26.2 | yes | yes |
| J67 | 0.8 | E13 | 28.6 | 42.9 | 28.6 | no | yes |
| J68 | 1.7 | F13 | 13.8 | 54.6 | 31.6 | no | yes |
| J69 | 0.6 | — | 40.0 | 23.0 | 37.0 | no | yes |
| J70 | 10.9 | — | 2.2 | 27.8 | 70.0 | yes | yes |
| J71 | 4.0 | — | 6.0 | 24.0 | 70.0 | yes | yes |
| J72 | 12.6 | — | 1.9 | 18.1 | 80.0 | yes | yes |
| J73 | 4.0 | H13 | 6.0 | 14.0 | 80.0 | no | no |
| J74 | 4.0 | — | 6.0 | 21.0 | 73.0 | yes | yes |
| J75 | — | A13 | 1.2 | 1.2 | 97.6 | — | — |
| J76 | — | B13 | 81.1 | 16.9 | 2.0 | — | — |

The lightly shaded area of FIG. 13 represents compositions that do not have precipitate in the Short Term, graphically depicted within the boundaries defined by vertices: A13, B13, C13, D13, E13, F13, G13, and H13. The darker shaded area of FIG. 13 represents compositions that do not have precipitate in the Long Term, graphically depicted within the boundaries defined by vertices: A13, I13, G13, and H13.

TABLE K

EXAMPLE K-CHG/Sodium dihydrogen phosphate/TWEEN 20 (poly(oxyethylene)sorbitan fatty acid ester)-FIG. 12

| Point | (CHG + Surf. + Anion) as % of total | ST & LT Stability Points | Relative % CHG | Relative % NaH2PO4 | Relative % TWEEN 20 | PPT @ 15 min | PPT @ 2 weeks |
|---|---|---|---|---|---|---|---|
| K1 | 0.2 | — | 100.0 | 0.0 | 0.0 | no | n/a |
| K2 | 0.3 | — | 82.8 | 0.0 | 17.2 | no | n/a |
| K3 | 0.3 | — | 70.6 | 0.0 | 29.4 | no | n/a |
| K4 | 0.7 | — | 32.4 | 0.0 | 67.6 | no | n/a |
| K5 | 1.2 | — | 19.4 | 0.0 | 80.7 | no | n/a |
| K6 | 2.2 | — | 10.7 | 0.0 | 89.3 | no | n/a |
| K7 | 0.3 | — | 82.8 | 17.2 | 0.0 | no | n/a |
| K8 | 0.3 | — | 70.6 | 14.7 | 14.7 | no | n/a |
| K9 | 0.4 | — | 61.5 | 12.8 | 25.6 | no | n/a |
| K10 | 0.8 | — | 30.4 | 6.3 | 63.3 | no | n/a |
| K11 | 1.3 | — | 18.6 | 3.9 | 77.5 | no | n/a |
| K12 | 2.3 | — | 10.5 | 2.2 | 87.3 | no | n/a |
| K13 | 0.3 | — | 70.6 | 29.4 | 0.0 | yes | yes |
| K14 | 0.4 | — | 61.5 | 25.6 | 12.8 | no | yes |
| K15 | 0.4 | — | 54.5 | 22.7 | 22.7 | no | yes |
| K16 | 0.8 | — | 28.6 | 11.9 | 59.5 | no | yes |
| K17 | 1.3 | K12 | 17.9 | 7.5 | 74.6 | no | no |
| K18 | 2.3 | — | 10.3 | 4.3 | 85.5 | no | no |
| K19 | 0.4 | — | 54.6 | 45.5 | 0.0 | yes | yes |
| K20 | 0.5 | — | 49.0 | 40.8 | 10.2 | yes | yes |
| K21 | 0.5 | — | 44.4 | 37.0 | 18.5 | yes | yes |

TABLE K-continued

EXAMPLE K-CHG/Sodium dihydrogen phosphate/TWEEN 20
(poly(oxyethylene)sorbitan fatty acid ester)-FIG. 12

| Point | (CHG + Surf. + Anion) as % of total | ST & LT Stability Points | Relative % CHG | Relative % NaH2PO4 | Relative % TWEEN 20 | PPT @ 15 min | PPT @ 2 weeks |
|---|---|---|---|---|---|---|---|
| K22 | 0.9 | — | 25.5 | 21.3 | 53.2 | no | yes |
| K23 | 1.4 | — | 16.7 | 13.9 | 69.4 | no | yes |
| K24 | 2.4 | — | 9.8 | 8.2 | 82.0 | no | no |
| K25 | 0.7 | — | 32.4 | 67.6 | 0.0 | yes | yes |
| K26 | 0.8 | — | 30.4 | 63.3 | 6.3 | yes | yes |
| K27 | 0.8 | — | 28.6 | 59.5 | 11.9 | yes | yes |
| K28 | 1.2 | — | 19.4 | 40.3 | 40.3 | yes | yes |
| K29 | 1.7 | — | 13.8 | 28.7 | 57.5 | no | yes |
| K30 | 2.7 | — | 8.8 | 18.3 | 73.0 | no | no |
| K31 | 1.2 | — | 19.4 | 80.7 | 0.0 | yes | yes |
| K32 | 1.3 | — | 18.6 | 77.5 | 3.9 | yes | yes |
| K33 | 1.3 | — | 17.9 | 74.6 | 7.5 | yes | yes |
| K34 | 1.7 | — | 13.8 | 57.5 | 28.7 | yes | yes |
| K35 | 2.2 | — | 10.7 | 44.6 | 44.6 | yes | yes |
| K36 | 3.2 | — | 7.4 | 30.9 | 61.7 | yes | yes |
| K37 | 2.2 | — | 10.7 | 89.3 | 0.0 | yes | yes |
| K38 | 2.3 | — | 10.5 | 87.3 | 2.2 | yes | yes |
| K39 | 2.3 | — | 10.3 | 85.5 | 4.3 | yes | yes |
| K40 | 2.7 | — | 8.8 | 73.0 | 18.3 | yes | yes |
| K41 | 3.2 | — | 7.4 | 61.7 | 30.9 | yes | yes |
| K42 | 4.2 | — | 5.7 | 47.2 | 47.2 | yes | yes |
| K43 | 0.3 | — | 69.2 | 28.8 | 2.0 | no | yes |
| K44 | 0.4 | C12 | 55.8 | 42.2 | 2.0 | no | yes |
| K45 | 0.5 | D12 | 44.4 | 35.2 | 20.4 | no | yes |
| K46 | 1.2 | G12 | 19.4 | 36.3 | 44.4 | no | yes |
| K47 | 0.7 | — | 33.3 | 33.3 | 33.3 | no | yes |
| K48 | 0.6 | — | 38.0 | 14.0 | 48.0 | no | yes |
| K49 | 0.5 | — | 52.0 | 13.0 | 35.0 | no | yes |
| K50 | 1.4 | — | 17.4 | 37.2 | 45.4 | no | yes |
| K51 | 0.8 | — | 30.0 | 45.0 | 25.0 | no | yes |
| K52 | 0.8 | — | 28.6 | 57.2 | 14.3 | yes | yes |
| K53 | 0.8 | — | 28.6 | 54.8 | 16.7 | no | yes |
| K54 | 0.6 | — | 40.0 | 23.0 | 37.0 | no | yes |
| K55 | 0.8 | — | 31.4 | 51.9 | 16.7 | no | yes |
| K56 | 0.7 | — | 34.3 | 49.1 | 16.7 | no | yes |
| K57 | 0.6 | — | 37.1 | 46.2 | 16.7 | no | yes |
| K58 | 0.6 | — | 40.0 | 43.3 | 16.7 | no | yes |
| K59 | 0.6 | E12 | 42.9 | 40.5 | 16.7 | no | yes |
| K60 | 0.9 | F12 | 22.8 | 60.5 | 16.7 | no | yes |
| K61 | 1.1 | — | 22.9 | 60.5 | 16.7 | no | yes |
| K62 | 0.7 | — | 35.0 | 45.0 | 20.0 | no | yes |
| K63 | 1.6 | — | 15.5 | 38.0 | 46.5 | no | yes |
| K64 | 1.8 | — | 13.5 | 38.9 | 47.5 | no | yes |
| K65 | 2.1 | H12 | 11.6 | 39.8 | 48.6 | no | yes |
| K66 | 2.5 | — | 9.7 | 40.7 | 49.7 | yes | yes |
| K67 | 10.9 | — | 2.2 | 27.8 | 70.0 | no | no |
| K68 | 4.0 | I12 | 6.0 | 24.0 | 70.0 | no | no |
| K69 | 12.6 | — | 1.9 | 18.1 | 80.0 | no | no |
| K70 | — | A12 | 1.2 | 1.2 | 97.6 | — | — |
| K71 | — | B12 | 81.1 | 16.9 | 2.0 | — | — |
| K72 | — | J12 | 1.2 | 28.8 | 70.0 | — | — |

The lightly shaded area of FIG. 12 represents compositions that do not have precipitate in the Short Term, graphically depicted within the boundaries defined by vertices: A12, B12, C12, D12, E12, F12, G12, H12, I12, and J12. The darker shaded area of FIG. 12 represents compositions that do not have precipitate in the Long Term, graphically depicted within the boundaries defined by vertices: A12, K12, I12, and J12.

TABLE L

EXAMPLE L-CHG/Sodium bicarbonate (pH 7)/TWEEN 20 (poly(oxyethylene)sorbitan fatty acid ester)-FIG. 14

| Point | (CHG + Surf. + Anion) as % of total | ST & LT Stability Points | Relative % CHG | Relative % NaHCO3 (pH 7) | Relative % TWEEN 20 | PPT @ 15 min | PPT @ 2 weeks |
|---|---|---|---|---|---|---|---|
| L1 | 0.2 | — | 100.0 | 0.0 | 0.0 | no | n/a |
| L2 | 0.3 | — | 82.8 | 0.0 | 17.2 | no | n/a |
| L3 | 0.3 | — | 70.6 | 0.0 | 29.4 | no | n/a |
| L4 | 0.7 | — | 32.4 | 0.0 | 67.6 | no | n/a |
| L5 | 1.2 | — | 19.4 | 0.0 | 80.7 | no | n/a |
| L6 | 2.2 | — | 10.7 | 0.0 | 89.3 | no | n/a |
| L7 | 0.3 | — | 82.8 | 17.2 | 0.0 | no | n/a |
| L8 | 0.3 | — | 70.6 | 14.7 | 14.7 | no | n/a |
| L9 | 0.4 | — | 61.5 | 12.8 | 25.6 | no | n/a |
| L10 | 0.8 | — | 30.4 | 6.3 | 63.3 | no | n/a |
| L11 | 1.3 | — | 18.6 | 3.9 | 77.5 | no | n/a |
| L12 | 2.3 | — | 10.5 | 2.2 | 87.3 | no | n/a |
| L13 | 0.3 | — | 70.6 | 29.4 | 0.0 | no | n/a |
| L14 | 0.4 | — | 61.5 | 25.6 | 12.8 | no | n/a |
| L15 | 0.4 | — | 54.5 | 22.7 | 22.7 | no | n/a |
| L16 | 0.8 | — | 28.6 | 11.9 | 59.5 | no | n/a |
| L17 | 1.3 | — | 17.9 | 7.5 | 74.6 | no | n/a |
| L18 | 2.3 | — | 10.3 | 4.3 | 85.5 | no | n/a |
| L19 | 0.4 | — | 54.6 | 45.5 | 0.0 | no | n/a |
| L20 | 0.5 | — | 49.0 | 40.8 | 10.2 | no | n/a |
| L21 | 0.5 | — | 44.4 | 37.0 | 18.5 | no | n/a |
| L22 | 0.9 | — | 25.5 | 21.3 | 53.2 | no | n/a |
| L23 | 1.4 | — | 16.7 | 13.9 | 69.4 | no | n/a |
| L24 | 2.4 | — | 9.8 | 8.2 | 82.0 | no | n/a |
| L25 | 0.7 | — | 32.4 | 67.6 | 0.0 | no | n/a |
| L26 | 0.8 | — | 30.4 | 63.3 | 6.3 | no | n/a |
| L27 | 0.8 | — | 28.6 | 59.5 | 11.9 | no | n/a |
| L28 | 1.2 | — | 19.4 | 40.3 | 40.3 | no | n/a |
| L29 | 1.7 | — | 13.8 | 28.7 | 57.5 | no | n/a |
| L30 | 2.7 | — | 8.8 | 18.3 | 73.0 | no | n/a |
| L31 | 1.2 | — | 19.4 | 80.7 | 0.0 | no | n/a |
| L32 | 1.3 | — | 18.6 | 77.5 | 3.9 | no | n/a |
| L33 | 1.3 | — | 17.9 | 74.6 | 7.5 | no | n/a |
| L34 | 1.7 | — | 13.8 | 57.5 | 28.7 | no | n/a |
| L35 | 2.2 | — | 10.7 | 44.6 | 44.6 | no | n/a |
| L36 | 3.2 | — | 7.4 | 30.9 | 61.7 | no | n/a |
| L37 | 2.2 | — | 10.7 | 89.3 | 0.0 | yes | yes |
| L38 | 2.3 | — | 10.5 | 87.3 | 2.2 | yes | yes |
| L39 | 2.3 | C14 | 10.3 | 85.5 | 4.3 | no | yes |
| L40 | 2.7 | — | 8.8 | 73.0 | 18.3 | no | yes |
| L41 | 3.2 | D14 | 7.4 | 61.7 | 30.9 | no | yes |
| L42 | 4.2 | — | 5.7 | 47.2 | 47.2 | no | no |
| L43 | 2.7 | — | 9.0 | 86.7 | 4.3 | yes | yes |
| L44 | 2.7 | — | 9.0 | 85.5 | 5.5 | yes | yes |
| L45 | 2.0 | — | 12.0 | 70.0 | 18.0 | no | no |
| L46 | 1.7 | G14 | 14.0 | 80.0 | 6.0 | no | no |
| L47 | 6.7 | — | 3.6 | 65.5 | 30.9 | yes | yes |
| L48 | 6.0 | — | 4.0 | 77.8 | 18.3 | yes | yes |
| L49 | 8.0 | — | 3.0 | 49.8 | 47.2 | no | yes |
| L50 | 9.6 | — | 2.5 | 35.8 | 61.7 | no | no |
| L51 | 11.4 | — | 2.1 | 24.9 | 73.0 | no | no |
| L52 | 12.6 | — | 1.9 | 18.1 | 80.0 | no | no |
| L53 | 6.7 | — | 3.6 | 62.5 | 33.9 | yes | yes |
| L54 | 6.7 | — | 3.6 | 59.4 | 37.0 | yes | yes |
| L55 | 6.7 | — | 3.6 | 56.3 | 40.1 | no | yes |
| L56 | 1.4 | F14 | 17.6 | 76.4 | 6.0 | no | no |
| L57 | — | A14 | 1.2 | 1.2 | 97.6 | — | — |
| L58 | — | B14 | 17.9 | 77.8 | 4.3 | — | — |
| L59 | — | E14 | 1.2 | 52.9 | 45.9 | — | — |
| L60 | — | H14 | 1.2 | 30.8 | 68.0 | — | — |

The lightly shaded area of FIG. 14 represents compositions that do not have precipitate in the Short Term, graphically depicted within the boundaries defined by vertices: A14, B14, C14, D14, and E14. The darker shaded area of FIG. 14 represents compositions that do not have precipitate in the Long Term, graphically depicted within the boundaries defined by vertices: A14, F14, G14, and H14.

TABLE M

EXAMPLE M-CHG/Sodium bicarbonate (pH 9.1)/TWEEN 20 (poly(oxyethylene)sorbitan fatty acid ester)-FIG. 15

| Point | (CHG + Surf. + Anion) as % of total | ST & LT Stability Points | Relative % CHG | Relative % NaHCO3 (pH 9.1) | Relative % TWEEN 20 | PPT @ 15 min | PPT @ 2 weeks |
|---|---|---|---|---|---|---|---|
| M1 | 0.2 | — | 100.0 | 0.0 | 0.0 | no | n/a |
| M2 | 0.3 | — | 82.8 | 0.0 | 17.2 | no | n/a |
| M3 | 0.3 | — | 70.6 | 0.0 | 29.4 | no | n/a |
| M4 | 0.7 | — | 32.4 | 0.0 | 67.6 | no | n/a |
| M5 | 1.2 | — | 19.4 | 0.0 | 80.7 | no | n/a |
| M6 | 2.2 | — | 10.7 | 0.0 | 89.3 | no | n/a |
| M7 | 0.3 | — | 82.8 | 17.2 | 0.0 | no | n/a |
| M8 | 0.3 | — | 70.6 | 14.7 | 14.7 | no | n/a |
| M9 | 0.4 | — | 61.5 | 12.8 | 25.6 | no | n/a |
| M10 | 0.8 | — | 30.4 | 6.3 | 63.3 | no | n/a |
| M11 | 1.3 | — | 18.6 | 3.9 | 77.5 | no | n/a |
| M12 | 2.3 | — | 10.5 | 2.2 | 87.3 | no | n/a |
| M13 | 0.3 | — | 70.6 | 29.4 | 0.0 | no | n/a |
| M14 | 0.4 | — | 61.5 | 25.6 | 12.8 | no | n/a |
| M15 | 0.4 | — | 54.5 | 22.7 | 22.7 | no | n/a |
| M16 | 0.8 | — | 28.6 | 11.9 | 59.5 | no | n/a |
| M17 | 1.3 | — | 17.9 | 7.5 | 74.6 | no | n/a |
| M18 | 2.3 | — | 10.3 | 4.3 | 85.5 | no | n/a |
| M19 | 0.4 | — | 54.6 | 45.5 | 0.0 | no | n/a |
| M20 | 0.5 | — | 49.0 | 40.8 | 10.2 | no | n/a |
| M21 | 0.5 | — | 44.4 | 37.0 | 18.5 | no | n/a |
| M22 | 0.9 | — | 25.5 | 21.3 | 53.2 | no | n/a |
| M23 | 1.4 | — | 16.7 | 13.9 | 69.4 | no | n/a |
| M24 | 2.4 | — | 9.8 | 8.2 | 82.0 | no | n/a |
| M25 | 0.7 | — | 32.4 | 67.6 | 0.0 | no | n/a |
| M26 | 0.8 | — | 30.4 | 63.3 | 6.3 | no | n/a |
| M27 | 0.8 | — | 28.6 | 59.5 | 11.9 | no | n/a |
| M28 | 1.2 | — | 19.4 | 40.3 | 40.3 | no | n/a |
| M29 | 1.7 | — | 13.8 | 28.7 | 57.5 | no | n/a |
| M30 | 2.7 | — | 8.8 | 18.3 | 73.0 | no | n/a |
| M31 | 1.2 | — | 19.4 | 80.7 | 0.0 | no | n/a |
| M32 | 1.3 | — | 18.6 | 77.5 | 3.9 | no | n/a |
| M33 | 1.3 | — | 17.9 | 74.6 | 7.5 | no | n/a |
| M34 | 1.7 | — | 13.8 | 57.5 | 28.7 | no | n/a |
| M35 | 2.2 | — | 10.7 | 44.6 | 44.6 | no | n/a |
| M36 | 3.2 | — | 7.4 | 30.9 | 61.7 | no | n/a |
| M37 | 2.2 | — | 10.7 | 89.3 | 0.0 | yes | yes |
| M38 | 2.3 | C15 | 10.5 | 87.3 | 2.2 | no | yes |
| M39 | 2.3 | — | 10.3 | 85.5 | 4.3 | no | yes |
| M40 | 2.7 | — | 8.8 | 73.0 | 18.3 | no | yes |
| M41 | 3.2 | — | 7.4 | 61.7 | 30.9 | no | yes |
| M42 | 4.2 | D15 | 5.7 | 47.2 | 47.2 | no | no |
| M43 | 2.7 | — | 9.0 | 88.8 | 2.2 | yes | yes |
| M44 | 2.7 | — | 9.0 | 87.3 | 3.7 | yes | yes |
| M45 | 2.0 | — | 12.0 | 70.0 | 18.0 | no | yes |
| M46 | 1.7 | — | 14.0 | 80.0 | 6.0 | no | yes |
| M47 | 6.7 | — | 3.6 | 65.5 | 30.9 | yes | yes |
| M48 | 6.0 | — | 4.0 | 77.8 | 18.3 | yes | yes |
| M49 | 8.0 | — | 3.0 | 49.8 | 47.2 | yes | yes |
| M50 | 9.6 | — | 2.5 | 35.8 | 61.7 | no | yes |
| M51 | 11.4 | — | 2.1 | 24.9 | 73.0 | no | yes |
| M52 | 12.6 | — | 1.9 | 18.1 | 80.0 | no | no |
| M53 | 8.0 | — | 3.0 | 45.1 | 51.9 | no | yes |
| M54 | — | A15 | 1.2 | 1.2 | 97.6 | — | — |
| M55 | — | B15 | 18.3 | 79.5 | 2.2 | — | — |
| M56 | — | E15 | 1.2 | 43.7 | 55.1 | — | — |
| M57 | — | F15 | 10.0 | 42.8 | 47.2 | — | — |
| M58 | — | G15 | 1.2 | 12.7 | 86.1 | — | — |

The lightly shaded area of FIG. 15 represents compositions that do not have precipitate in the Short Term, graphically depicted within the boundaries defined by vertices: A15, B15, C15, D15, and E15. The darker shaded area of FIG. 15 represents compositions that do not have precipitate in the Long Term, graphically depicted within the boundaries defined by vertices: A15, F15, D15, and G15.

TABLE N

EXAMPLE N-CHG/FD&C RED 40/TWEEN 20
(poly(oxyethylene)sorbitan fatty acid ester)-FIG. 16

| Point | (CHG + Surf. + Anion) as % of total | ST & LT Stability Points | Relative % CHG | Relative % FD&C Red 40 | Relative % TWEEN 20 | PPT @ 15 min | PPT @ 2 weeks |
|---|---|---|---|---|---|---|---|
| N1 | 0.2 | — | 100.0 | 0.0 | 0.0 | no | n/a |
| N2 | 0.3 | — | 82.8 | 0.0 | 17.2 | no | n/a |
| N3 | 0.3 | — | 70.6 | 0.0 | 29.4 | no | n/a |
| N4 | 0.7 | — | 32.4 | 0.0 | 67.6 | no | n/a |
| N5 | 1.2 | — | 19.4 | 0.0 | 80.7 | no | n/a |
| N6 | 2.2 | — | 10.7 | 0.0 | 89.3 | no | n/a |
| N7 | 0.3 | — | 82.8 | 17.2 | 0.0 | yes | yes |
| N8 | 0.3 | — | 70.6 | 14.7 | 14.7 | yes | yes |
| N9 | 0.4 | — | 61.5 | 12.8 | 25.6 | yes | yes |
| N10 | 0.8 | — | 30.4 | 6.3 | 63.3 | yes | yes |
| N11 | 1.3 | — | 18.6 | 3.9 | 77.5 | yes | yes |
| N12 | 2.3 | B16 | 10.5 | 2.2 | 87.3 | no | no |
| N13 | 0.3 | — | 70.6 | 29.4 | 0.0 | yes | yes |
| N14 | 0.4 | — | 61.5 | 25.6 | 12.8 | yes | yes |
| N15 | 0.4 | — | 54.5 | 22.7 | 22.7 | yes | yes |
| N16 | 0.8 | — | 28.6 | 11.9 | 59.5 | yes | yes |
| N17 | 1.3 | — | 17.9 | 7.5 | 74.6 | yes | yes |
| N18 | 2.3 | — | 10.3 | 4.3 | 85.5 | no | yes |
| N19 | 0.4 | — | 54.6 | 45.5 | 0.0 | yes | yes |
| N20 | 0.5 | — | 49.0 | 40.8 | 10.2 | yes | yes |
| N21 | 0.5 | — | 44.4 | 37.0 | 18.5 | yes | yes |
| N22 | 0.9 | — | 25.5 | 21.3 | 53.2 | yes | yes |
| N23 | 1.4 | — | 16.7 | 13.9 | 69.4 | yes | yes |
| N24 | 2.4 | — | 9.8 | 8.2 | 82.0 | no | yes |
| N25 | 0.7 | — | 32.4 | 67.6 | 0.0 | yes | yes |
| N26 | 0.8 | — | 30.4 | 63.3 | 6.3 | yes | yes |
| N27 | 0.8 | — | 28.6 | 59.5 | 11.9 | yes | yes |
| N28 | 1.2 | — | 19.4 | 40.3 | 40.3 | yes | yes |
| N29 | 1.7 | — | 13.8 | 28.7 | 57.5 | yes | yes |
| N30 | 2.7 | — | 8.8 | 18.3 | 73.0 | no | yes |
| N31 | 1.2 | — | 19.4 | 80.7 | 0.0 | yes | yes |
| N32 | 1.3 | — | 18.6 | 77.5 | 3.9 | yes | yes |
| N33 | 1.3 | — | 17.9 | 74.6 | 7.5 | yes | yes |
| N34 | 1.7 | — | 13.8 | 57.5 | 28.7 | yes | yes |
| N35 | 2.2 | — | 10.7 | 44.6 | 44.6 | yes | yes |
| N36 | 3.2 | — | 7.4 | 30.9 | 61.7 | no | yes |
| N37 | 2.2 | — | 10.7 | 89.3 | 0.0 | yes | yes |
| N38 | 2.3 | — | 10.5 | 87.3 | 2.2 | yes | yes |
| N39 | 2.3 | — | 10.3 | 85.5 | 4.3 | yes | yes |
| N40 | 2.7 | — | 8.8 | 73.0 | 18.3 | yes | yes |
| N41 | 3.2 | — | 7.4 | 61.7 | 30.9 | yes | yes |
| N42 | 4.2 | — | 5.7 | 47.2 | 47.2 | yes | yes |
| N43 | 4.2 | C16 | 5.7 | 44.8 | 49.5 | no | yes |
| N44 | 1.9 | — | 12.4 | 29.2 | 58.4 | yes | yes |
| N45 | 2.2 | — | 11.0 | 29.7 | 59.3 | yes | yes |
| N46 | 2.5 | — | 9.7 | 30.1 | 60.2 | yes | yes |
| N47 | 2.9 | — | 8.3 | 30.6 | 61.1 | yes | yes |
| N48 | 1.4 | — | 16.7 | 4.0 | 79.3 | yes | yes |
| N49 | 1.6 | — | 14.9 | 4.1 | 81.1 | yes | yes |
| N50 | 1.8 | — | 13.0 | 4.1 | 82.8 | yes | yes |
| N51 | 2.2 | — | 11.2 | 4.2 | 84.6 | yes | yes |
| N52 | 8.1 | E16 | 3.0 | 47.1 | 49.9 | no | no |
| N53 | — | A16 | 1.2 | 1.2 | 97.6 | — | — |
| N54 | — | D16 | 1.2 | 49.3 | 49.5 | — | — |

The lightly shaded area of FIG. 16 represents compositions that do not have precipitate in the Short Term, graphically depicted within the boundaries defined by vertices: A16, B16, C16, and D16. The darker shaded area of FIG. 16 represents compositions that do not have precipitate in the Long Term, graphically depicted within the boundaries defined by vertices: A16, B16, E16, and D16.

TABLE O

EXAMPLE O-Octenidine HCl (OCT)/NaSaccharin/MACKAM L ((C8-C22)alkylamido(C2-C4)alkyl betaine)-FIG. 19

| Point | (OCT + Surf. + Anion) as % of total | Short Term Stability Points | Relative % OCT | Relative % NaSaccharin | Relative % Active Surfactant | PPT @ 15 min | PPT @ 3 weeks |
|---|---|---|---|---|---|---|---|
| O1 | 0.2 | — | 100.0 | 0.0 | 0.0 | no | no |
| O2 | 0.3 | — | 94.1 | 0.0 | 5.9 | no | no |
| O3 | 0.3 | — | 88.9 | 0.0 | 11.1 | no | no |
| O4 | 0.4 | — | 61.5 | 0.0 | 38.5 | no | no |
| O5 | 0.5 | — | 44.4 | 0.0 | 55.6 | no | no |
| O6 | 0.8 | — | 28.6 | 0.0 | 71.4 | no | no |
| O7 | 0.3 | — | 82.8 | 17.2 | 0.0 | yes | yes |
| O8 | 0.3 | — | 78.7 | 16.4 | 4.9 | yes | yes |
| O9 | 0.3 | — | 75.0 | 15.6 | 9.4 | yes | yes |
| O10 | 0.4 | — | 54.5 | 11.4 | 34.1 | yes | yes |
| O11 | 0.6 | — | 40.7 | 8.5 | 50.8 | yes | yes |
| O12 | 0.9 | B19 | 27.0 | 5.6 | 67.4 | no | no |
| O13 | 0.3 | — | 70.6 | 29.4 | 0.0 | yes | yes |
| O14 | 0.4 | — | 67.6 | 28.2 | 4.2 | yes | yes |
| O15 | 0.4 | — | 64.9 | 27.0 | 8.1 | yes | yes |
| O16 | 0.5 | — | 49.0 | 20.4 | 30.6 | yes | yes |
| O17 | 0.6 | — | 37.5 | 15.6 | 46.9 | yes | yes |
| O18 | 0.9 | C19 | 25.5 | 10.7 | 63.8 | no | no |
| O19 | 0.4 | — | 54.6 | 45.5 | 0.0 | yes | yes |
| O20 | 0.5 | — | 52.7 | 44.0 | 3.3 | yes | yes |
| O21 | 0.5 | — | 51.1 | 42.6 | 6.4 | yes | yes |
| O22 | 0.6 | — | 40.7 | 33.9 | 25.4 | yes | yes |
| O23 | 0.7 | — | 32.4 | 27.0 | 40.5 | yes | yes |
| O24 | 1.0 | — | 23.1 | 19.2 | 57.7 | yes | yes |
| O25 | 0.7 | — | 32.4 | 67.6 | 0.0 | yes | yes |
| O26 | 0.8 | — | 31.8 | 66.2 | 2.0 | yes | yes |
| O27 | 0.8 | — | 31.2 | 64.9 | 3.9 | yes | yes |
| O28 | 0.9 | — | 27.0 | 56.2 | 16.9 | yes | yes |
| O29 | 1.0 | — | 23.1 | 48.1 | 28.8 | yes | yes |
| O30 | 1.3 | — | 17.9 | 37.3 | 44.8 | yes | yes |
| O31 | 1.2 | — | 19.4 | 80.7 | 0.0 | yes | yes |
| O32 | 1.3 | — | 19.1 | 79.7 | 1.2 | yes | yes |
| O33 | 1.3 | — | 18.9 | 78.7 | 2.4 | yes | yes |
| O34 | 1.4 | — | 17.3 | 71.9 | 10.8 | yes | yes |
| O35 | 1.5 | — | 15.6 | 64.9 | 19.5 | yes | yes |
| O36 | 1.8 | — | 13.0 | 54.3 | 32.6 | yes | yes |
| O37 | 2.2 | — | 10.7 | 89.3 | 0.0 | yes | yes |
| O38 | 2.3 | — | 10.6 | 88.7 | 0.7 | yes | yes |
| O39 | 2.3 | — | 10.6 | 88.1 | 1.3 | yes | yes |
| O40 | 2.4 | — | 10.0 | 83.7 | 6.3 | yes | yes |
| O41 | 2.5 | — | 9.5 | 78.7 | 11.8 | yes | yes |
| O42 | 2.8 | — | 8.5 | 70.4 | 21.1 | yes | yes |
| O43 | 4.5 | — | 5.4 | 30.8 | 63.9 | no | no |
| O44 | — | A19 | 1.2 | 1.2 | 97.6 | — | — |
| O45 | — | D19 | 1.2 | 34.9 | 63.9 | — | — |

The lightly shaded area of FIG. 19 represents compositions that do not have precipitate in the Short Term, graphically depicted within the boundaries defined by vertices: A19, B19, C19, and D19. The same compositions that did not have precipitate in the Short Term also did not have precipitate in the Long Term.

TABLE P

EXAMPLE P-PHMB/NaSaccharin/MACKAM L ((C8-C22)alkylamido(C2-C4)alkyl betaine)-FIG. 18

| Point | (PHMB + Surf. + Anion) as % of total | Short Term Stability Points | Relative % PHMB | Relative % NaSaccharin | Relative % Active Surfactant | PPT @ 15 min | PPT @ 3 weeks |
|---|---|---|---|---|---|---|---|
| P1  | 0.2 | —   | 100.0 | 0.0  | 0.0  | no  | no  |
| P2  | 0.3 | —   | 94.1  | 0.0  | 5.9  | no  | no  |
| P3  | 0.3 | —   | 88.9  | 0.0  | 11.1 | no  | no  |
| P4  | 0.4 | —   | 61.5  | 0.0  | 38.5 | no  | no  |
| P5  | 0.5 | —   | 44.4  | 0.0  | 55.6 | no  | no  |
| P6  | 0.8 | —   | 28.6  | 0.0  | 71.4 | no  | no  |
| P7  | 0.3 | —   | 82.8  | 17.2 | 0.0  | no  | no  |
| P8  | 0.3 | —   | 78.7  | 16.4 | 4.9  | no  | no  |
| P9  | 0.3 | —   | 75.0  | 15.6 | 9.4  | no  | no  |
| P10 | 0.4 | —   | 54.5  | 11.4 | 34.1 | no  | no  |
| P11 | 0.6 | —   | 40.7  | 8.5  | 50.8 | no  | no  |
| P12 | 0.9 | —   | 27.0  | 5.6  | 67.4 | no  | no  |
| P13 | 0.3 | —   | 70.6  | 29.4 | 0.0  | yes | yes |
| P14 | 0.4 | C18 | 67.6  | 28.2 | 4.2  | no  | no  |
| P15 | 0.4 | —   | 64.9  | 27.0 | 8.1  | no  | no  |
| P16 | 0.5 | —   | 49.0  | 20.4 | 30.6 | no  | no  |
| P17 | 0.6 | —   | 37.5  | 15.6 | 46.9 | no  | no  |
| P18 | 0.9 | —   | 25.5  | 10.6 | 63.8 | no  | no  |
| P19 | 0.4 | —   | 54.6  | 45.5 | 0.0  | yes | yes |
| P20 | 0.5 | —   | 52.7  | 44.0 | 3.3  | yes | yes |
| P21 | 0.5 | —   | 51.1  | 42.6 | 6.4  | yes | yes |
| P22 | 0.6 | —   | 40.7  | 33.9 | 25.4 | no  | no  |
| P23 | 0.7 | —   | 32.4  | 27.0 | 40.5 | no  | no  |
| P24 | 1.0 | —   | 23.1  | 19.2 | 57.7 | no  | no  |
| P25 | 0.7 | —   | 32.4  | 67.6 | 0.0  | yes | yes |
| P26 | 0.8 | —   | 31.8  | 66.2 | 2.0  | yes | yes |
| P27 | 0.8 | —   | 31.2  | 64.9 | 3.9  | yes | yes |
| P28 | 0.9 | —   | 27.0  | 56.2 | 16.9 | yes | yes |
| P29 | 1.0 | —   | 23.1  | 48.1 | 28.8 | no  | no  |
| P30 | 1.3 | —   | 17.9  | 37.3 | 44.8 | no  | no  |
| P31 | 1.2 | —   | 19.4  | 80.7 | 0.0  | yes | yes |
| P32 | 1.3 | —   | 19.1  | 79.7 | 1.2  | yes | yes |
| P33 | 1.3 | —   | 18.9  | 78.7 | 2.4  | yes | yes |
| P34 | 1.4 | —   | 17.3  | 71.9 | 10.8 | yes | yes |
| P35 | 1.5 | —   | 15.6  | 64.9 | 19.5 | yes | yes |
| P36 | 1.8 | E18 | 13.0  | 54.3 | 32.6 | no  | no  |
| P37 | 2.2 | —   | 10.7  | 89.3 | 0.0  | yes | yes |
| P38 | 2.3 | —   | 10.6  | 88.7 | 0.7  | yes | yes |
| P39 | 2.3 | —   | 10.6  | 88.1 | 1.3  | yes | yes |
| P40 | 2.4 | —   | 10.0  | 83.7 | 6.3  | yes | yes |
| P41 | 2.5 | —   | 9.5   | 78.7 | 11.8 | yes | yes |
| P42 | 2.8 | —   | 8.5   | 70.4 | 21.1 | yes | yes |
| P43 | 0.5 | —   | 52.6  | 21.9 | 25.4 | no  | no  |
| P44 | 5.4 | —   | 4.5   | 70.1 | 25.4 | yes | yes |
| P45 | 5.5 | —   | 4.4   | 63.0 | 32.6 | yes | yes |
| P46 | 5.6 | —   | 4.3   | 50.9 | 44.8 | no  | no  |
| P47 | —   | A18 | 1.2   | 1.2  | 97.6 | —   | —   |
| P48 | —   | B18 | 79.2  | 16.6 | 4.2  | —   | —   |
| P49 | —   | F18 | 1.2   | 49.7 | 49.1 | —   | —   |
| P50 | 0.4 | D18 | 54    | 31   | 15   | no  | no  |
| P51 | 1.3 | —   | 19.1  | 55.6 | 25.3 | yes | yes |
| P52 | 0.6 | —   | 41.7  | 41.7 | 16.7 | yes | yes |
| P53 | 0.6 | —   | 40.2  | 38.6 | 21.2 | no  | no  |

The lightly shaded area of FIG. 18 represents compositions that do not have precipitate in the Short Term, graphically depicted within the boundaries defined by vertices: A18, B18, C18, D18, E18, and F18. The same compositions that did not have precipitate in the Short Term also did not have precipitate in the Long Term.

TABLE Q

EXAMPLE Q - CHG/Yellow 6/TWEEN 20

| Point | (CHG + Surf. + Anion) as % of total | Relative % CHG | Relative % Yellow 6 | Relative % TWEEN 20 | PPT @ 15 min |
|---|---|---|---|---|---|
| Q1 | 2.3 | 10.5 | 2.2 | 87.3 | no |
| Q2 | 2.3 | 10.3 | 4.3 | 85.5 | yes |
| Q3 | 2.4 | 9.8 | 8.2 | 82.0 | yes |
| Q4 | 1.6 | 5.7 | 44.8 | 49.5 | yes |

Example Q was prepared and tested in the same fashion as Examples A-P

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. An antiseptic composition comprising:
a multivalent cationic antiseptic selected from the group consisting of chlorhexidine acetate, chlorhexidine gluconate, chlorhexidine lactate, chlorhexidine methosulfate, and polyhexamethylene biguanide hydrochloride, and a combination thereof,
wherein the multivalent cationic antiseptic is present in an amount of 0.05 to 0.5 percent based upon the weight of the antiseptic composition;
an anionic compound selected from sodium carboxymethyl cellulose, sodium saccharin, sodium phosphate, sodium bicarbonate, and a combination thereof,
wherein the anionic compound is present in an amount of at least 0.05 percent based the weight of the antiseptic composition; and
a solubilizing surfactant selected from the group consisting of zwitterionic surfactants, amine oxide surfactants, micelle-forming nonionic surfactants, and a combination thereof;
wherein the solubilizing surfactant is present in an amount greater than 80 wt-%, the anionic compound is present in an amount of less than 20 wt-%, and the multivalent cationic antiseptic is present in an amount of not more than 10 wt-%, wherein wt % is based upon the total weight of the combination of solubilizing surfactant, the anionic compound, and the multivalent cationic antiseptic, and
wherein the antimicrobial composition is free of precipitate according to Test Method A.

2. The antiseptic composition of claim 1, wherein the solubilizing surfactant, the anionic compound, and the multivalent cationic antiseptic are present in amounts within the boundary defined by A1, J1, and K1, and along the boundary lines of A1-J1, J1-K1, and K1-A1 of FIG. 1 of the accompanying drawings.

3. The antiseptic composition of claim 1, wherein the solubilizing surfactant is an amine oxide surfactant.

4. The antiseptic composition of claim 3, wherein the amine oxide surfactant is selected from compounds of the formula $(R^{14})_3$—N?O wherein $R^{14}$ is a (C1-C14)alkyl group, a (C6-C18)aralkyl, a (C6-C18)alkaryl group or a combination thereof, each of which is unsubstituted or substituted or interrupted at one or more carbon atoms by one or more N-, O-, or S-containing amido, ester, or hydroxyl groups and combinations thereof, and wherein each $R^{14}$ may be the same or different, and at least one $R^{14}$ group includes at least eight carbons.

5. The antiseptic composition of claim 4, wherein the amine oxide surfactant is selected from the group consisting of (C8-C22)alkyldi(C1-C4)alkylamine oxides, (C8-C22)aralkyldi(C1-C4)alkylamine oxides, (C8-C22)alkaryldi(C1-C4)alkylamine oxides, (C8-C22)alkylamido(C2-C4)alkylenyldi(C1-C4)alkylamine oxides, (C8-C22)aralkylamido(C2-C4)alkylenyldi(C1-C4)alkylamine oxides, (C8-C22)alkarylamido(C2-C4)alkylenyldi(C1-C4)alkylamine oxides, and combinations thereof.

6. The antiseptic composition of claim 4, wherein the amine oxide surfactant is selected from the group consisting of (C12-C16)alkyl(C1-C4)dialkylamine oxides, (C12-C16)alkylamido(C2-C4)alkylene(C1-4)dialkylamine oxides, and combinations thereof.

7. The antiseptic composition of claim 1, wherein the zwitterionic surfactant is selected from the group consisting of (C8-C22) alkyl and alkenyl betaines, (C8-C22) aralkyl betaines, (C8-C22) alkaryl betaines, (C8-C22) alkyl and alkenyl sultaines, (C8-C22) aralkyl sultaines, (C8-C22) alkaryl sultaines, each of which is unsubstituted or substituted or interrupted at one or more carbon atoms by one or more N-, O-, or S-containing amido, ester, or hydroxyl groups and combinations thereof.

8. The antiseptic composition of claim 1, wherein the anionic compound is present in an amount of at least 0.1 percent based upon the ready to use composition.

9. The antiseptic composition of claim 1, wherein the anionic compound is present in an amount of at least 1.2 wt-%, based upon the total weight of the solubilizing surfactant, the anionic compound, and the multivalent cationic antiseptic.

* * * * *